US012048925B2

(12) United States Patent
Fruchter et al.

(10) Patent No.: US 12,048,925 B2
(45) Date of Patent: *Jul. 30, 2024

(54) TESTING FOR PARTICULATES

(71) Applicant: HERO SCIENTIFIC LTD., Jerusalem (IL)

(72) Inventors: Lazar Fruchter, Efrat (IL); Arie Oscar Holtz, Jerusalem (IL); Robert Eric Levitz, Beit Shemesh (IL)

(73) Assignee: HERO SCIENTIFIC LTD., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/108,119

(22) Filed: Feb. 10, 2023

(65) Prior Publication Data

US 2023/0182128 A1     Jun. 15, 2023

Related U.S. Application Data

(63) Continuation of application No. 16/489,853, filed as application No. PCT/IL2018/050225 on Feb. 28, 2018, now Pat. No. 11,577,238.

(30) Foreign Application Priority Data

Mar. 2, 2017  (GB) ..................... 1703383

(51) Int. Cl.
 *C12Q 1/24* (2006.01)
 *B01L 3/00* (2006.01)
 *B01L 7/00* (2006.01)
 *C12Q 1/14* (2006.01)

(52) U.S. Cl.
 CPC ............ *B01L 3/502* (2013.01); *B01L 7/00* (2013.01); *C12Q 1/14* (2013.01); *C12Q 1/24* (2013.01); *B01L 2200/0647* (2013.01); *B01L 2200/0684* (2013.01); *B01L 2200/0689* (2013.01); *B01L 2300/044* (2013.01); *B01L 2300/0672* (2013.01); *B01L 2300/0681* (2013.01); *B01L 2300/0832* (2013.01); *B01L 2300/18* (2013.01); *B01L 2400/0487* (2013.01)

(58) Field of Classification Search
 None
 See application file for complete search history.

(56) References Cited

U.S. PATENT DOCUMENTS

| 1,856,811 | A | 5/1932 | Inaki |
| 2,425,945 | A | 8/1947 | Leach |
| 2,857,908 | A | 10/1958 | Cornfield |
| 3,295,686 | A | 1/1967 | Kruger |
| 3,449,081 | A | 6/1969 | Hughes |
| 3,481,712 | A | 12/1969 | Bernstein et al. |
| 3,745,090 | A | 7/1973 | Chappelle |
| 3,897,902 | A | 8/1975 | Yanez |
| 3,933,592 | A | 1/1976 | Clendenning |
| 3,971,703 | A | 7/1976 | Picciolo et al. |
| 4,144,134 | A | 3/1979 | Plakas |
| 4,303,752 | A | 12/1981 | Kolehmainen et al. |
| 4,421,848 | A | 12/1983 | Whitlock |
| 4,503,149 | A | 3/1985 | Boyd |
| 4,698,311 | A | 10/1987 | Hall et al. |
| 4,729,846 | A | 3/1988 | Matsui et al. |
| 4,829,005 | A | 5/1989 | Friedman et al. |
| 4,863,602 | A | 9/1989 | Johnson |
| 4,902,421 | A | 2/1990 | Pascale et al. |
| 4,906,565 | A | 3/1990 | Vossen |
| 5,024,237 | A | 6/1991 | Guirguis |
| 5,073,272 | A | 12/1991 | O'Neill et al. |
| 5,077,012 | A | 12/1991 | Guirguis |
| 5,139,031 | A | 8/1992 | Guirguis |
| 5,186,897 | A | 2/1993 | Eason et al. |
| 5,238,812 | A | 8/1993 | Coulter et al. |
| 5,258,285 | A | 11/1993 | Aegidius |
| 5,264,184 | A | 11/1993 | Aysta et al. |
| 5,339,829 | A | 8/1994 | Thieme et al. |

(Continued)

FOREIGN PATENT DOCUMENTS

| CN | 1084045 A | 3/1994 |
| CN | 102325598 A | 1/2012 |

(Continued)

OTHER PUBLICATIONS

Non-Final Office Action issued in U.S. Appl. No. 18/079,222, dated Apr. 28, 2023.
Non-Final Office Action issued in U.S. Appl. No. 18/093,942, dated May 12, 2023.
Invitation to Pay Additional Fees issued in PCT/IL2023/050014, dated Jun. 5, 2023.
English Translation of Office Action in Japanese Appl. No. JP 513275/2021, dated Jun. 27, 2023.
Arnold, John C. and Victor Nizet. (2002). 27 Pharyngitis. Clin Infect Dis. 35: 113-125.

(Continued)

*Primary Examiner* — Jana A Hines
*Assistant Examiner* — Khatol S Shahnan Shah
(74) *Attorney, Agent, or Firm* — Sughrue Mion, PLLC

(57) ABSTRACT

Apparatus is provided for testing a biological fluid for presence of a biological particulate. The apparatus includes a tube, a plunger sized and shaped to be inserted into and advanced within the tube, and a filter. The apparatus is configured such that as the plunger is advanced within the tube while the biological fluid is within the tube, the biological fluid in the tube is pushed through the filter, thereby trapping, by the filter, the biological particulate present in the biological fluid. The apparatus is shaped so as to define at least one enclosed cavity containing a biological particulate-presence-testing-facilitation solution configured to test for the presence of the biological particulate trapped by the filter. The enclosed cavity is configured to open while the plunger is inside the tube, so as to release the biological particulate-presence-testing-facilitation solution within the tube. Other embodiments are also described.

61 Claims, 30 Drawing Sheets

(56) References Cited

U.S. PATENT DOCUMENTS

| | | |
|---|---|---|
| 5,376,337 A | 12/1994 | Seymour |
| 5,403,551 A | 4/1995 | Galloway et al. |
| 5,405,527 A | 4/1995 | Covington |
| 5,427,739 A | 6/1995 | Meserol et al. |
| 5,429,742 A | 7/1995 | Gutman et al. |
| 5,576,185 A | 11/1996 | Coulter et al. |
| 5,595,653 A | 1/1997 | Good et al. |
| 5,634,885 A | 6/1997 | Kiro |
| 5,690,825 A | 11/1997 | Parton |
| 5,695,989 A | 12/1997 | Kalamasz |
| 5,736,351 A | 4/1998 | Miller et al. |
| 5,776,341 A | 7/1998 | Barnard et al. |
| 5,830,359 A | 11/1998 | Knight et al. |
| 5,868,928 A | 2/1999 | Bradley |
| 5,888,729 A | 3/1999 | Kacian et al. |
| 5,891,702 A | 4/1999 | Sakakibara et al. |
| 5,897,492 A | 4/1999 | Feller et al. |
| 5,905,029 A | 5/1999 | Andreotti et al. |
| 5,908,751 A | 6/1999 | Higo et al. |
| 5,980,456 A | 11/1999 | Falcone |
| 6,004,766 A | 12/1999 | Atrache et al. |
| 6,015,681 A | 1/2000 | Ralls et al. |
| 6,045,913 A | 4/2000 | Castle |
| 6,090,572 A | 7/2000 | Crosby |
| 6,140,040 A | 10/2000 | Palm et al. |
| 6,152,887 A | 11/2000 | Blume |
| 6,174,704 B1 | 1/2001 | Chu et al. |
| 6,197,598 B1 | 3/2001 | Schrier et al. |
| 6,200,767 B1 | 3/2001 | Sakakibara et al. |
| 6,207,445 B1 | 3/2001 | Crosby |
| 6,221,655 B1 | 4/2001 | Fung et al. |
| 6,251,660 B1 | 6/2001 | Muir et al. |
| 6,265,229 B1 | 7/2001 | Fodstad et al. |
| 6,451,260 B1 | 9/2002 | Dusterhoft et al. |
| 6,465,201 B1 | 10/2002 | Presente et al. |
| 6,531,578 B1 | 3/2003 | Webber et al. |
| 6,565,749 B1 | 5/2003 | Hou et al. |
| 6,576,460 B1 | 6/2003 | Baeumner et al. |
| 6,588,681 B2 | 7/2003 | Rothrum et al. |
| 6,641,543 B1 | 11/2003 | Osgoodby |
| 6,660,489 B2 | 12/2003 | Schrecengost et al. |
| 6,677,129 B1 | 1/2004 | Blume |
| 6,767,714 B2 | 7/2004 | Nazareth et al. |
| 6,811,971 B2 | 11/2004 | Klepp et al. |
| 6,824,560 B2 | 11/2004 | Pelton |
| 6,846,648 B2 | 1/2005 | Maes |
| 6,861,067 B2 | 3/2005 | McGhee et al. |
| 6,911,148 B1 | 6/2005 | Demmer et al. |
| 6,967,261 B1 | 11/2005 | Soerens et al. |
| 6,991,898 B2 | 1/2006 | O'Connor |
| 7,005,143 B2 | 2/2006 | Abuelyaman et al. |
| 7,045,913 B2 | 5/2006 | Ebrahim et al. |
| 7,052,831 B2 | 5/2006 | Fletcher et al. |
| 7,060,223 B2 | 6/2006 | Dicesare et al. |
| 7,083,911 B2 | 8/2006 | Wood et al. |
| 7,141,033 B2 | 11/2006 | Kanjilal et al. |
| 7,160,689 B2 | 1/2007 | Matsumoto et al. |
| 7,282,181 B2 | 10/2007 | Hudak et al. |
| 7,338,692 B2 | 3/2008 | Smith et al. |
| 7,422,868 B2 | 9/2008 | Fan et al. |
| 7,485,609 B2 | 2/2009 | Reddy et al. |
| 7,553,417 B2 | 6/2009 | Waller, Jr. et al. |
| 7,618,591 B2 | 11/2009 | Slowey et al. |
| 7,642,060 B2 | 1/2010 | Nagar et al. |
| 7,682,688 B2 | 3/2010 | Smith |
| 7,682,835 B2 | 3/2010 | Giordano |
| 7,824,732 B2 | 11/2010 | Sahouani et al. |
| 7,837,939 B2 | 11/2010 | Tung et al. |
| 7,927,548 B2 | 4/2011 | Slowey et al. |
| 7,935,161 B1 | 5/2011 | Adams et al. |
| 7,993,283 B1 | 8/2011 | Altschul |
| 8,030,088 B2 | 10/2011 | McCash et al. |
| 8,039,206 B1 | 10/2011 | Keenan |
| 8,057,608 B1 | 11/2011 | Saaski et al. |
| 8,069,690 B2 | 12/2011 | Desantolo et al. |
| 8,110,112 B2 | 2/2012 | Alburty et al. |
| 8,142,570 B1 | 3/2012 | Saaski et al. |
| 8,268,634 B2 | 9/2012 | Wu et al. |
| 8,272,255 B2 | 9/2012 | Halverson et al. |
| 8,278,091 B2 | 10/2012 | Rutter et al. |
| 8,281,937 B2 | 10/2012 | Collins et al. |
| 8,287,809 B2 | 10/2012 | Gould et al. |
| 8,322,539 B1 | 12/2012 | Ellis et al. |
| 8,343,726 B2 | 1/2013 | Boone et al. |
| 8,404,479 B2 | 3/2013 | Shimizu et al. |
| 8,475,739 B2 | 7/2013 | Holmes et al. |
| 8,541,242 B2 | 9/2013 | Boone et al. |
| 8,546,100 B2 | 10/2013 | Kshirsagar et al. |
| 8,562,572 B2 | 10/2013 | Proulx et al. |
| 8,563,264 B2 | 10/2013 | Halverson et al. |
| 8,569,072 B2 | 10/2013 | Halverson et al. |
| 8,584,535 B2 | 11/2013 | Page et al. |
| 8,597,878 B2 | 12/2013 | Hillebrand et al. |
| 8,603,008 B2 | 12/2013 | Libby et al. |
| 8,640,882 B2 | 2/2014 | Collins et al. |
| 8,647,508 B2 | 2/2014 | Halverson |
| 8,647,574 B2 | 2/2014 | Halverson et al. |
| 8,647,890 B2 | 2/2014 | Aberl et al. |
| 8,664,001 B2 | 3/2014 | Niskanen et al. |
| 8,685,746 B2 | 4/2014 | Halverson et al. |
| 8,709,796 B2 | 4/2014 | Faure et al. |
| 8,726,744 B2 | 5/2014 | Alburty et al. |
| 8,741,595 B2 | 6/2014 | Kshirsagar |
| 8,871,155 B2 | 10/2014 | Wu et al. |
| 8,898,069 B2 | 11/2014 | Hood et al. |
| 8,900,462 B2 | 12/2014 | Yamada et al. |
| 8,940,527 B2 | 1/2015 | Guirguis |
| 9,044,694 B2 | 6/2015 | Hacker et al. |
| 9,103,843 B2 | 8/2015 | Nieuwenhuis et al. |
| 9,113,850 B2 | 8/2015 | Skakoon |
| 9,115,382 B2 | 8/2015 | Bell |
| 9,295,453 B2 | 3/2016 | Katz |
| 9,297,804 B2 | 3/2016 | Palmon et al. |
| 9,314,570 B2 | 4/2016 | Kim |
| 9,327,284 B2 | 5/2016 | Rosman et al. |
| 9,328,325 B2 | 5/2016 | Kshirsagar et al. |
| 9,360,404 B2 | 6/2016 | Okanojo et al. |
| 9,381,000 B2 | 7/2016 | Morsey |
| 9,382,570 B2 | 7/2016 | Rajagopal et al. |
| 9,388,448 B2 | 7/2016 | Halverson |
| 9,470,612 B2 | 10/2016 | Rajagopal et al. |
| 9,482,351 B2 | 11/2016 | Proulx et al. |
| 9,546,391 B2 | 1/2017 | Rey et al. |
| 9,592,508 B2 | 3/2017 | Holmes et al. |
| 9,675,755 B2 | 6/2017 | Shick et al. |
| 9,709,468 B2 | 7/2017 | Ebi et al. |
| 9,719,125 B2 | 8/2017 | Kshirsagar et al. |
| 9,945,855 B2 | 4/2018 | Carrino et al. |
| 9,987,633 B2 | 6/2018 | Roscoe et al. |
| 10,106,830 B2 | 10/2018 | Maitra et al. |
| 10,376,878 B2 | 8/2019 | Calanca et al. |
| 10,612,258 B2 | 4/2020 | Coelho et al. |
| 10,993,705 B2 | 5/2021 | Katz et al. |
| 2002/0127630 A1 | 9/2002 | Diguiseppi et al. |
| 2003/0003441 A1 | 1/2003 | Colston et al. |
| 2003/0057147 A1 | 3/2003 | Sutcliffe |
| 2003/0064526 A1 | 4/2003 | Niedbala et al. |
| 2003/0092086 A1 | 5/2003 | Hirata et al. |
| 2003/0098271 A1 | 5/2003 | Somack et al. |
| 2003/0104507 A1 | 6/2003 | Wood et al. |
| 2003/0153021 A1 | 8/2003 | Lu et al. |
| 2003/0211566 A1 | 11/2003 | Gazenko |
| 2004/0005246 A1 | 1/2004 | Efthimiadis et al. |
| 2004/0038425 A1 | 2/2004 | Ferguson et al. |
| 2004/0149636 A1 | 8/2004 | Backes |
| 2004/0157971 A1 | 8/2004 | Kim |
| 2004/0161788 A1 | 8/2004 | Chen et al. |
| 2004/0197845 A1 | 10/2004 | Hassibi et al. |
| 2004/0220498 A1 | 11/2004 | Li et al. |
| 2005/0048592 A1 | 3/2005 | Wood et al. |
| 2005/0070701 A1 | 3/2005 | Hochstetler et al. |
| 2005/0142571 A1 | 6/2005 | Parthasarathy et al. |
| 2005/0152992 A1 | 7/2005 | Johnson, Jr. et al. |
| 2005/0153423 A1 | 7/2005 | Baba et al. |

(56) References Cited

U.S. PATENT DOCUMENTS

| | | |
|---|---|---|
| 2005/0181467 A1 | 8/2005 | Schrecengost et al. |
| 2005/0189290 A1 | 9/2005 | Maiden |
| 2005/0244943 A1 | 11/2005 | Ladisch et al. |
| 2005/0250138 A1 | 11/2005 | Young et al. |
| 2006/0062854 A1 | 3/2006 | Chandra et al. |
| 2006/0166347 A1 | 7/2006 | Faulstich et al. |
| 2006/0184085 A1 | 8/2006 | Kimura et al. |
| 2006/0273049 A1 | 12/2006 | Leach et al. |
| 2007/0062870 A1 | 3/2007 | Chen et al. |
| 2007/0148458 A1 | 6/2007 | Sahouani et al. |
| 2007/0212266 A1 | 9/2007 | Johnston et al. |
| 2007/0254320 A1 | 11/2007 | Olstein |
| 2007/0269341 A1 | 11/2007 | Halverson et al. |
| 2008/0023408 A1 | 1/2008 | Hansen |
| 2008/0064939 A1 | 3/2008 | Reynolds et al. |
| 2008/0078717 A1 | 4/2008 | Shigesada et al. |
| 2008/0153125 A1 | 6/2008 | Buttry et al. |
| 2008/0207794 A1 | 8/2008 | Wright et al. |
| 2009/0011403 A1 | 1/2009 | Smith et al. |
| 2009/0068065 A1 | 3/2009 | Pagoria et al. |
| 2009/0258411 A1 | 10/2009 | Petithory et al. |
| 2009/0281483 A1 | 11/2009 | Baker et al. |
| 2010/0190171 A1 | 7/2010 | Kshirsagar et al. |
| 2010/0209927 A1 | 8/2010 | Menon et al. |
| 2010/0209961 A1 | 8/2010 | Kshirsagar et al. |
| 2010/0248214 A1 | 9/2010 | Kshirsagar et al. |
| 2010/0248350 A1 | 9/2010 | Gazenko |
| 2010/0273177 A1 | 10/2010 | Piasio et al. |
| 2011/0315625 A1 | 12/2011 | Keenan et al. |
| 2011/0318814 A1 | 12/2011 | Kshirsagar et al. |
| 2012/0107799 A1 | 5/2012 | Daum |
| 2012/0156114 A1 | 6/2012 | Ziegman et al. |
| 2012/0203167 A1 | 8/2012 | Johnson |
| 2012/0301907 A1 | 11/2012 | Sellappan et al. |
| 2013/0023443 A1 | 1/2013 | Shirai et al. |
| 2013/0059290 A1 | 3/2013 | Armes |
| 2013/0244225 A1 | 9/2013 | Kshirsagar et al. |
| 2013/0260370 A1 | 10/2013 | Kshirsagar et al. |
| 2014/0110356 A1 | 4/2014 | McKay |
| 2014/0315221 A1 | 10/2014 | Morsey |
| 2015/0010918 A1 | 1/2015 | Ruvinsky |
| 2015/0031040 A1 | 1/2015 | Calanca et al. |
| 2015/0076069 A1 | 3/2015 | Ellis et al. |
| 2015/0093749 A1 | 4/2015 | Ling |
| 2015/0133574 A1 | 5/2015 | Kshirsagar et al. |
| 2016/0209305 A1 | 7/2016 | Kshirsagar et al. |
| 2016/0296927 A1 | 10/2016 | Kirschhoffer et al. |
| 2016/0341641 A1 | 11/2016 | Williams et al. |
| 2017/0043336 A1 | 2/2017 | Khattak et al. |
| 2017/0248503 A1 | 8/2017 | Kshirsagar et al. |
| 2017/0283792 A1 | 10/2017 | Benitez Porras et al. |
| 2018/0051313 A1 | 2/2018 | Rajagopal et al. |
| 2018/0339292 A1 | 11/2018 | Katz et al. |
| 2020/0140251 A1 | 5/2020 | Katz et al. |
| 2022/0288583 A1 | 9/2022 | Katz et al. |

FOREIGN PATENT DOCUMENTS

| | | |
|---|---|---|
| CN | 206910919 U | 1/2018 |
| CN | 109567967 A | 4/2019 |
| EP | 0364173 A1 | 4/1990 |
| EP | 0378353 A2 | 7/1990 |
| EP | 0 520 408 A2 | 12/1992 |
| EP | 0 952 209 A2 | 10/1999 |
| EP | 1089800 B1 | 11/2003 |
| EP | 1166078 B1 | 9/2004 |
| EP | 1674867 B1 | 7/2009 |
| EP | 2214830 B1 | 9/2012 |
| EP | 2214829 B1 | 12/2012 |
| EP | 2217378 B1 | 2/2013 |
| EP | 2217377 B1 | 9/2013 |
| EP | 1907527 B1 | 2/2016 |
| EP | 3290920 A1 | 3/2018 |
| EP | 2868742 B1 | 8/2018 |
| GB | 2411668 B | 7/2008 |
| JP | 1-312991 A | 12/1989 |
| JP | 5-203649 A | 8/1993 |
| JP | 2002-153297 A | 5/2002 |
| JP | 2003-38162 A | 2/2003 |
| JP | 2003-215126 A | 7/2003 |
| JP | 2004-279113 A | 10/2004 |
| JP | 2005-257604 A | 9/2005 |
| JP | 2006-167411 A | 6/2006 |
| JP | 2013-107 A | 1/2013 |
| JP | 2017-181131 A | 10/2017 |
| JP | 6931839 B1 | 9/2021 |
| WO | 89/09279 A1 | 10/1989 |
| WO | 93/01271 A1 | 1/1993 |
| WO | 96/04067 A1 | 2/1996 |
| WO | 00/21973 A1 | 4/2000 |
| WO | 00/29112 A1 | 5/2000 |
| WO | 01/14257 A1 | 3/2001 |
| WO | 03/069301 A2 | 8/2003 |
| WO | 2004/015413 A1 | 2/2004 |
| WO | 2006/100452 A1 | 9/2006 |
| WO | 2007/050072 A1 | 5/2007 |
| WO | 2007/137257 A2 | 11/2007 |
| WO | 2008/075044 A2 | 6/2008 |
| WO | 2008/093329 A2 | 8/2008 |
| WO | 2009/018544 A1 | 2/2009 |
| WO | 2009/048743 A1 | 4/2009 |
| WO | 2009/067498 A1 | 5/2009 |
| WO | 2009/067503 A1 | 5/2009 |
| WO | 2009/067513 A1 | 5/2009 |
| WO | 2009/067518 A1 | 5/2009 |
| WO | 2009/082667 A1 | 7/2009 |
| WO | 2010/056128 A1 | 5/2010 |
| WO | 2012/031156 A1 | 3/2012 |
| WO | 2013/013253 A1 | 1/2013 |
| WO | 2013/082301 A1 | 6/2013 |
| WO | 2014/048263 A1 | 4/2014 |
| WO | 2014/145810 A2 | 9/2014 |
| WO | 2017/027956 A1 | 2/2017 |
| WO | 2017/112911 A1 | 6/2017 |
| WO | 2018/102783 A1 | 6/2018 |
| WO | 2019/060950 A1 | 4/2019 |
| WO | 2019/139901 A1 | 7/2019 |
| WO | 2021/229564 A1 | 11/2021 |

OTHER PUBLICATIONS

Bernheimer, A. W. and Pappenheimer A. M. Jr., "Factors necessary for massive growth of Group A hemolytic *Streptococcus*". Journal of Bacteriology, vol. 43(4), pp. 481/494 (1941).

Decelle JG & Taylor GR. (1976). Autoflora in the Upper Respiratory Tract of Apollo Astronauts. Applied and Environmental Microbiology. 32(5): 659-665.

Edwards E.A. et al., "Diagnosis of Group A Streptococcal Infections Directly from Throat Secretions," Journal of Clinical Microbiology Mar. 1982, p. 481-483 (1982).

Covalciuc KA et al., "Comparison of Four Clinical Specimen Types for Detection of Influenza A and B Viruses by Optical Immunoassay (FLU OIA Test) and Cell Culture Methods," Journal of Clinical Microbiology, Dec. 1999, p. 3971-3974.

Bisno, Alan L., Michael A. Gerber, Jack M. Gwaltney Jr., Edward L. Kaplan, and Richard H. Schwartz. (2002). Practice Guidelines for the Diagnosis and Management of Group A Streptococcal Pharyngitis. Clinical Infectious Diseases. 35: 113-125.

Fox, James W et al., "Diagnosis of Streptococcal Pharyngitis by Detection of *Streptococcus pyogenes* in Posterior Pharyngeal versus Oral Cavity Specimens," Journal of Clinical Microbiology, Jul. 2006. p. 2593-2594.

Gao Y et al., "The Scl1 of M41-type group A *Streptococcus* binds the highdensity lipoprotein," FEMS Microbiol Lett. Aug. 1, 2010; 309(1).

Garbieri et al., "Human DNA extraction from whole saliva that was fresh or stored for 3, 6 or 12 months using five different protocols," J. Appl. Oral Sci. vol. 25 No. 2 Bauru Mar./Apr. 2017.

Hamburger, Morton Jr. (1944). Studies on the Transmission of Hemolytic *Streptococcus* Infections: II. Beta Hemolytic Streptococci in the Saliva of Persons with Positive Throat Cultures. The

(56) References Cited

OTHER PUBLICATIONS

Journal of Infectious Diseases. 75(1): 71-78. https://www.jstor.org/stable/30089409.
Johnston DA & Bodey GP. (1970). Semiquantitative Oropharyngeal Culture Technique. Applied Microbiology. 20(2): 218-223.
Jordens JZ, et al. (2002). Detection of Meningococcal Carriage by Culture and PCR of Throat Swabs and Mouth Gargles. J Clin Microbiol. 40(1): 75-79.
Kaplan, Edward L., Robert Couser, Barbara Ballard Huwe, Carolyn Mckay, and Lewis W. Wannamaker. (1979). Significance of Quantitative Salivary Cultures for Group A and Non-group A Beta-Hemolytic Streptococci in Patients with Pharyngitis and in Their Family Contacts. Pediatrics. 64(6): 904-912.
Karaby O et al., "Efficacy of Throat Gargling for Detection of Group A Beta-Hemolytic Streptococcus," Jpn. J. Infect. Dis. 58, 39-40, 2005.
McKesson Strep_A_5003_insert_2015_12.
Spellerberg, Barbara and Claudia Brandt. (2016). Laboratory Diagnosis of *Streptococcus pyogenes* (group A streptococci). In Ferretti JJ, Stevens DL, Fischetti VA (Ed). *Streptococcus pyogenes*: Basic Biology to Clinical Manifestations [Internet]. Oklahoma City (OK): University of Oklahoma Health Sciences Center. 2016.
Thermo Scientific Titan3 and Target2 Syringe Filters Product Catalog 2016.
Yilmaz F et al. (Abstract) 2008, "Effectiveness of rapid antigen test with throat gargle in detecting group A beta-hemolytic streptococci," Kulak Burun Bogaz Ihtis Derg. Sep.-Oct. 2008;18(5):280-3.
Yilmaz, Fahrettin, et al.(2008). Boğaz gargarasi ile yapilan hizli antijen testinin grup A beta-hemolitik streptokoklari saptamadaki etkinliği. Kulak Burun Bogaz Ihtis Derg. 18(5): 280-283. Klinik Çalişma. Turkish.
Yilmaz, Fahrettin, et al. (2008). Effectiveness of rapid antigen test with throat gargle in detecting group A beta-hemolytic streptococci. Journal of Ear Nose and Throat. 18(5): 280-283. Clinical Study. Google Translation.
An International Search Report and a Written Opinion both dated Jun. 29, 2020, which issued during the prosecution of Applicant's PCT/IL2019/050997.
An International Search Report and a Written Opinion both dated Dec. 31, 2019, which issued during the prosecution of Applicant's PCT/IL2019/050994.
An International Search Report and a Written Opinion both dated Aug. 23, 2018, which issued during the prosecution of Applicant's PCT/IL2018/050225.
An Invitation to pay additional fees dated Mar. 3, 2020, which issued during the prosecution of Applicant's PCT/IL2019/050997.
An Office Action dated Jul. 21, 2017, which issued during the prosecution of UK Patent Application No. 1703383.8.
An Invitation to pay additional fees dated Jun. 12, 2018, which issued during the prosecution of Applicant's PCT/IL2018/050225.
"DNA extraction from water: 50-50-50 buffer-chloroform/phenol method", Laboratory for Environmental Pathogens Research, Department of Environmental Sciences, University of Toledo, Oct. 1, 2004, pp. 1-5.
International Search Report and Written Opinion dated Dec. 3, 2020, in International Application No. PCT/IL2020/050957.
Invitation to Pay Additional Fees issued May 25, 2022 in International Application No. PCT/IL2022/050024.
ISR and Written Opinion in PCT/IL2021/051035, dated Jan. 10, 2022.
Karabay et al., "Efficacy of Throat Gargling for Detection of Group A Beta-Hemolytic *Streptococcus*", Jpn. J. Infect. Dis., 2005, vol. 58, pp. 39-40.
Notice of Allowance issued in the counterpart Chinese Application CN 201880028401.4 dated Oct. 25, 2022.
Office Action dated Jul. 15, 2022 in U.S. Appl. No. 17/122,594.
Office Action dated Jul. 8, 2022 in European Application No. 19769600.8.
Official Action dated Oct. 15, 2021 in Chinese Appl. No. CN 201880028401.4.
"Oil filter", Wikipedia, Accessed via the Internet: https://en.wikipedia.org/w/index.php?title=Oil_filter&oldid=978674262 Nov. 24, 2020 (5 pages total).
Translation of Office Action dated Apr. 15, 2022 in Chinese Application No. 201880028401.4.
Written Opinion of the International Searching Authority dated Jul. 21, 2022 in International Application No. PCT/IL2022/050024.
International Search Report dated Jun. 22, 2021 in International Application No. PCT/IB2021/052055.
Written Opinion of the International Searching Authority dated Jun. 22, 2021 in International Application No. PCT/IB2021/052055.
International Search Report dated Jun. 22, 2021 in International Application No. PCT/IB2021/052056.
Written Opinion of the International Searching Authority dated Jun. 22, 2021 in International Application. No. PCT/IB2021/052056.
Ek et al., "A combination of naso- and oropharyngeal swabs improves the diagnostic yield of respiratory viruses in adult emergency department patients", Infectious Diseases, 2019, vol. 51, No. 4, pp. 241-248.
Kim et al., "Comparison of Nasopharyngeal and Oropharyngeal Swabs for the Diagnosis of Eight Respiratory Viruses by Real-Time Reverse Transcription-PCR Assays", PLoS ONE, Jun. 2011, vol. 6, Issue 6, e21610, pp. 1-6.
Dou et al., "A low-cost microfluidic platform for rapid and instrument-free detection of whooping cough", Analytica Chimica Acta, 2019, vol. 1065, pp. 71-78.
Duverlie et al., "A nylon membrane enzyme immunoassay for rapid diagnosis of influenza A infection", Journal of Virological Methods, 1992, vol. 40, pp. 77-84.
Black et al., "Reverse transcriptase-polymerase chain reaction for the detection of equine rhinitis B viruses and cell culture isolation of the virus", Arch Virol, 2007, vol. 152, pp. 137-149.
International Search Report and Written Opinion dated Aug. 4, 2021 in International Application No. PCT/IL2021/050519.
Non-Final Office Action dated Mar. 25, 2021 in U.S. Appl. No. 16/489,853.
Final Office Action dated Aug. 24, 2021 in U.S. Appl. No. 16/489,853.
Non-Final Office Action dated Apr. 1, 2022 in U.S. Appl. No. 16/489,853.
Notice of Allowance including Examiner's Interview Summary dated Nov. 15, 2022 in U.S. Appl. No. 16/489,853.
Office Action dated Oct. 20, 2023 by the United States Patent and Trademark Office in U.S. Appl. No. 18/093,939.

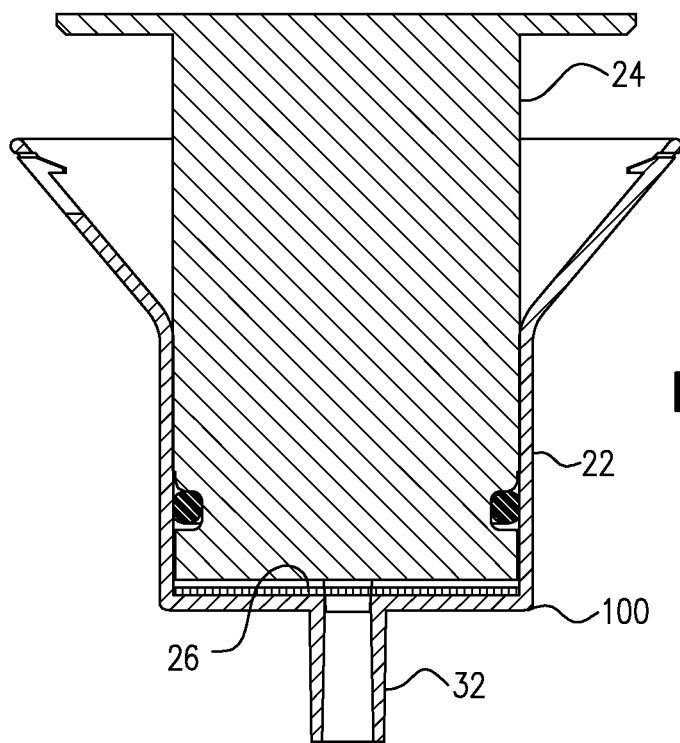
FIG. 11A
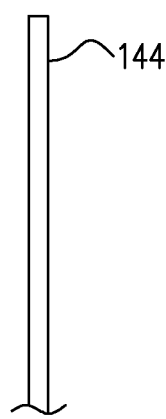

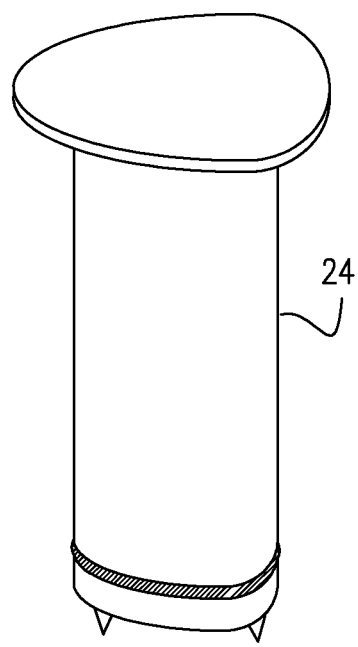
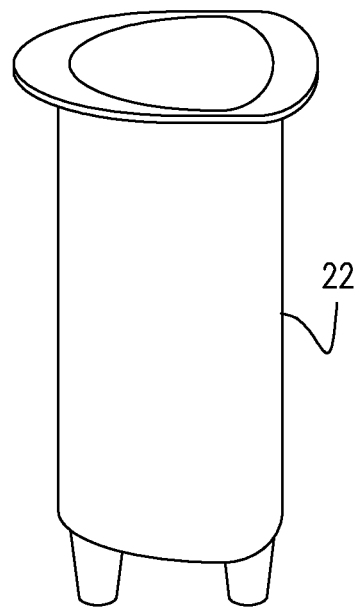
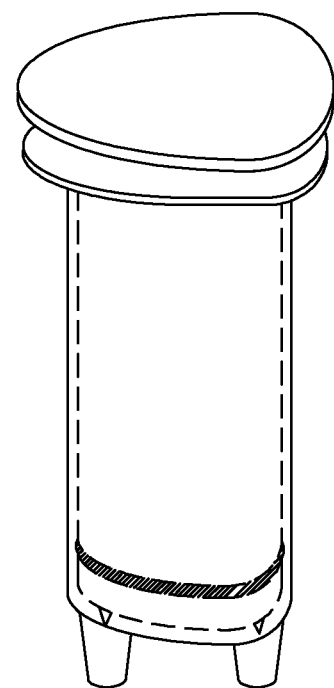
FIG. 14A                    FIG. 14B

TESTING FOR PARTICULATES

CROSS-REFERENCE TO RELATED APPLICATIONS

The present application is a continuation of U.S. application Ser. No. 16/489,853, filed Aug. 29, 2019, now U.S. Pat. No. 11,577,238, which is the U.S. national stage of International Application PCT/IL2018/050225, filed Feb. 28, 2018, which claims priority from UK Application GB1703383.8 to Fruchter, filed Mar. 2, 2017, entitled, "Testing for biological particulates," all of which applications are incorporated herein by reference.

FIELD OF THE INVENTION

Applications of the present invention relate to testing for the presence of particulates, such as bacteria, in fluids.

BACKGROUND

Streptococcal pharyngitis, streptococcal tonsillitis, or streptococcal sore throat (known colloquially as strep throat) is a type of pharyngitis caused by group A beta hemolytic streptococcus bacteria. Common symptoms include fever, sore throat, and enlarged cervical lymph nodes.

The rapid strep test is commonly used to test for the presence of group A streptococcus bacteria. In this test, a swab is streaked across the throat to collect bacteria, and is subsequently inserted into an extraction solution, e.g., a mixture of 2M sodium nitrite (hereinbelow, "solution A"), and 0.2M acetic acid (hereinbelow, "solution B"). (Hereinbelow, this mixture is sometimes referred to as "A and B solution.") The extraction solution extracts strep A carbohydrate antigen from the bacteria. A dipstick containing an antibody specific to strep A carbohydrate antigen is inserted into the mixture containing the antigen. The mixture migrates up the dipstick and reacts with the antibody, thus generating a line on the dipstick. The presence of this line indicates a positive test result.

Other clinical situations also call for testing for presence of a particulate. For example, a physician may wish to test a patient's blood for the presence of a virus, or a stool specimen for the presence of a pathogen.

SUMMARY OF THE INVENTION

Applications of the present invention include apparatus for testing a fluid for presence of a particulate such as a microorganism, a spore, a virus, or other biological entity, e.g., a biological cell. The apparatus includes a tube and a plunger sized and shaped to be advanceable within the tube while sealably contacting the tube. First, the fluid that potentially contains the particulate is collected in the tube. Subsequently, the plunger is used to push the fluid through a filter. The filter may be disposed at the distal end of the tube, the fluid being pushed through the filter and out of the tube. Alternatively, the filter is disposed on the distal end of the plunger, and the fluid is pushed through the filter and into one or more compartments in the plunger. Following the pushing of the fluid through the filter, and while the filter is inside the tube, the filter may be tested for presence of the particulate. For example, the tube and plunger may be turned upside down, and the rapid strep test may then be conducted via an opening at the distal end of the tube. Alternatively or additionally, a throat culture may be performed on the bacteria collected on the filter.

Typically, types of particulates that may be tested for include a microorganism (e.g., a parasite), a fungus, a bacteria, a spore (e.g., a pollen spore), a virus, a mite, a biological cell (e.g., a cancerous cell), a biological antigen, a protein, a protein antigen, and a carbohydrate antigen.

There is therefore provided in accordance with some applications of the present invention, a method for testing for presence of a particulate selected from the group consisting of: a microorganism, a fungus, a bacteria, a spore, a virus, a mite, a biological cell, a biological antigen, a protein, a protein antigen, and a carbohydrate antigen, the method including:

collecting, in a tube, fluid that potentially contains the particulate;

using a plunger, pushing the fluid through a filter disposed at a location selected from the group consisting of: a distal portion of the tube, and a distal end of the plunger; and subsequently, while the filter is inside the tube, ascertaining if any of the particulate was trapped by the filter by applying a particulate-presence-testing-facilitation solution to the filter.

For some applications, ascertaining includes ascertaining using a first protocol, and if no particulate is found to be present, ascertaining using a second protocol.

For some applications, ascertaining using the first protocol includes applying the particulate-presence-testing-facilitation solution to the filter, the method further including taking a sample from the filter prior to applying the particulate-presence-testing-facilitation solution to the filter.

For some applications, the method further includes culturing the sample taken from the filter for 2-48 hours, and ascertaining using the second protocol includes ascertaining if any of the particulate is present in the sample after the 2-48 hours.

For some applications, collecting the fluid in the tube includes collecting gargled fluid in the tube.

For some applications, a temperature of the gargled fluid is 1-38 degrees Celsius.

For some applications,
the particulate includes a microorganism,
the particulate-presence-testing-facilitation solution includes a releasing agent configured to release an antigen from the microorganism, and
testing for presence of the particulate includes testing for presence of the particulate by testing for presence of the antigen.

For some applications, using the plunger to push the fluid through the filter includes advancing the plunger at least until the plunger contacts the filter.

For some applications, the method further includes puncturing the filter before testing for presence of the particulate.

For some applications, testing for presence of the particulate includes testing for presence of the particulate while a distal opening of the tube is above a proximal opening of the tube, and the plunger and tube are resting on a horizontal surface, on a proximal end of the plunger.

For some applications, testing for presence of the particulate includes testing for presence of the particulate while a distal opening of the tube is above a proximal opening of the tube, and the plunger and tube are resting on a horizontal surface, on a proximal end of the tube.

There is further provided, in accordance with some applications of the present invention, a method for testing for presence of a particulate selected from the group consisting of: a microorganism, a fungus, a bacteria, a spore, a virus, a mite, a biological cell, a biological antigen, a protein, a protein antigen, and a carbohydrate antigen, the method including:

collecting, in a tube having a filter, fluid that potentially contains the particulate;

passing the fluid through the filter; and subsequently, while the filter is inside the tube, testing for presence of the particulate, by ascertaining if any of the particulate was trapped by the filter by applying a particulate-presence-testing-facilitation solution to the filter.

For some applications, ascertaining includes ascertaining using a first protocol, and if no particulate is found to be present, ascertaining using a second protocol.

For some applications, ascertaining using the first protocol includes applying the particulate-presence-testing-facilitation solution to the filter, the method further including taking a sample from the filter prior to applying the particulate-presence-testing-facilitation solution to the filter.

For some applications, the method further includes culturing the sample taken from the filter for 2-48 hours, and ascertaining using the second protocol includes ascertaining if any of the particulate is present in the sample after the 2-48 hours.

For some applications, collecting the fluid in the tube includes collecting gargled fluid in the tube.

For some applications, a temperature of the gargled fluid is 1-38 degrees Celsius.

There is further provided, in accordance with some applications of the present invention, apparatus including:

a tube having a funnel-shaped proximal opening, a proximal-most diameter of the funnel-shaped proximal opening being at least 20% greater than a diameter of the tube;

a plunger sized and shaped to be advanceable within the tube while sealably contacting the tube; and a filter disposed at a location selected from the group consisting of: a distal portion of the tube, and a distal end of the plunger.

For some applications, the proximal-most diameter of the funnel-shaped proximal opening is at least 30% greater than the diameter of the tube.

There is therefore provided, in accordance with some applications of the present invention, apparatus including:

a tube, closed at a distal end thereof;

a filter disposed within the tube, the tube being shaped to define a fluid-collection compartment distal to the filter; and a plunger sized and shaped to be advanceable within the tube while sealably contacting the tube, the plunger being arranged to push a fluid through the filter and into the fluid-collection compartment.

There is further provided, in accordance with some applications of the present invention, a method for testing for presence of a particulate selected from the group consisting of: a microorganism, a fungus, a bacteria, a spore, a virus, a mite, a biological cell, a biological antigen, a protein, a protein antigen, and a carbohydrate antigen, the method including:

collecting, in a tube, fluid that potentially contains the particulate;

pushing the fluid through a filter, disposed within the tube, into a fluid-collection compartment distal to the filter; and subsequently, while the filter is inside the tube, testing for presence of the particulate, by ascertaining if any of the particulate was trapped by the filter.

There is further provided, in accordance with some applications of the present invention, a method for testing for presence of a particulate selected from the group consisting of: a microorganism, a fungus, a bacteria, a spore, a virus, a mite, a biological cell, a biological antigen, a protein, a protein antigen, and a carbohydrate antigen, the method including:

collecting, in a tube, fluid that potentially contains the particulate;

pushing the fluid through a filter disposed within a distal portion of the tube;

tearing the filter while the filter is inside the tube; and subsequently, while the filter is inside the tube, testing for presence of the particulate, by ascertaining if any of the particulate was trapped by the filter.

There is further provided, in accordance with some applications of the present invention, apparatus including:

a tube;

a plunger sized and shaped to be advanceable within the tube, a ratio of (a) a diameter of a proximal end of the plunger, to (b) a length of the plunger, being at least 1; and a filter disposed at a location selected from the group consisting of: a distal portion of the tube, and a distal end of the plunger.

There is further provided, in accordance with some applications of the present invention, apparatus including:

a tube; and a plunger sized and shaped to be advanceable within the tube while sealably contacting the tube, a proximally-facing surface at a distal end of the tube inhibiting advancement of the plunger;

the plunger and tube being shaped to provide an empty volume of 0.03-5 mL proximal to the proximally-facing surface, when the plunger is maximally advanced within the tube.

For some applications, the empty volume is 0.03-1 mL.

For some applications, the apparatus further includes a filter disposed within a distal portion of the tube.

For some applications, the apparatus further includes a puncturing element protruding from a distal end of the plunger, the puncturing element being configured to puncture the filter upon the plunger being advanced to the filter.

For some applications, the apparatus further includes (a) a kit in which the plunger and tube are disposed, and (b) a puncturing element disposed within the kit, the puncturing element being sized and shaped to be passable through an opening at a distal end of the tube and configured to puncture the filter by being longer than a distance from (i) the opening at the distal end of the tube to (ii) the filter.

For some applications, a distal end of the plunger is shaped to define a distally-facing cavity therein, the cavity providing at least part of the empty volume.

For some applications, a volume of the cavity is between 0.03 and 5 mL.

For some applications, the volume of the cavity is 0.03-1 mL.

For some applications, the volume of the cavity is at least 0.15 mL.

For some applications, the volume of the cavity is at least 0.25 mL.

For some applications, the volume of the cavity is at least 0.4 mL.

For some applications, the tube does not include a Luer lock.

For some applications, the tube does not include a needle-coupling mechanism.

For some applications, the apparatus further includes a kit in which the plunger and tube are disposed, the plunger being disposed entirely outside of the tube.

For some applications, a distal end of the plunger is not convex.

For some applications, a volume of the tube is between 1 and 70 mL.

For some applications, the volume of the tube is between 1 and 8 mL.

For some applications, the volume of the tube is between 8 and 15 mL.

For some applications, the volume of the tube is between 15 and 30 mL.

For some applications, the volume of the tube is between 30 and 70 mL.

For some applications, the apparatus further includes (a) a kit in which the plunger and tube are disposed, and (b) a particulate-presence-testing-facilitation solution disposed within the kit, the particulate selected from the group consisting of: a microorganism, a fungus, a bacteria, a spore, a virus, a mite, a biological cell, a biological antigen, a protein, a protein antigen, and a carbohydrate antigen.

For some applications, a distal end of the plunger is shaped to define at least one enclosed cavity containing a particulate-presence-testing-facilitation solution,
the enclosed cavity being configured to open upon the plunger being moved within the tube, and
the particulate selected from the group consisting of: a microorganism, a fungus, a bacteria, a spore, a virus, a mite, a biological cell, a biological antigen, a protein, a protein antigen, and a carbohydrate antigen.

For some applications, a distal end of the plunger is shaped to define at least one enclosed cavity containing a particulate-presence-testing-facilitation solution,
the enclosed cavity being configured to open while the plunger is inside the tube, and
the particulate selected from the group consisting of: a microorganism, a fungus, a bacteria, a spore, a virus, a mite, a biological cell, a biological antigen, a protein, a protein antigen, and a carbohydrate antigen.

For some applications, a wall of the tube is shaped to define at least one enclosed cavity containing a particulate-presence-testing-facilitation solution,
a wall of the enclosed cavity being configured to open upon the plunger being moved within the tube, and
the particulate selected from the group consisting of: a microorganism, a fungus, a bacteria, a spore, a virus, a mite, a biological cell, a biological antigen, a protein, a protein antigen, and a carbohydrate antigen.

For some applications, a wall of the tube is shaped to define at least one enclosed cavity containing a particulate-presence-testing-facilitation solution,
a wall of the enclosed cavity being configured to open, and
the particulate selected from the group consisting of: a microorganism, a fungus, a bacteria, a spore, a virus, a mite, a biological cell, a biological antigen, a protein, a protein antigen, and a carbohydrate antigen.

For some applications, the enclosed cavity further contains a gas above atmospheric pressure, such that the particulate-presence-testing-facilitation solution is forced out upon the opening of the wall of the cavity.

For some applications, the plunger is shaped to define at least one plunger lumen containing a particulate-presence-testing-facilitation solution,
the particulate selected from the group consisting of: a microorganism, a fungus, a bacteria, a spore, a virus, a mite, a biological cell, a biological antigen, a protein, a protein antigen, and a carbohydrate antigen.

For some applications, the plunger lumen is configured to open upon the plunger being moved within the tube.

For some applications, the plunger lumen is configured to open while the plunger is inside the tube.

For some applications, the plunger lumen further contains a gas above atmospheric pressure, such that the particulate-presence-testing-facilitation solution is forced out of the plunger lumen upon opening of the plunger lumen.

For some applications, the apparatus further includes at least one sub-plunger configured to be slidably disposed within the plunger lumen and to deploy the particulate-presence-testing-facilitation solution.

For some applications, a proximal end of the tube is shaped to define a funnel.

For some applications, a distal end of the tube is shaped to define a conduit.

For some applications, a distal end of the tube is funnel-shaped.

For some applications, a ratio of a diameter of a proximal opening of the tube to a diameter of a distal opening of the tube is at least 13.

For some applications, a proximal end of the plunger is not proximal to a proximal end of the tube, when the plunger is maximally advanced within the tube.

For some applications,
the plunger is shaped to define a plunger lumen, and
the apparatus further includes a shaft shaped to be slidably disposed within the plunger lumen, a distal end of the shaft including a puncturing element.

There is further provided, in accordance with some applications of the present invention, apparatus including:
a tube;
a plunger sized and shaped to be advanceable within the tube while sealably contacting the tube, a distal end of the plunger shaped to define one or more passageways therethrough; and
a filter coupled to the distal end of the plunger.

For some applications, the plunger is shaped to define one or more compartments in fluid communication with the passageways.

For some applications, the apparatus further includes (a) a first sealing ring surrounding the plunger proximally to the compartments, and (b) a second sealing ring surrounding the plunger distally to the compartments.

For some applications, a total volume of the compartments is between 0.5 and 60 mL.

For some applications, the total volume is between 5 and 30 mL.

For some applications, the total volume is between 8 and 20 mL.

For some applications, the plunger is shaped to define a disk proximal to the compartments, the disk being configured to inhibit passage of liquid from the compartments to a proximal side of the disk, when the disk is inside the tube.

For some applications, the tube includes a distal cylindrical portion, a length of the plunger distal to the disk being within 10 mm of a height of the cylindrical portion.

For some applications, the tube further includes a proximal funnel portion coupled to the cylindrical portion.

For some applications, a length of the plunger proximal to the disk is not greater than a height of the funnel portion.

For some applications, a distal end of the tube is shaped to define an openable seal.

For some applications, a distal end of the tube does not have an opening.

For some applications, the apparatus further includes a stopper configured to close a distal opening of the tube.

For some applications, the stopper is disposed over the distal opening of the tube.

For some applications, a distal end of the tube is shaped to define a conduit.

There is further provided, in accordance with some applications of the present invention, a method for testing for presence of a particulate selected from the group consisting of: a microorganism, a fungus, a bacteria, a spore, a virus, a mite, a biological cell, a biological antigen, a protein, a protein antigen, and a carbohydrate antigen, the method including:

collecting, in a tube, fluid that potentially contains the particulate;

using a plunger, pushing the fluid through a filter disposed at a location selected from the group consisting of: a distal portion of the tube, and a distal end of the plunger; and subsequently, while the filter is inside the tube, testing for presence of the particulate, by ascertaining if any of the particulate was trapped by the filter.

For some applications, the selected location is the distal portion of the tube, and pushing the fluid includes pushing the fluid out of the tube through a conduit disposed at the distal end of the tube.

For some applications, the plunger is shaped to define at least one compartment, the selected location is the distal end of the plunger, and pushing the fluid includes pushing the fluid into the at least one compartment.

For some applications, the apparatus further includes puncturing the filter before testing for presence of the particulate.

For some applications, the selected location is the distal end of the tube, and puncturing the filter includes using a puncturing element protruding from a distal end of the plunger to puncture the filter.

For some applications, the selected location is the distal end of the plunger and puncturing the filter includes using a puncturing element protruding, in a proximal direction, from the distal end of the tube to puncture the filter.

For some applications, the selected location is the distal end of the tube, and the plunger is configured to rotate with respect to the tube when inside the tube, at least one puncturing element protruding from a distal end of the plunger.

For some applications, the selected location is the distal end of the plunger, and the plunger is configured to rotate with respect to the tube when inside the tube, at least one puncturing element protruding, in a proximal direction, from the distal end of the tube.

For some applications, testing for presence of the particulate includes testing for presence of the particulate while a distal opening of the tube is above a proximal opening of the tube.

For some applications, testing for presence of the particulate includes testing for presence of the particulate while the plunger and tube are resting on a horizontal surface, on a proximal end of the plunger.

For some applications, testing for presence of the particulate includes testing for presence of the particulate while the plunger and tube are resting on a horizontal surface, on a proximal end of the tube.

For some applications, testing for presence of the particulate includes testing for presence of the particulate via a passageway passing through the plunger from a proximal end of the plunger to the distal end of the plunger.

For some applications, testing for presence of the particulate includes applying a particulate-presence-testing-facilitation solution to the filter.

For some applications, the selected location is the distal portion of the tube, the filter is a first filter, a second filter is disposed in the distal end of the tube, and applying the particulate-presence-testing-facilitation solution to the filter includes applying the particulate-presence-testing-facilitation solution to the first filter but not to the second filter, the two filters being separated by (a) a barrier extending in a proximal direction disposed within the tube or (b) a recess defined in the distal end of the tube.

For some applications, the selected location is the distal end of the plunger, the filter is a first filter, a second filter is disposed in the distal end of the plunger, and applying the particulate-presence-testing-facilitation solution to the filter includes applying the particulate-presence-testing-facilitation solution to the first filter but not to the second filter, the two filters being separated by (a) a recess defined in the distal end of the plunger or (b) a barrier protruding in a distal direction from the distal end of the plunger.

For some applications, applying the particulate-presence-testing-facilitation solution to the filter includes applying the particulate-presence-testing-facilitation solution to the filter by passing the particulate-presence-testing-facilitation solution through a conduit at a distal end of the tube.

For some applications, the distal surface of the plunger is disposed at a slant with respect to a longitudinal axis of the plunger, and passing the particulate-presence-testing-facilitation solution through a conduit at a distal end of the tube includes passing the particulate-presence-testing-facilitation solution through a conduit disposed over a higher end of the slanted distal surface of the plunger when a proximal end of the tube or a proximal end of the plunger is resting on a horizontal surface.

For some applications, the plunger is shaped to define at least one plunger lumen, and applying the particulate-presence-testing-facilitation solution to the filter includes applying the particulate-presence-testing-facilitation solution to the filter by passing the particulate-presence-testing-facilitation solution out of the plunger lumen.

For some applications, a proximally-facing distal surface of the tube is disposed at a slant with respect to a lateral wall of the tube, and passing the particulate-presence-testing-facilitation solution out of the plunger lumen includes passing the particulate-presence-testing-facilitation solution out of a plunger lumen disposed over a higher end of the slanted distal surface of the tube, when a distally-facing distal surface of the tube is resting on a horizontal surface.

For some applications,
the particulate includes a microorganism,
the particulate-presence-testing-facilitation solution includes a releasing agent configured to release an antigen from the microorganism, and
testing for presence of the particulate includes testing for presence of the particulate by testing for presence of the antigen.

For some applications, applying the particulate-presence-testing-facilitation solution to the filter includes releasing the particulate-presence-testing-facilitation solution inside the tube by using the plunger to open an enclosed cavity inside of which the particulate-presence-testing-facilitation solution is disposed.

For some applications, applying the particulate-presence-testing-facilitation solution to the filter includes releasing the particulate-presence-testing-facilitation solution inside the tube by opening an enclosed cavity inside of which the particulate-presence-testing-facilitation solution is disposed.

For some applications, using the plunger to push the fluid through the filter includes advancing the plunger at least until the plunger contacts the filter.

For some applications, collecting the fluid in the tube includes collecting gargled fluid in the tube.

For some applications, the gargled fluid includes an element selected from the group consisting of: carbonated water, phosphate buffered saline, pelargonium sidoides extract, tannic acid, balloon flower platycodon grandiflorus, berberine sulfate, S-carboxymethylcysteine, and curcumin.

For some applications, the gargled fluid includes a plurality of elements selected from the group consisting of: carbonated water, phosphate buffered saline, pelargonium sidoides extract, tannic acid, balloon flower platycodon grandiflorus, berberine sulfate, S-carboxymethylcysteine, and curcumin.

For some applications, the gargled fluid is carbonated.

For some applications, a temperature of the gargled fluid is 1-38 degrees Celsius.

For some applications, collecting the fluid in the tube includes collecting biological fluid in the tube.

For some applications, collecting the biological fluid in the tube includes collecting saliva in the tube.

For some applications, collecting the biological fluid in the tube includes collecting blood in the tube.

For some applications, collecting the biological fluid in the tube includes collecting urine in the tube.

For some applications, collecting the biological fluid in the tube includes collecting stool in the tube.

For some applications, collecting the biological fluid in the tube includes collecting gastrointestinal fluid in the tube.

For some applications, collecting the biological fluid in the tube includes collecting bronchoalveolar lavage fluid in the tube.

For some applications, testing for presence of the particulate includes testing for presence of a bacteria.

For some applications, testing for presence of a bacteria includes testing for presence of a streptococcus bacteria.

For some applications, testing for presence of the particulate includes testing for presence of a virus.

For some applications, testing for presence of the particulate includes testing for presence of a biological cell.

For some applications, testing for presence of the biological cell includes testing for presence of a cancerous cell.

For some applications, testing for presence of the particulate includes testing for presence of a pollen spore.

For some applications, testing for presence of the particulate includes testing for presence of a fungus.

For some applications, testing for presence of the particulate includes testing for presence of a mite.

For some applications, the method further includes, before testing for presence of the particulate, using a culture medium to culture the particulate.

For some applications, the method further includes, before testing for presence of the particulate, using a preserving medium to preserve the particulate.

For some applications, ascertaining includes ascertaining using a first protocol, and if no particulate is found to be present, ascertaining using a second protocol.

For some applications, ascertaining using the first protocol includes applying a particulate-presence-testing-facilitation solution to the filter.

For some applications, the selected location is the distal portion of the tube, the method further includes removing the plunger from the tube and subsequently transferring a sample from the distal end of the plunger to a culture media surface, and ascertaining using the second protocol includes ascertaining whether the particulate is on the culture media surface.

For some applications, the method further includes taking a sample from the filter prior to applying the particulate-presence-testing-facilitation solution to the filter.

For some applications, taking the sample from the filter includes swabbing the filter.

For some applications, the selected location is the distal portion of the tube, and swabbing the filter includes swabbing the filter from a proximal end of the plunger through a plunger lumen of the plunger, while the plunger is inside the tube.

For some applications, the selected location is the distal portion of the tube, and taking the sample includes removing the plunger from the tube, and subsequently swabbing the filter from a proximal end of the tube.

For some applications, the selected location is the distal portion of the tube, and swabbing the filter includes swabbing the filter through a conduit in a distal end of the tube.

For some applications, the selected location is the distal end of the plunger, and swabbing the filter includes swabbing the filter from a proximal end of the plunger through a plunger lumen of the plunger.

For some applications, the selected location is the distal end of the plunger, and swabbing the filter includes swabbing the filter through a conduit defined in the distal end of the tube, while the plunger is inside the tube.

For some applications, the method further includes culturing the sample taken from the filter for 2-48 hours, and ascertaining using the second protocol includes ascertaining if any of the particulate is present in the sample after the 2-48 hours.

For some applications, ascertaining if any of the particulate is present in the sample includes applying a particulate-presence-testing-facilitation solution to the sample after the 2-48 hours.

For some applications, culturing the sample includes plating the sample on a culture media surface, and ascertaining if any of the particulate is present in the sample includes ascertaining whether the particulate is on the culture media surface after the 2-48 hours.

There is further provided, in accordance with some applications of the present invention, apparatus including:

a tube;

a plunger sized and shaped to be advanceable within the tube while sealably contacting the tube;

an insert disposed within a distal portion of the tube and not fixed to the plunger; and a filter coupled to a proximally-facing surface of the insert.

For some applications, the insert is shaped to define (a) an at least partially distally-facing opening therein, and (b) a passage from the proximally-facing surface of the insert to the at least partially distally-facing opening.

For some applications, the insert is further shaped to define a plurality of grooves in the proximally-facing surface of the insert, respective spaces within the grooves being in fluid communication with the passage.

There is further provided, in accordance with some applications of the present invention, apparatus including:

a tube shaped to define a plurality of openings at a distal end thereof;

a plunger sized and shaped to be advanceable within the tube while sealably contacting the tube; and a filter disposed within a distal portion of the tube, proximal to the plurality of openings.

For some applications, a total area of the plurality of openings is between 10% and 90% of a cross-sectional area of the distal end of the tube.

For some applications, the total area of the plurality of openings is between 10% and 80% of the cross-sectional area of the distal end of the tube.

For some applications, the total area of the plurality of openings is between 10% and 70% of the cross-sectional area of the distal end of the tube.

For some applications, the total area of the plurality of openings is between 20% and 70% of the cross-sectional area of the distal end of the tube.

There is further provided, in accordance with some applications of the present invention, apparatus including:

a tube containing a medium selected from the group consisting of: a culture medium configured to culture a microorganism, a culture medium configured to culture a fungus, a culture medium configured to culture a bacteria, a culture medium configured to culture a spore, a culture medium configured to culture a mite, a culture medium configured to culture a biological cell, a culture medium configured to culture a virus, a releasing medium configured to release an antigen from a microorganism, a releasing medium configured to release an antigen from a protein, a releasing medium configured to release an antigen from a carbohydrate, a heating medium configured to undergo an exothermic reaction, a salt, a preserving medium configured to preserve a microorganism, a preserving medium configured to preserve a fungus, a preserving medium configured to preserve a bacteria, a preserving medium configured to preserve a biological cell, a preserving medium configured to preserve a mite, a preserving medium configured to preserve a spore, and a preserving medium configured to preserve a virus;

a filter disposed within a distal portion of the tube; and a plunger sized and shaped to be advanceable within the tube while sealably contacting the tube.

For some applications, the medium is disposed proximally to the filter.

For some applications, the medium is disposed distally to the filter.

For some applications, the apparatus further includes:

a heating element configured to heat the tube; and a kit in which the heating element and tube are disposed.

For some applications, the heating element includes a chemical heating element.

For some applications, the heating element includes an electric heating element.

There is further provided, in accordance with some applications of the present invention, a method including:

placing a fluid into a tube containing a medium selected from the group consisting of: a culture medium configured to culture a microorganism, a culture medium configured to culture a fungus, a culture medium configured to culture a bacteria, a culture medium configured to culture a spore, a culture medium configured to culture a mite, a culture medium configured to culture a biological cell, a culture medium configured to culture a virus, a releasing medium configured to release an antigen from a microorganism, a releasing medium configured to release an antigen from a protein, a releasing medium configured to release an antigen from a carbohydrate, a heating medium configured to undergo an exothermic reaction, a salt, a preserving medium configured to preserve a microorganism, a preserving medium configured to preserve a fungus, a preserving medium configured to preserve a bacteria, a preserving medium configured to preserve a biological cell, a preserving medium configured to preserve a mite, a preserving medium configured to preserve a spore, and a preserving medium configured to preserve a virus; and using a plunger to push the fluid through a filter disposed at a location selected from the group consisting of: a distal portion of the tube, and a distal end of the plunger.

For some applications, the method further including heating the tube.

For some applications, the method further including, following the pushing of the fluid through the filter and while the filter is inside the tube, testing for presence of a particulate by ascertaining if any of the particulate was trapped by the filter, the particulate being selected from the group consisting of: a microorganism, a fungus, a bacteria, a spore, a virus, a mite, a biological cell, a biological antigen, a protein, a protein antigen, and a carbohydrate antigen.

There is further provided, in accordance with some applications of the present invention, apparatus including:

a tube;

a plunger sized and shaped to be advanceable within the tube;

a first filter disposed within a distal portion of the tube, the first filter having a pore size of between 0.5 and 100 microns; and a second filter having a pore size of between 0.1 and 20 microns.

For some applications, the pore size of the first filter is larger than the pore size of the second filter.

For some applications, the second filter is disposed distally to the first filter.

For some applications, the first filter has a pore size of between 0.5 and 20 microns, and the second filter has a pore size of between 0.1 microns and 1 micron.

For some applications, the first filter has a pore size of between 10 and 100 microns, and the second filter has a pore size of between 1 micron and 10 microns.

For some applications, the first filter has a pore size of between 5 and 25 microns, and the second filter has a pore size of between 1 micron and 20 microns.

There is further provided, in accordance with some applications of the present invention, apparatus including:

a tube having a funnel-shaped proximal opening; and a plunger sized and shaped to be advanceable within the tube while sealably contacting the tube, the tube and plunger being configured such that, following the plunger being maximally advanced within the tube, the plunger is withdrawable from the tube only by use of a tool or by breaking a portion of the apparatus.

For some applications, a proximal end of the plunger is not proximal to a proximal end of the tube, when the plunger is maximally advanced within the tube.

For some applications, the apparatus further includes a locking mechanism configured to lock the plunger inside the tube following the plunger being maximally advanced within the tube.

There is further provided, in accordance with some applications of the present invention, apparatus including:

a tube; and a plunger sized and shaped to be advanceable within the tube while sealably contacting the tube, a distal end of the plunger being shaped to define at least one enclosed cavity containing a particulate-presence-testing-facilitation solution, the enclosed cavity being configured to open upon the plunger being moved within the tube, and the particulate selected from the group consisting of: a microorganism, a spore, a virus, a mite, a biological cell, a biological antigen, a protein, a protein antigen, and a carbohydrate antigen.

There is further provided, in accordance with some applications of the present invention, apparatus including:

a tube; and a plunger sized and shaped to be advanceable within the tube while sealably contacting the tube, a distal end of the plunger being shaped to define at least one enclosed cavity containing a particulate-presence-testing-facilitation solution, the enclosed cavity being configured to open while the plunger is inside the tube, and the particulate selected from the group consisting of: a microorganism, a spore, a virus, a mite, a biological cell, a biological antigen, a protein, a protein antigen, and a carbohydrate antigen.

For some applications, in accordance with some applications of the present invention, apparatus including:

a tube; and a plunger sized and shaped to be advanceable within the tube while sealably contacting the tube, a wall of the tube being shaped to define at least one enclosed cavity containing a particulate-presence-testing-facilitation solution, the enclosed cavity being configured to open upon the plunger being moved within the tube, and the particulate selected from the group consisting of: a microorganism, a fungus, a bacteria, a spore, a virus, a mite, a biological cell, a biological antigen, a protein, a protein antigen, and a carbohydrate antigen.

There is further provided, in accordance with some applications of the present invention, apparatus including:

a tube; and a plunger sized and shaped to be advanceable within the tube while sealably contacting the tube, a wall of the tube being shaped to define at least one enclosed cavity containing a particulate-presence-testing-facilitation solution, the enclosed cavity being configured to open, and the particulate selected from the group consisting of: a microorganism, a fungus, a bacteria, a spore, a virus, a mite, a biological cell, a biological antigen, a protein, a protein antigen, and a carbohydrate antigen.

There is further provided, in accordance with some applications of the present invention, apparatus including:

a tube; and a plunger sized and shaped to be advanceable within the tube while sealably contacting the tube, the plunger being shaped to define at least one plunger lumen containing a particulate-presence-testing-facilitation solution, the particulate selected from the group consisting of: a microorganism, a fungus, a bacteria, a spore, a virus, a mite, a biological cell, a biological antigen, a protein, a protein antigen, and a carbohydrate antigen.

There is further provided, in accordance with some applications of the present invention, apparatus including:

a tube;

a filter disposed within a distal portion of the tube;

a plunger sized and shaped to be advanceable within the tube while sealably contacting the tube; and a puncturing element protruding from a distal end of the plunger, the puncturing element being configured to puncture the filter upon the plunger being advanced to the filter.

There is further provided, in accordance with some applications of the present invention, a method for testing for presence of a particulate selected from the group consisting of: a microorganism, a fungus, a bacteria, a spore, a virus, a mite, a biological cell, a biological antigen, a protein, a protein antigen, and a carbohydrate antigen, the method including:

collecting, in a tube having a filter, fluid that potentially contains the particulate;

passing the fluid through the filter; and subsequently, while the filter is inside the tube, testing for presence of the particulate, by ascertaining if any of the particulate was trapped by the filter.

For some applications, ascertaining includes ascertaining using a first protocol, and if no particulate is found to be present, ascertaining using a second protocol.

For some applications, ascertaining using the first protocol includes applying a particulate-presence-testing-facilitation solution to the filter.

For some applications, the method further includes taking a sample from the filter prior to applying the particulate-presence-testing-facilitation solution to the filter.

For some applications, taking the sample from the filter includes swabbing the filter.

For some applications, swabbing the filter includes swabbing the filter from a proximal end of the tube.

For some applications, swabbing the filter includes swabbing the filter through a conduit in a distal end of the tube.

For some applications, the method further includes culturing the sample taken from the filter for 2-48 hours, and wherein ascertaining using the second protocol includes ascertaining if any of the particulate is present in the sample after the 2-48 hours.

For some applications, ascertaining if any of the particulate is present in the sample includes applying a particulate-presence-testing-facilitation solution to the sample after the 2-48 hours.

For some applications, culturing the sample includes plating the sample on a culture media surface, and ascertaining if any of the particulate is present in the sample includes ascertaining whether any of the particulate is on the culture media surface after the 2-48 hours.

For some applications, collecting the fluid in the tube includes collecting gargled fluid in the tube.

For some applications, the gargled fluid includes an element selected from the group consisting of: carbonated water, phosphate buffered saline, pelargonium sidoides extract, tannic acid, balloon flower platycodon grandiflorus, berberine sulfate, S-carboxymethylcysteine, and curcumin.

For some applications, the gargled fluid includes a plurality of elements selected from the group consisting of: carbonated water, phosphate buffered saline, pelargonium sidoides extract, tannic acid, balloon flower platycodon grandiflorus, berberine sulfate, S-carboxymethylcysteine, and curcumin.

For some applications, the gargled fluid is carbonated.

For some applications, a temperature of the gargled fluid is 1-38 degrees Celsius.

There is further provided, in accordance with some applications of the present invention, apparatus including:

a tube having proximal and distal ends;

a barrier extending in a proximal direction, disposed within the tube;

a plunger sized and shaped to be advanceable within the tube while sealably contacting the tube, a distal end of the plunger shaped to define a recess into which the barrier fits upon the plunger being advanced to the barrier; and two filters disposed at a location selected from the group consisting of: the distal end of the tube, and a distal end of the plunger.

For some applications, the selected location is the distal end of the tube, and the two filters are separated by the barrier.

For some applications, the selected location is the distal end of the plunger, and the two filters are separated by the recess defined in the distal end of the plunger.

For some applications, the selected location is the distal end of the tube, and the apparatus further includes at least two puncturing elements protruding from the distal end of the plunger, the puncturing elements being configured to puncture the two filters, respectively, upon the plunger being advanced to the filters.

For some applications, the selected location is the distal end of the plunger, and the apparatus further includes at least two puncturing elements protruding in a proximal direction from the distal end of the tube, the puncturing elements being configured to puncture the two filters respectively upon the plunger being advanced to the barrier.

For some applications, the selected location is the distal end of the tube, and the distal end of the tube is shaped to define at least two conduits, the conduits being configured to align with the two filters respectively.

For some applications, the selected location is the distal end of the plunger, and the distal end of the tube is shaped to define at least two conduits, the conduits being configured to align with the two filters respectively when the plunger is inside the tube.

For some applications, the plunger is shaped to define a plunger lumen containing a particulate-presence-testing-facilitation solution, an opening of the plunger lumen being arranged to align with one of the filters and not to simultaneously align with the other filter, such that the particulate-presence-testing-facilitation solution is applied to only the one of the filters.

For some applications, one of the two filters is at least 25% larger than the other.

For some applications, a culture medium is disposed on at least one of the filters.

For some applications, no culture medium is disposed on at least one of the filters.

For some applications, the plunger, once maximally advanced to the barrier, is configured to prevent a particulate-presence-testing-facilitation solution that is applied to one filter from contacting the other filter.

For some applications, a height of the barrier extending in a distal to proximal direction is less than 90% of a height of the tube.

For some applications, the height of the barrier is less than a height of the tube that corresponds to a volume of 10 cc in the tube, measured from the distal end of the tube.

For some applications, the height of the barrier is less than a height of the tube that corresponds to a volume of 5 cc in the tube, measured from the distal end of the tube.

For some applications, the height of the barrier is less than a height of the tube that corresponds to a volume of 1 cc in the tube, measured from the distal end of the tube For some applications, a distal portion of the tube is (a) shaped to define at least one enclosed cavity containing a particulate-presence-testing-facilitation solution, and (b) configured such that the particulate-presence-testing-facilitation solution in the cavity is applied to only one filter.

For some applications, a wall of the enclosed cavity is configured to open and release the particulate-presence-testing-facilitation solution to the only one filter.

For some applications, a wall of the enclosed cavity is configured to open and release the particulate-presence-testing-facilitation solution to the only one filter following initiation of distal motion of the plunger in the tube.

For some applications, the two filters are a first filter and a second filter, the barrier is a first barrier, the recess is a first recess, and the first filter is separated from the second filter by the first barrier or by the first recess, (a) the apparatus further including a second barrier extending in a proximal direction, disposed within the tube, (b) the distal end of the plunger being further shaped to define a second recess into which the second barrier fits upon the plunger being advanced to the barriers, and (c) the apparatus further including a third filter disposed at a location selected from the group consisting of: the distal end of the tube, and the distal end of the plunger, the third filter separated from the second filter by the second barrier or by the second recess.

For some applications, a culture medium is disposed on at least one of the filters.

For some applications, the plunger, once maximally advanced to the barriers, is configured to prevent a particulate-presence-testing-facilitation solution that is applied to one filter from contacting any other filter.

For some applications, at least one of the filters is at least 25% larger than at least one other filter.

For some applications, the selected location is the distal end of the tube, and the apparatus further includes at least three puncturing elements protruding from a distal end of the plunger, the puncturing elements being configured to puncture the respective filters, upon the plunger being advanced to the filters.

For some applications, the selected location is the distal end of the plunger, and the apparatus further includes at least three puncturing elements protruding in a proximal direction from the distal end of the tube, the puncturing elements being configured to puncture the respective filters, upon the plunger being advanced to the barriers.

For some applications, the selected location is the distal end of the tube, and the distal end of the tube is shaped to define at least three conduits, the conduits being configured to align with the respective filters.

For some applications, the selected location is the distal end of the plunger, and the distal end of the tube is shaped to define at least three conduits, the conduits being configured to align with the respective filters, when the plunger is in the tube.

There is further provided, in accordance with some applications of the present invention, apparatus including:

a tube having proximal and distal ends, the distal end of the tube shaped to define a recess;

a plunger sized and shaped to be advanceable within the tube while sealably contacting the tube;

a barrier protruding in a distal direction from a distal end of the plunger, configured to fit into the recess of the tube upon the plunger being advanced to the recess; and two filters disposed at a location selected from the group consisting of: the distal end of the tube, and the distal end of the plunger.

For some applications, the selected location is the distal end of the tube, and the two filters are separated by the recess defined in the distal end of the tube.

For some applications, the selected location is the distal end of the plunger, and the two filters are separated by the barrier protruding from the distal end of the plunger.

For some applications, the selected location is the distal end of the tube, and the apparatus further includes at least two puncturing elements protruding from the distal end of the plunger, the puncturing elements being configured to puncture the two filters, respectively, upon the plunger being advanced to the filters.

For some applications, the selected location is the distal end of the plunger, and the apparatus further includes at least two puncturing elements protruding in a proximal direction from the distal end of the tube, the puncturing elements being configured to puncture the two filters respectively upon the plunger being advanced to the recess.

For some applications, the selected location is the distal end of the tube, and the distal end of the tube is shaped to define at least two conduits, the conduits being configured to align with the two filters respectively.

For some applications, the selected location is the distal end of the plunger, and the distal end of the tube is shaped to define at least two conduits, the conduits being configured to align with the two filters respectively when the plunger is inside the tube.

For some applications, the plunger is shaped to define at least one plunger lumen containing a particulate-presence-testing-facilitation solution, an opening of the plunger lumen being arranged to align with one of the filters and not to simultaneously align with the other filter, such that the particulate-presence-testing-facilitation solution is applied to only the one of the filters.

For some applications, one of the two filters is at least 25% larger than the other.

For some applications, a culture medium is disposed on at least one of the filters.

For some applications, no culture medium is disposed on at least one of the filters.

For some applications, the plunger, once maximally advanced to the recess, is configured to prevent a particulate-presence-testing-facilitation solution that is applied to one filter from contacting the other filter.

For some applications, a distal portion of the tube is (a) shaped to define at least one enclosed cavity containing a particulate-presence-testing-facilitation solution, and (b) configured such that the particulate-presence-testing-facilitation solution in the cavity is applied to only one filter.

For some applications, a wall of the enclosed cavity is configured to open and release the particulate-presence-testing-facilitation solution to the only one filter.

For some applications, a wall of the enclosed cavity is configured to open and release the particulate-presence-testing-facilitation solution to the only one filter following initiation of distal motion of the plunger in the tube.

For some applications, the two filters are a first filter and a second filter, the barrier is a first barrier, the recess is a first recess, and the first filter separated from the second filter by the first recess or by the first barrier, (a) the apparatus further including a second barrier protruding in a distal direction from the distal end of the plunger, (b) the distal end of the tube being further shaped to define a second recess into which the second barrier fits upon the plunger being advanced to the recess, and (c) the apparatus further including a third filter disposed at a location selected from the group consisting of: the distal end of the tube, and the distal end of the plunger, the third filter being separated from the second filter by the second recess or by the second protrusion.

For some applications, a culture medium is disposed on at least one of the filters.

For some applications, the plunger, once maximally advanced to the recesses, is configured to prevent a particulate-presence-testing-facilitation solution that is applied to one filter from contacting any other filter.

For some applications, at least one of the filters is at least 25% larger than at least one other filter.

For some applications, the selected location is the distal end of the tube, and the apparatus further includes at least three puncturing elements protruding from a distal end of the plunger, the puncturing elements being configured to puncture the respective filters, upon the plunger being advanced to the filters.

For some applications, the selected location is the distal end of the plunger, and the apparatus further includes at least three puncturing elements protruding in a proximal direction from the distal end of the tube, the puncturing elements being configured to puncture the respective filters, upon the plunger being advanced to the recesses.

For some applications, the selected location is the distal end of the tube, and the distal end of the tube is shaped to define at least three conduits, the conduits being configured to align with the respective filters.

For some applications, the selected location is the distal end of the plunger, and the distal end of the tube is shaped to define at least three conduits, the conduits being configured to align with the respective filters, when the plunger is in the tube.

There is further provided, in accordance with some applications of the present invention apparatus including:

a tube, a distal surface of the tube being oriented at a slant with respect to a lateral wall of the tube;

a plunger sized and shaped to be advanceable within the tube while sealably contacting the tube, a distal surface of the plunger being oriented at a slant with respect to a longitudinal axis of the plunger;

the tube and plunger being configured such that the slant of the distal surface of the plunger aligns with the slant of the distal surface of the tube at at least one rotational orientation of the tube with respect to the plunger; and a filter disposed at a location selected from the group consisting of: a distal end of the tube, and a distal end of the plunger.

For some applications, the distal surface of the tube is shaped to define a cone.

For some applications, a distal end of the tube is shaped to define at least two conduits disposed at a higher end of the slant of the tube and at a lower end of the slant of the tube, respectively, when a proximal end of the tube or a proximal end of the plunger is resting on a horizontal surface.

For some applications, a proximally-facing distal surface of the tube is oriented at a slant with respect to a lateral wall of the tube, and the plunger is shaped to define at least two plunger lumens disposed over a higher end of the slant of the tube and over a lower end of the slant of the tube, respectively, when a distally-facing distal end of the tube is resting on a horizontal surface.

For some applications, the tube and plunger are shaped to have rotational asymmetry, such that during at least a portion of the advancement of the plunger within the tube, the plunger is advanceable within the tube in only a single orientation of the plunger with respect to the tube.

For some applications, the tube and plunger include corresponding interlockable pieces such that the plunger is advanceable within the tube in only a single orientation of the plunger with respect to the tube.

There is further provided, in accordance with some applications of the present invention, apparatus including:
a plunger; and
a tube,
the plunger being sized and shaped to be advanceable within the tube while sealably contacting the tube, and
a wall of the tube being shaped to define at least one enclosed cavity containing a particulate-presence-testing-facilitation solution and a gas above atmospheric pressure.

For some applications, the apparatus further includes a filter disposed at a location selected from the group consisting of: a distal end of the tube, and a distal end of the plunger.

For some applications, the selected location is the distal end of the tube, and the enclosed cavity is configured to open such that the particulate-presence-testing-facilitation solution is forced out of the enclosed cavity and applied to the filter.

For some applications, the selected location is the distal end of the tube, and the enclosed cavity is configured to open following initiation of distal motion of the plunger in the tube, such that the particulate-presence-testing-facilitation solution is forced out of the enclosed cavity and applied to the filter.

There is further provided, in accordance with some applications of the present invention, apparatus including:
a plunger,
a wall of the plunger being shaped to define at least one enclosed cavity containing a particulate-present-testing-facilitation solution and a gas above atmospheric pressure; and
a tube,
the plunger being sized and shaped to be advanceable within the tube while sealably contacting the tube.

For some applications, the apparatus further includes a filter disposed at a location selected from the group consisting of: a distal end of the tube, and a distal end of the plunger.

For some applications, the selected location is the distal end of the plunger and the enclosed cavity is configured to open following initiation of distal motion of the plunger in the tube, such that the particulate-presence-testing-facilitation solution is forced out of the enclosed cavity and applied to the filter.

There is further provided, in accordance with some applications of the present invention, apparatus including:
a tube, closed at a distal end thereof;
a filter disposed within the tube, the tube being shaped to define a fluid-collection compartment distal to the filter; and
a plunger sized and shaped to be advanceable within the tube while sealably contacting the tube, the plunger being arranged to push a fluid through the filter and into the fluid-collection compartment; and
a support which is (a) shaped to define one or more openings, (b) disposed within the tube, and (c) in contact with the filter.

For some applications, the support is disposed proximal to the filter within the tube, and is configured to support the filter during withdrawal of the plunger in a proximal direction.

For some applications, the support is disposed distal to the filter within the tube, and is configured to support the filter during the pushing of the fluid through the filter.

For some applications, the support is positioned to inhibit distal advancement of the plunger past the filter.

For some applications, a wall of the compartment is shaped to define a pressure-release hole, such that air pressure in the compartment generated by advancing the plunger is released through the pressure-release hole.

For some applications, a diameter of the pressure-release hole is 50-1500 microns.

For some applications, the pressure-release hole is disposed above a volume of 2 cc of the compartment when the distal end of the tube is resting on a horizontal surface.

For some applications, the tube is shaped to define a flat external, surface-contact portion which is shaped to contact a horizontal surface when the distal end of the tube is resting on the horizontal surface, the surface-contact portion having a diameter at least equal to a diameter of the filter.

There is further provided, in accordance with some applications of the present invention, a method for testing for presence of a particulate selected from the group consisting of: a microorganism, a fungus, a bacteria, a spore, a virus, a mite, a biological cell, a biological antigen, a protein, a protein antigen, and a carbohydrate antigen, the method including:
collecting, in a tube, fluid that potentially contains the particulate;
using a plunger, pushing the fluid through a filter, disposed within the tube, into a fluid-collection compartment distal to the filter; and
subsequently, while the filter is inside the tube, testing for presence of the particulate, by ascertaining if any of the particulate was trapped by the filter.

For some applications, collecting the fluid in the tube includes collecting gargled fluid in the tube.

For some applications, the gargled fluid includes an element selected from the group consisting of: carbonated water, phosphate buffered saline, pelargonium sidoides extract, tannic acid, balloon flower platycodon grandiflorus, berberine sulfate, S-carboxymethylcysteine, and curcumin.

For some applications, the gargled fluid includes a plurality of elements selected from the group consisting of: carbonated water, phosphate buffered saline, pelargonium sidoides extract, tannic acid, balloon flower platycodon grandiflorus, berberine sulfate, S-carboxymethylcysteine, and curcumin.

For some applications, the gargled fluid is carbonated.

For some applications, a temperature of the gargled fluid is 1-38 degrees Celsius.

There is further provided, in accordance with some applications of the present invention, apparatus including:
a tube;
a plunger sized and shaped to be advanceable within the tube while sealably contacting the tube;
a filter; and
at least one puncturing element,
the filter and puncturing element being disposed such that:
  (a) the filter is disposed in a distal portion of the tube, and the puncturing element protrudes in a distal direction from a distal end of the plunger, or
  (b) the filter is disposed at a distal end of the plunger, and the puncturing element protrudes in a proximal direction from a distal end of the tube.

For some applications, the at least one puncturing element is configured to puncture the filter upon the plunger being maximally advanced within the tube.

For some applications, the at least one puncturing element is configured to tear the filter upon rotation of the plunger, when the plunger is maximally advanced within the tube.

There is further provided, in accordance with some applications of the present invention, a method for testing for presence of a particulate selected from the group consisting of: a microorganism, a fungus, a bacteria, a spore, a virus, a mite, a biological cell, a biological antigen, a protein, a protein antigen, and a carbohydrate antigen, the method including:

collecting, in a tube, fluid that potentially contains the particulate;

pushing the fluid through a filter disposed within a distal portion of the tube;

tearing the filter while the filter is inside the tube; and subsequently, while the filter is inside the tube, testing for presence of the particulate, by ascertaining if any of the particulate was trapped by the filter by applying a particulate-presence-testing-facilitation solution to the filter.

For some applications, pushing the fluid includes pushing the fluid using a plunger in the tube.

For some applications, tearing the filter includes rotating the plunger with respect to the tube when the plunger is maximally advanced within the tube, at least one puncturing element protruding from a distal end of the plunger.

For some applications, tearing the filter includes rotating the plunger with respect with respect to the tube when the plunger is maximally advanced within the tube.

For some applications, the filter is disposed on a distal end of the plunger and tearing the filter includes rotating the plunger with respect to the tube when the plunger is maximally advanced within the tube, at least one puncturing element protruding in a proximal direction from a distal end of the tube.

For some applications, collecting the fluid in the tube includes collecting gargled fluid in the tube.

For some applications, the gargled fluid includes an element selected from the group consisting of: carbonated water, phosphate buffered saline, pelargonium sidoides extract, tannic acid, balloon flower platycodon grandiflorus, berberine sulfate, S-carboxymethylcysteine, and curcumin.

For some applications, the gargled fluid includes a plurality of elements selected from the group consisting of: carbonated water, phosphate buffered saline, pelargonium sidoides extract, tannic acid, balloon flower platycodon grandiflorus, berberine sulfate, S-carboxymethylcysteine, and curcumin.

For some applications, the gargled fluid is carbonated.

For some applications, a temperature of the gargled fluid is 1-38 degrees Celsius.

There is further provided, in accordance with some applications of the present invention, apparatus including:
a plunger; and
a tube,
the plunger being sized and shaped to be advanceable within the tube while sealably contacting the tube, and
the tube and plunger being shaped to have rotational asymmetry such that during at least a portion of the advancement of the plunger within the tube, the plunger is advanceable within the tube in only a single rotational orientation of the plunger with respect to the tube.

There is further provided, in accordance with some applications of the present invention, apparatus including:
a plunger; and
a tube,
the tube and plunger including corresponding interlockable pieces such that the plunger is advanceable within the tube in only a single rotational orientation of the plunger with respect to the tube.

There is further provided, in accordance with some applications of the present invention, apparatus including:
a tube;
a plunger;
a protrusion; and
threading,
the protrusion and threading being disposed such that:
(a) the threading is disposed on the inside of at least a portion of the tube and the protrusion protrudes outwards from a wall of the plunger, or
(b) the threading is disposed on the outside of at least a portion of the plunger and the protrusion protrudes inwards from a wall of the tube,
the protrusion being configured to slidably engage the threading such that the plunger is advanceable within the tube by rotation of the plunger with respect to the tube.

There is further provided, in accordance with some applications of the present invention, apparatus including:
a tube;
a plunger;
a protrusion; and
threading,
the protrusion and threading being disposed such that:
(a) the threading is disposed on the inside of at least a portion of the tube and the protrusion protrudes outwards from a wall of the plunger, or
(b) the threading is disposed on the outside of at least a portion of the plunger and the protrusion protrudes inwards from a wall of the tube,
a pitch of the threading at a first location being different from the pitch of the threading at a second location.

For some applications, the pitch of the threading at the second location is greater than the pitch of the threading at the first location, the second location being distal to the first location.

For some applications, the pitch of the threading at the second location is less than the pitch of the threading at the first location, the second location being distal to the first location.

There is further provided, in accordance with some applications of the present invention, apparatus including:
a tube;
a plunger;
a protrusion; and
threading,
the protrusion and threading being disposed such that:
(a) the threading is disposed on the inside of at least a portion of the tube and the protrusion protrudes outwards from a wall of the plunger, or
(b) the threading is disposed on the outside of at least a portion of the plunger and the protrusion protrudes inwards from a wall of the tube, and
(c) a portion of the threading closest to a distal end of the tube or plunger is perpendicular to a line, wherein the line is parallel to a longitudinal axis of the tube,
wherein:
(a) the protrusion is configured to slidably engage the threading such that the plunger is advanceable within the tube by rotation of the plunger with respect to the tube, and
(b) the protrusion is configured to engage the perpendicular portion of the threading when the plunger is maximally advanced within the tube, such that the plunger can rotate with respect to the tube without further inhibition by the threading.

There is further provided, in accordance with some applications of the present invention, a method for testing for presence of a particulate selected from the group consisting of: a microorganism, a fungus, a bacteria, a spore, a virus, a mite, a biological cell, a biological antigen, a protein, a protein antigen, and a carbohydrate antigen, the method including:

collecting, in a tube, fluid that potentially contains the particulate;

using a plunger, pushing the fluid through a filter disposed at a location selected from the group consisting of: a distal portion of the tube, and a distal end of the plunger;

removing the plunger from the tube and transferring a sample from the distal end of the plunger to a culture media surface; and subsequently, ascertaining if any of the particulate is on the culture media surface.

There is further provided, in accordance with some applications of the present invention, apparatus including:

a tube;

a plunger sized and shaped to be advanceable within the tube while sealably contacting the tube; and a filter disposed at a location selected from the group consisting of: a distal portion of the tube, and a distal end of the plunger, the distal end of the plunger and the distal end of the tube being configured to tear the filter upon the plunger being maximally advanced within the tube and rotated with respect to the tube.

The present invention will be more fully understood from the following detailed description of applications thereof, taken together with the drawings, in which:

BRIEF DESCRIPTION OF THE DRAWINGS

FIGS. 11A-B are schematic illustrations of a configuration of the apparatus for testing for presence of a particulate in a fluid, in accordance with some applications of the present invention;

FIGS. 14A-D are schematic illustrations of a tube and a plunger having rotational asymmetry, in accordance with some applications of the present invention;

DETAILED DESCRIPTION OF APPLICATIONS

Figure 1:
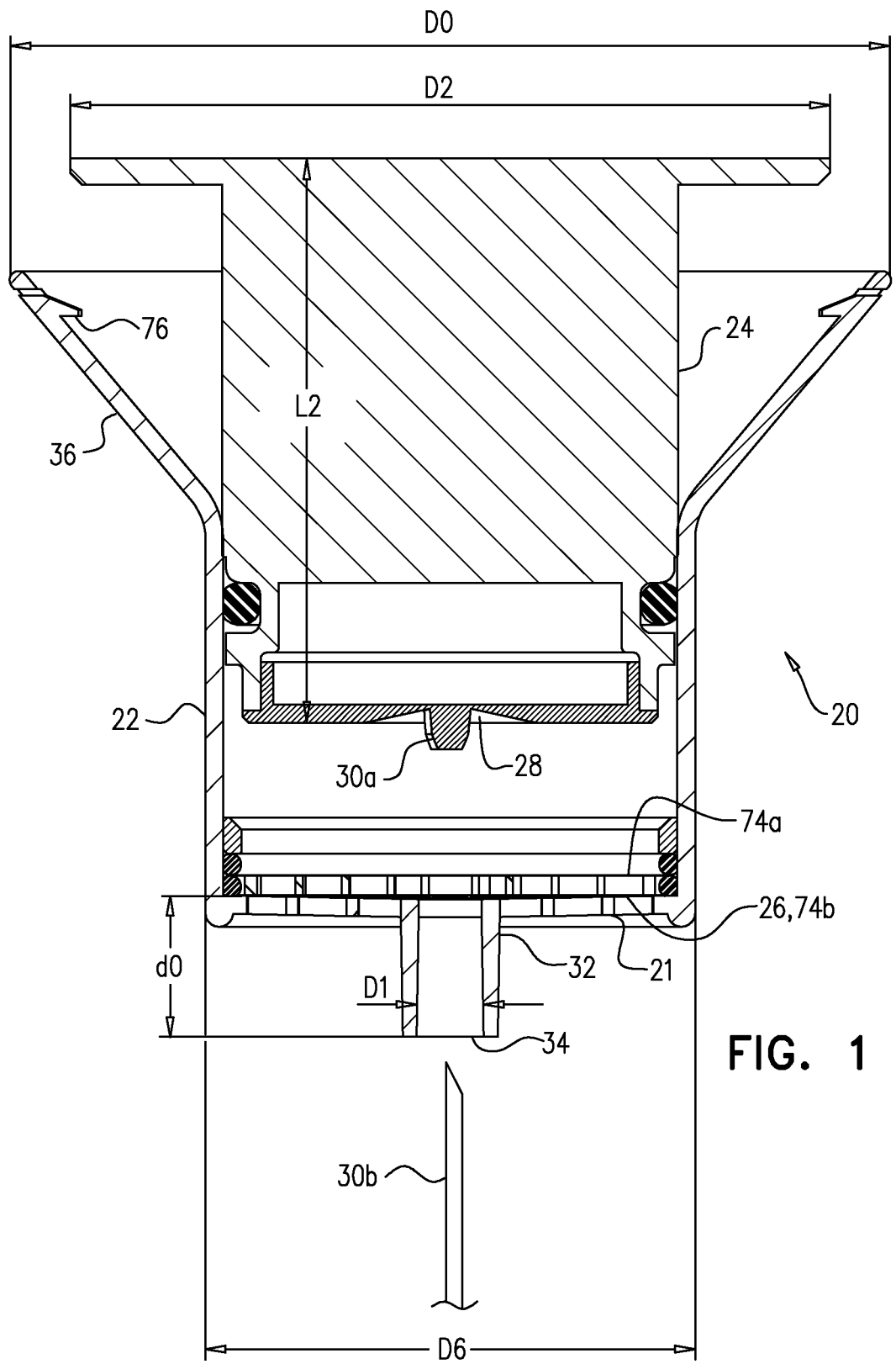
FIGS. 1-7 are schematic illustrations of apparatus for testing for presence of a particulate in a fluid, in accordance with some applications of the present invention.

Reference is made to FIG. 1, which is a schematic illustration of apparatus 20 for testing for presence of a particulate in a fluid, in accordance with some applications of the present invention. Apparatus 20 comprises a tube 22 and a plunger 24, plunger 24 being sized and shaped to be advanceable within tube 22 while sealably contacting the tube. A proximally-facing surface 21 at a distal end of the tube inhibits advancement of the plunger.

Fluid that potentially contains the particulate is collected in the tube. Using the plunger, the fluid is pushed through a filter 26 disposed within a distal portion of the tube. (It is noted that in the context of the claims and specification of the present application, the term "proximal" refers to the top of the apparatus as depicted in FIG. 1, while the term "distal" refers to the bottom. For example, a user of apparatus 20 would place his thumb on the proximal end of plunger 24, and using the plunger, would push fluid out of the distal end of tube 22.) Typically, the plunger is advanced at least until the plunger contacts the filter. Filter 26 allows for passage of the fluid therethrough, but does not allow for passage of at least some (e.g., a substantial portion) of the particulate. Consequently, following the pushing of the fluid through the filter, the filter may be tested for presence of the particulate, i.e., the presence of the particulate may be tested for by ascertaining if any of the particulate was trapped by the filter. Typically, the filter is tested for presence of the particulate while the filter is inside the tube.

Types of fluid that may be collected in tube 22 include gargled fluid and/or biological fluid such as saliva. For example, a patient may gargle a saline fluid and subsequently spit the gargled fluid, perhaps along with some saliva, into the tube. (Alternatively, e.g., for juvenile patients who cannot gargle, saliva may be collected without any gargled fluid.) Other types of biological fluid that may be collected in tube 22 include blood (e.g., diluted blood), urine, stool (e.g., diluted stool), gastrointestinal (GI) fluid, and bronchoalveolar lavage fluid. Types of particulates that may be tested for include a microorganism (e.g., a parasite), a fungus, a bacteria, a spore (e.g., a pollen spore), a virus, a mite, a biological cell (e.g., a cancerous cell), a biological antigen, a protein, a protein antigen, and a carbohydrate antigen.

For example, using apparatus 20:

(a) Gargled fluid may be tested for presence of a streptococcus bacteria, as further described hereinbelow.

(b) Diluted blood may be tested for presence of an intracellular or extracellular pathogen (e.g. plasmodium falciparum, a parasite causing malaria, or a blood-borne streptococcus bacteria), or cancerous cells.

(c) Urine may be tested for a urinary tract pathogen.

(d) Diluted stool may be tested for an enteric pathogen (e.g., salmonella).

(e) GI fluid (e.g., GI fluid obtained via a nasogastric or endoscopic tube) may be tested for a pathogen, e.g., giardia.

(f) Aspirated fluid may be tested for presence of cancerous cells.

Typically, the gargle fluid includes carbonated water, phosphate buffered saline, pelargonium sidoides extract, tannic acid, balloon flower platycodon grandiflorus, berberine sulfate, S-carboxymethylcysteine, curcumin, or any combination thereof. In some applications, the gargle fluid is carbonated. Typically, the temperature of the gargle fluid is 1-38 degrees Celsius.

Typically, a volume of the tube is at least 1 mL and/or less than 70 mL, e.g., between 1 and 8 mL, between 8 and 15 mL, between 15 and 30 mL, or between 30 and 70 mL. In some applications, the tube does not comprise a Luer lock or any other type of needle-coupling mechanism.

In some applications, the plunger and tube are shaped to provide an empty volume proximal to surface 21 of at least 0.03 and/or less than 5 mL (e.g., 0.03-1 mL) when the plunger is maximally advanced within the tube. For example, the distal end of the plunger may be shaped to define a distally-facing cavity 28 (e.g., a "dimple") therein, cavity 28 providing at least part of the empty volume. The empty volume, which may be proximal and/or distal to the filter, facilitates the testing of the filter for the particulate, by providing a "testing area" in fluid continuity with the filter. For example, when conducting a rapid strep test, it is typically necessary to apply the A and B solution to the filter, i.e., place the A and B solution in contact with the filter, such that the strep A carbohydrate antigen may be drawn out from the trapped bacteria and into the solution. The empty volume provides an area in fluid continuity with the filter in which the A and B solution may collect, and into which the dipstick may be subsequently placed. Typically, a volume of the cavity is at least 0.03 mL and/or less than 5 mL (e.g., 0.03-1 mL). For example, the volume of the cavity may be at least 0.15 mL, e.g., at least 0.25 mL, e.g., at least 0.4 mL.

In some applications, apparatus 20 comprises a kit in which the plunger and tube are disposed. In some applications, the plunger is disposed entirely outside of the tube when contained in the kit, to allow for immediate use of the tube without first removing the plunger. In some applications, the kit further contains the particulate-presence-testing-facilitation solution (e.g., the A and B solution).

In some applications, apparatus 20 further comprises a puncturing element 30a protruding from a distal end of the plunger, puncturing element 30a being configured to puncture the filter upon the plunger being advanced to the filter. In other applications, a disconnected puncturing element 30b is disposed within the kit that contains the plunger and tube. Puncturing element 30b is sized and shaped to be passable through an opening 34 at a distal end of the tube, and is configured to puncture the filter by being longer than a distance d0 from opening 34 to the filter. (Typically, the puncturing element is at least as long as the distance from opening 34 to the proximal side of the filter.) The puncturing of the filter facilitates the testing, by allowing the particulate-presence-testing-facilitation solution, which is typically passed into the tube from the distal end of the tube (as further described hereinbelow), to collect in cavity 28. Furthermore, the puncturing of the filter facilitates collection of the particulate for subsequent culturing, such as, for example, when a throat culture is performed alternatively or additionally to the rapid strep test. Typically, the distal end of plunger 24 is not convex; rather, the distal end of the plunger is generally flat. For example, as shown in FIG. 1, the distal end of the plunger, with the exception of cavity 28, is generally flat. In general, a plunger having a generally flat distal end is able to push more of the fluid through the filter, relative to a plunger having a convex distal end, since a greater portion of the distal end may be advanced all the way to the filter.

Typically, the proximal end of the tube is shaped to define a funnel-shaped proximal opening 36, which facilitates the collection of fluid in the tube. For some applications, to facilitate easily depositing gargled fluid directly from a subject's mouth into tube 22, a proximal-most diameter D0 of funnel-shaped proximal opening 36 is at least 20%, e.g., at least 25%, e.g., at least 30%, e.g., at least 40%, e.g., at least 50%, greater than a diameter D6 of tube 22, and is typically less than 300%, e.g., less than 250%, e.g., less than 200% greater than diameter D6 of tube 22. In some applications, the distal end of the tube is shaped to define a conduit 32, such as, for example, by comprising a Luer lock. Conduit 32 facilitates testing for presence of the particulate, as further described hereinbelow with reference to FIG. 2.

Figure 2:
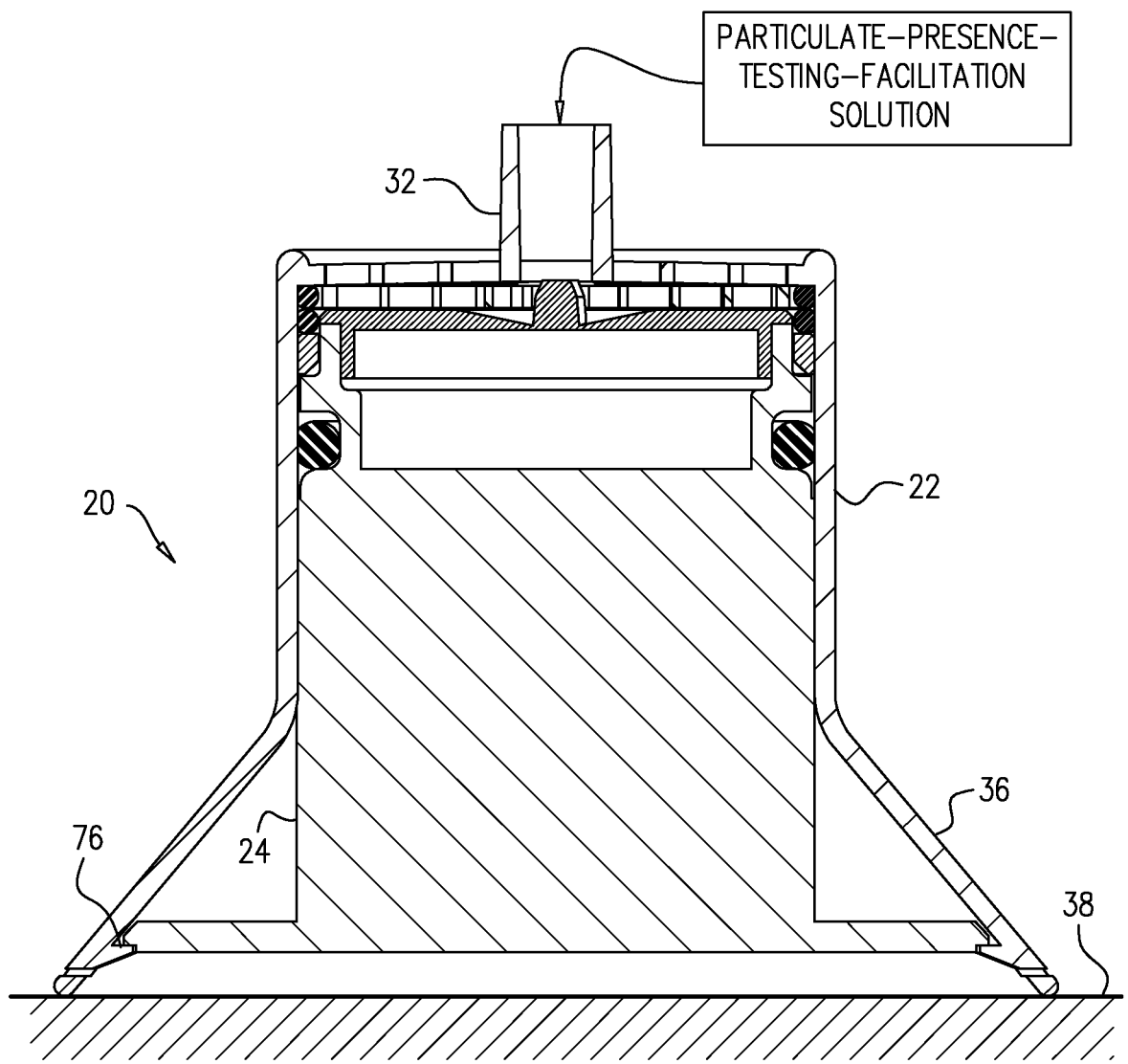

Reference is now made to FIG. 2, which is a schematic illustration of apparatus 20, in accordance with some applications of the present invention. Typically, following the pushing of the fluid through filter 26 (FIG. 1), the plunger and tube are turned upside-down, such that the distal opening of the tube is above (with respect to gravity) the proximal opening of the tube. For example, the plunger and tube may be made to rest on a horizontal surface 38, on the proximal end of the tube (as shown in the figure) or the proximal end of the plunger. Subsequently, the particulate-presence-testing-facilitation solution is applied to the filter, i.e., the solution is placed into the tube (e.g., by being passed through conduit 32) such that the solution is in contact with the filter. In some applications, the distal end of the tube (e.g., conduit 32) is funnel-shaped; this shape facilitates the placing of the particulate-presence-testing-facilitation solution into the tube. Conduit 32 also facilitates a rapid strep test, by allowing passage of the dipstick and by holding the dipstick when the proximal end of the tube or plunger is resting on a horizontal surface.

In some applications, before testing the filter for presence of the particulate, a culture medium (e.g., tryptic soy broth) is used to culture the particulate, and/or a preserving medium is used to preserve the particulate in a viable or non-viable state. (For example, saline may be used to preserve the particulate in a viable state, while ethanol may be used to preserve the particulate in a non-viable state.) An advantage of culturing the particulate is that the testing sensitivity generally increases as the amount of particulate increases. An advantage of preserving the particulate is that the testing (e.g., a rapid strep test, or a throat culture to supplement the rapid strep test) may be performed even after some time has passed from the collection of the fluid.

In some applications, as noted above, apparatus 20 is used to test for presence of a microorganism, such as streptococcus bacteria. In such applications, the particulate-presence-testing-facilitation solution may include a releasing agent (e.g., the A and B solution), which, upon contacting the microorganism, releases an antigen from the microorganism. Subsequently, the area into which the antigen is released may be tested for presence of the antigen.

In some applications, the tube and plunger are configured such that, following the plunger being maximally advanced within the tube, the plunger is withdrawable from the tube only by use of a tool or by breaking a portion of the apparatus. For example, as shown in FIG. 2, the proximal end of the plunger may be not proximal to (i.e., distal to or flush with) the proximal end of the tube, when the plunger is maximally advanced within the tube, such that the plunger effectively becomes stuck in the tube. This generally serves to prevent the plunger from leaving the tube when the tube is handled, e.g., turned upside-down. Alternatively or additionally, the apparatus comprises a locking mechanism 76 (FIG. 1) that is configured to lock the plunger inside the tube following the plunger being maximally advanced within the tube. For example, as shown in FIG. 1, locking mechanism 76 may comprise tabs that can be pushed inward by the plunger as the plunger is advanced into the tube, but cannot be pushed outward, such that the plunger, following a maximal advancement thereof, is blocked from exiting the tube.

In some applications, there is no locking mechanism, and plunger 24 can easily be removed from tube 22 subsequently to plunger 24 being maximally advanced.

Reference is again made to FIG. 1. Typically, proximal-most diameter D0 of the proximal opening of the tube is relatively large, such as to facilitate (a) the collection of the fluid in the tube, and/or (b) the upside-down resting of the tube on horizontal surface 38 (FIG. 2). For example, a ratio of D0 to a diameter D1 of the distal opening of the tube may be at least 13. As noted above, in some applications, the tube and plunger rest on the proximal end of the plunger. To facilitate this, the proximal end of the plunger may be relatively wide; for example, a ratio of the diameter D2 of the proximal end of the plunger to the length L2 of the plunger may be at least 1.

Figure 3:
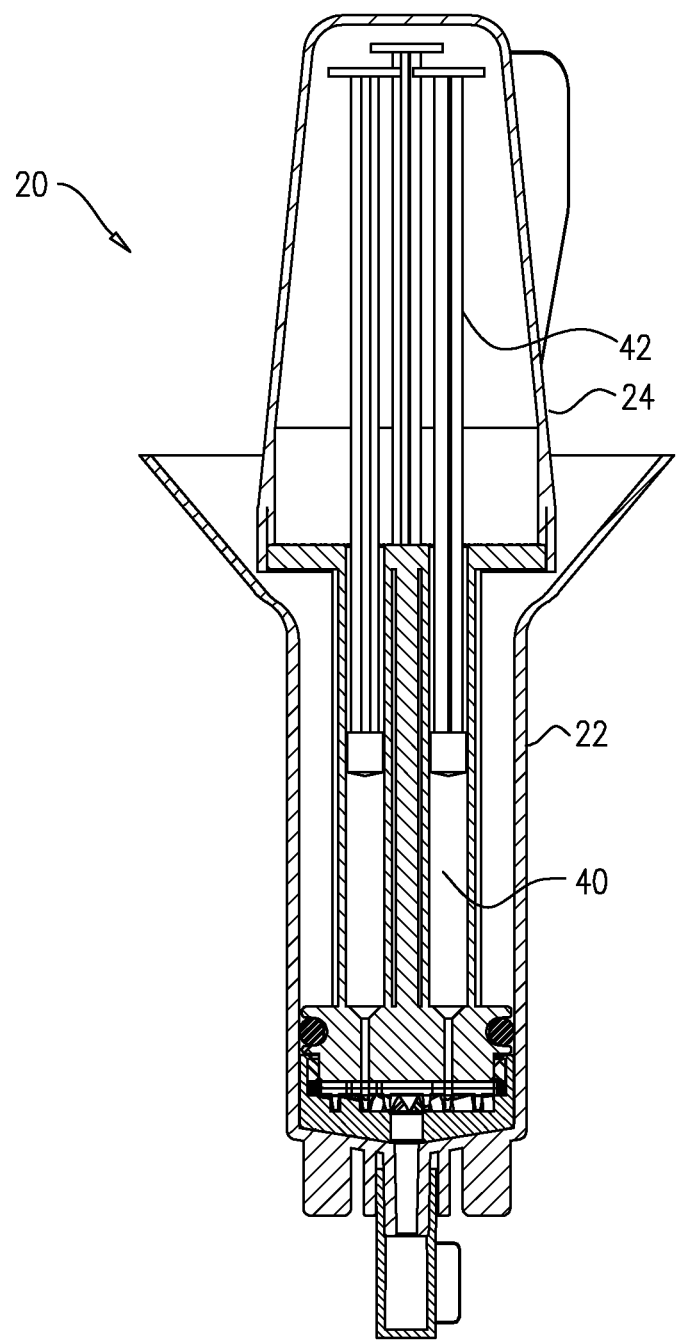

Reference is now made to FIG. 3, which is a schematic illustration of apparatus 20, in accordance with some applications of the present invention. In some applications, plunger 24 is shaped to define at least one plunger lumen 40 containing a particulate-presence-testing-facilitation solution. (FIG. 3 shows an application in which there are two plunger lumens, one containing the A solution, and the other containing the B solution.) The particulate-presence-testing-facilitation solution is deployed (i.e., placed into the tube) by being passed out of plunger lumen 40, e.g., via a sub-plunger 42 that is slidably disposed within the plunger lumen.

Figure 4:
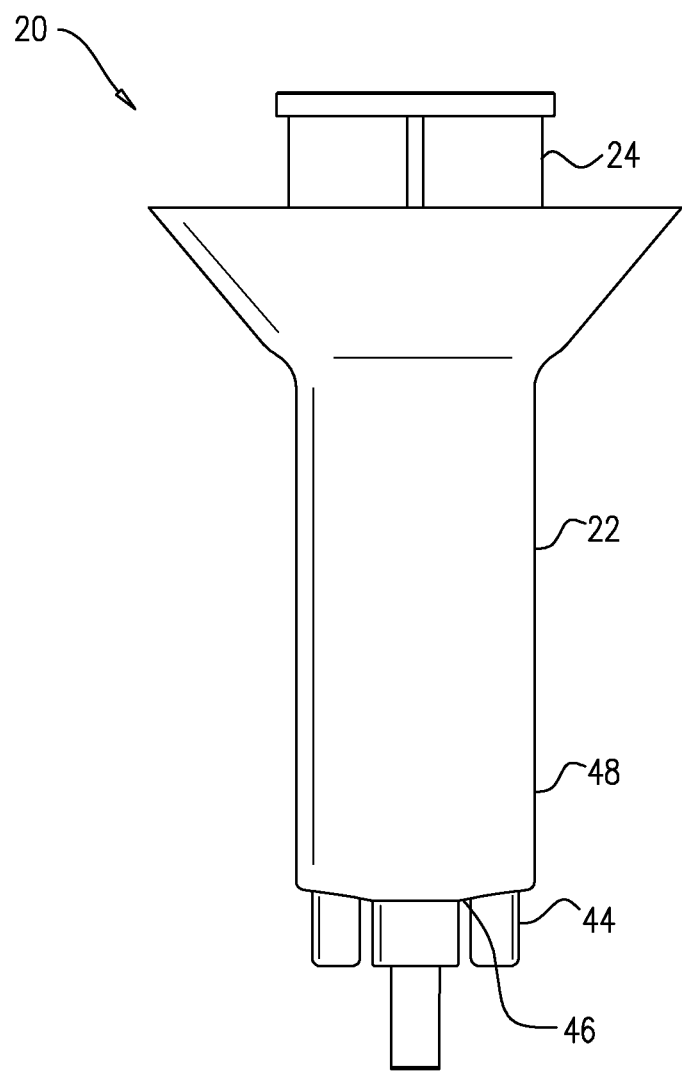
Figure 10A:
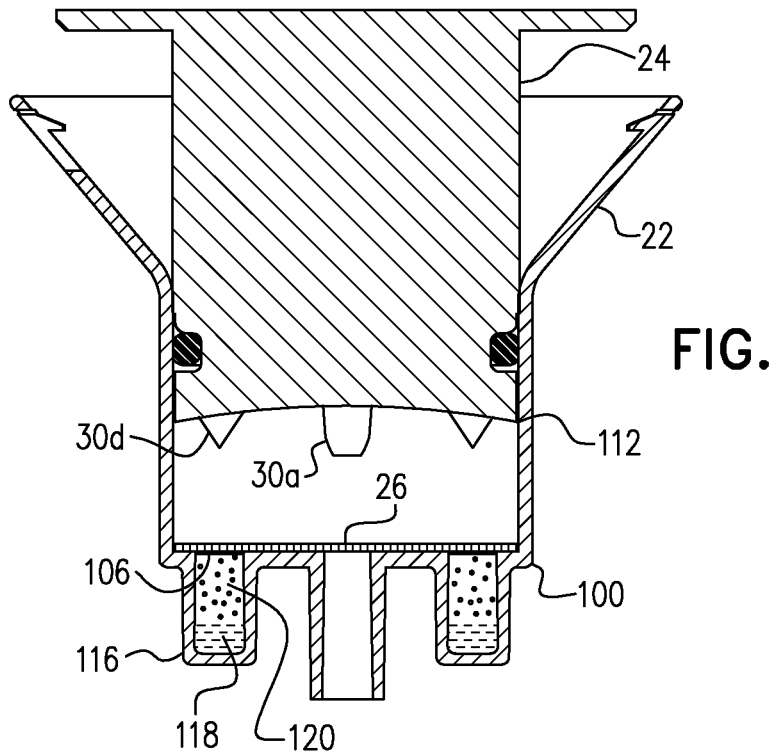
FIGS. 10A-B are schematic illustrations of a configuration of the apparatus for testing for presence of a particulate in a fluid, in accordance with some applications of the present invention.

Reference is now made to FIG. 4, which is a schematic illustration of apparatus 20, in accordance with some applications of the present invention. In some applications, a wall of the tube is shaped to define at least one enclosed cavity 44 containing the particulate-presence-testing-facilitation solution. Enclosed cavity 44 is configured to open upon the plunger being moved within the tube. For example, the plunger may puncture a proximally-facing cover of the enclosed cavity as the plunger is advanced, thus opening the enclosed cavity. Alternatively, the enclosed cavity may be separated from the lumen of the tube by a one-way valve. Following maximal advancement of the plunger, the plunger is withdrawn slightly, thus creating a vacuum proximal to the valve that causes the valve to open. FIG. 4 shows an application in which the bottom wall 46 of the tube is shaped to define enclosed cavity 44. Alternatively or additionally, a distal portion of the lateral wall 48 of the tube, and/or the distal end of the plunger, may be shaped to define an enclosed cavity containing the particulate-presence-testing-facilitation solution. In some applications, cavity 44 further contains a gas above atmospheric pressure (e.g., as shown in FIG. 10A), such that the particulate-presence-testing-facilitation solution is forced out upon the opening of cavity 44. In general, for all applications described herein, the opening of cavity 44 can alternatively be done independently of plunger 24.

Figure 5:
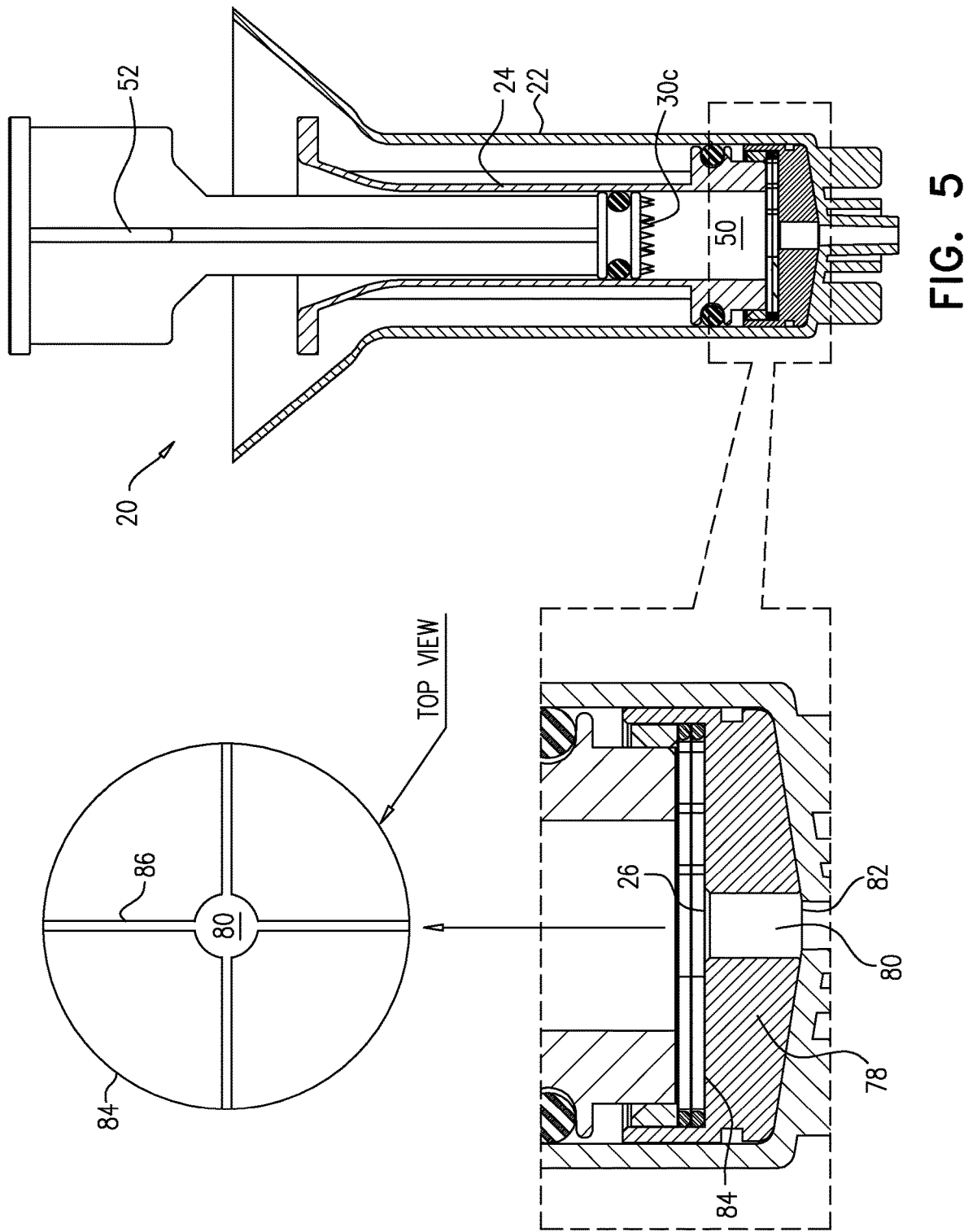

Reference is now made to FIG. 5, which is a schematic illustration of apparatus 20, in accordance with some applications of the present invention. In some applications, plunger 24 is shaped to define a plunger lumen 50. A shaft 52, which is shaped to be slidably disposed within plunger lumen 50, comprises a puncturing element 30c at a distal end thereof. Shaft 52 is advanced within the plunger lumen until puncturing element 30c punctures the filter. (As described above with reference to FIG. 1, the puncturing of the filter facilitates testing for the particulate.)

As also shown in FIG. 5, in some applications, apparatus 20 comprises an insert 78 disposed within a distal portion of the tube and not fixed to the plunger, filter 26 being coupled to a proximally-facing surface 84 of insert 78. One function of insert 78 is to provide a generally flat proximally-facing surface to support the filter, such that a particular tube may be used even if the tube has a convex distal end. Typically, insert 78 is shaped to define (a) an at least partially distally-facing opening 82 therein, and (b) a passage 80 from proximally-facing surface 84 to opening 82. Passage 80 provides for exit of fluid from the tube as the plunger is advanced. In some applications, as shown in the top (distally-facing) view of surface 84, the insert is further shaped to define a plurality of grooves 86 in surface 84, respective spaces within the grooves being in fluid communication with passage 80. Grooves 86 facilitate the flow of fluid through the passage and out of the tube.

Figure 6:
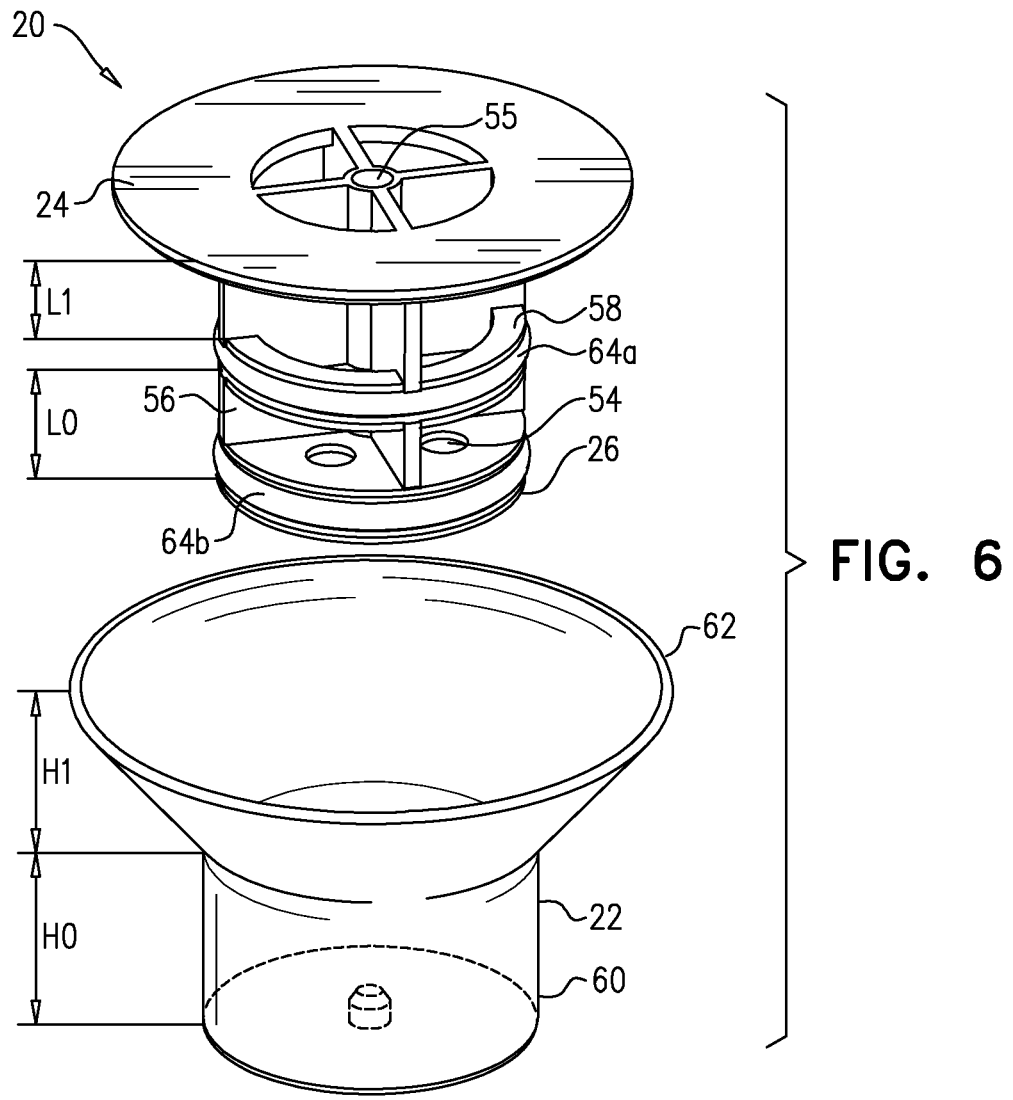

Reference is now made to FIG. 6, which is a schematic illustration of apparatus 20, in accordance with some applications of the present invention. In the application shown in FIG. 6, the distal end of plunger 24 is shaped to define one or more passageways 54 therethrough, and filter 26 is coupled to the distal end of the plunger. In some applications, the distal end of tube 22 does not have an opening, or has an opening that is permanently closed. In other applications, the distal end of tube 22 is shaped to define an openable seal (not shown), and/or apparatus 20 comprises a stopper (for example, as show in FIGS. 13A-D) configured to close the distal opening of the tube, e.g., by being disposed over the distal opening of the tube. In any case, while the plunger is advanced, the distal end of the tube remains closed, such that the fluid in the tube is pushed through the filter, through passageways 54, and into one or more (e.g., four) compartments 56 that are in fluid communication with the passageways. Typically, a total volume of compartments 56 is at least 0.5 mL and/or less than 60 mL, e.g., between 5 and 30 mL, e.g., between 8 and 20 mL.

The tube comprises a distal cylindrical portion 60, and/or a proximal funnel portion 62 coupled to cylindrical portion 60. Typically, the plunger is shaped to define a disk 58 that is proximal to compartments 56, disk 58 inhibiting passage of liquid from the compartments to a proximal side of the disk, when the disk is inside the tube. Length L0 of the plunger distal to disk 58 is approximately equal to (e.g., is within 10 mm of) the height H0 of the cylindrical portion. Thus, once the plunger has been maximally advanced within the tube, the fluid is trapped inside the tube, such the tube and plunger may be safely handled, e.g., turned upside-down (as shown in FIG. 2) for testing purposes. Typically, a first sealing ring 64a surrounds the plunger proximally to the compartments, and/or a second sealing ring 64b surrounds the plunger distally to the compartments. First sealing ring 64a facilitates the trapping of the fluid inside the compartments, while second sealing ring 64b inhibits fluid from passing between the plunger and the tube as the plunger is advanced.

Passageways 54 are typically many, well distributed, and/or large, to facilitate efficient passage of fluid therethrough. Typically, compartments 56 are not completely surrounded by a wall, such that air may escape the compartments while fluid flows in to the compartments. For example, each of the four compartments shown in FIG. 6 is entirely open. In some applications, the length L1 of the plunger proximal to the disk is not greater than height H1 of the funnel portion, such that the plunger becomes stuck in the tube upon being maximally advanced. Alternatively or additionally, locking mechanism 76 (FIG. 1) locks the plunger inside the tube.

In an alternative application, air escapes through one or more passageways (not shown) leading from the compartments to the proximal end of the plunger. (The passageways are closed subsequent to the plunger being maximally advanced within the tube.)

Following the plunger being maximally advanced within the tube, the filter may be tested for presence of the particulate, e.g., as described hereinabove with reference to FIG. 2. In some applications, the distal end of the tube is shaped to define a conduit, such as a Luer lock, that facilitates the testing for the particulate, as described hereinabove with reference to FIG. 2. For applications in which the distal end of the tube is permanently closed, the testing of the filter may be conducted via a passageway 55 passing through the plunger (but not through any of passageways 54) from the proximal end of the plunger to the distal end of the plunger. For example, a particulate-presence-testing-facilitation solution and/or a dipstick may be passed through passageway 55.

Figure 7:
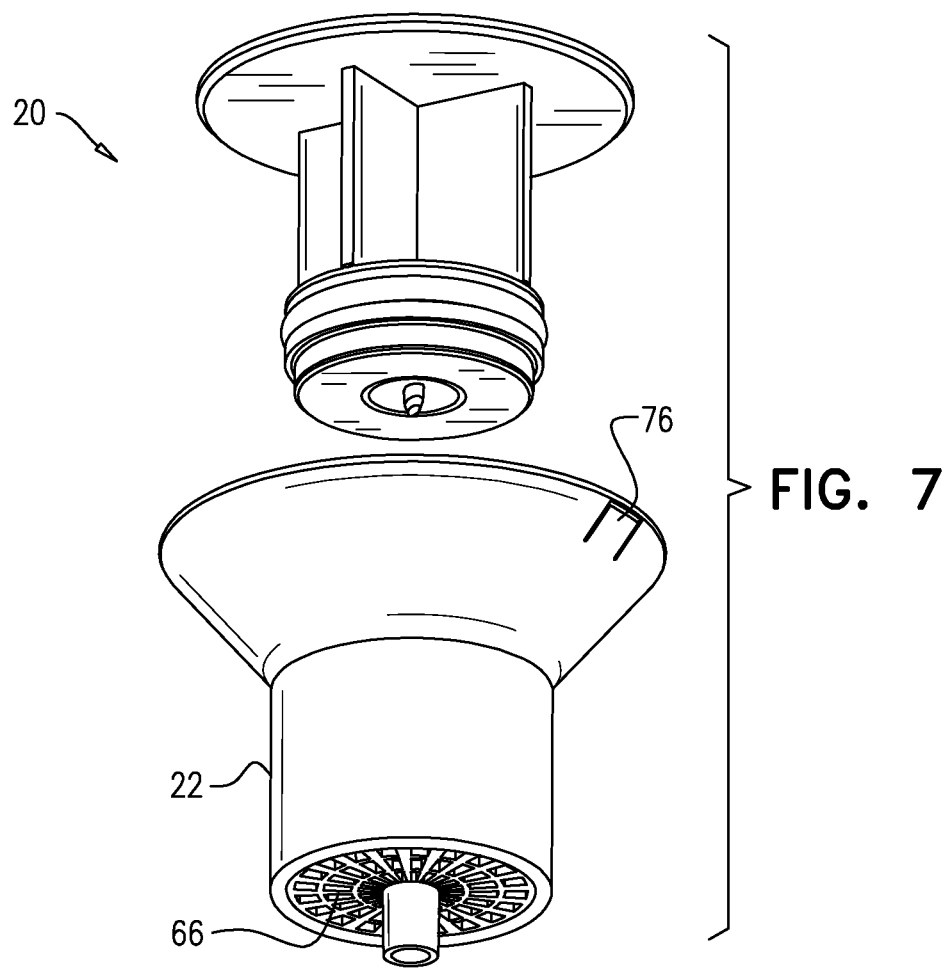

Reference is now made to FIG. 7, which is a schematic illustration of apparatus 20, in accordance with some applications of the present invention. In FIG. 7, tube 22 is shaped to define a plurality of openings 66 at a distal end thereof. The filter is disposed within a distal portion of the tube, proximal to the plurality of openings 66. The plurality of openings facilitates the pushing of the fluid through the filter and out of the tube by reducing the pressure that must be applied to the plunger, relative to if the tube were to have a single (relatively small) opening. The total area of the plurality of openings is at least 10% and/or less than 90% (e.g., 10%-80%, e.g., 10%-70%, e.g., 20%-70%) of the cross-sectional area of the distal end of the tube.

Figure 8:
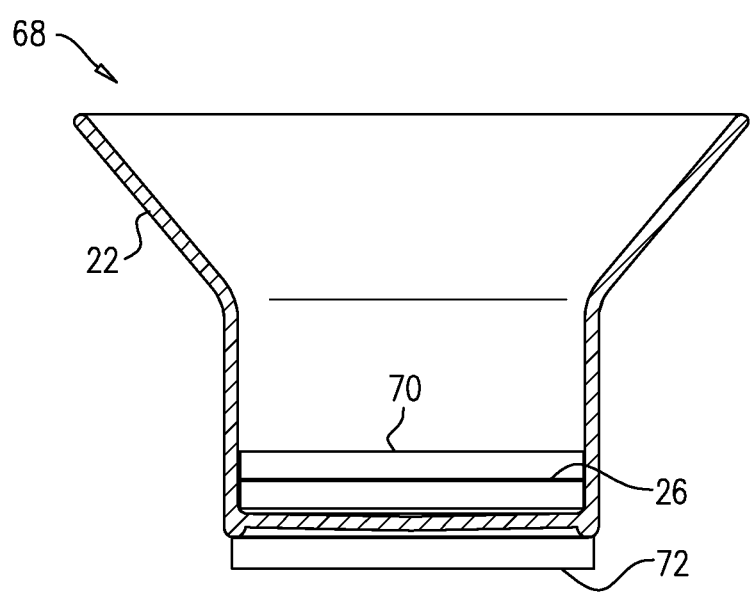
FIG. 8 is a schematic illustration of apparatus for collecting fluid, in accordance with some applications of the present invention.

Reference is now made to FIG. 8, which is a schematic illustration of apparatus 68 for collecting fluid, in accordance with some applications of the present invention. Apparatus 68 comprises tube 22, which contains a medium 70 (e.g., in the form of a gel, powder, or coating) that facilitates testing the fluid for presence of the particulate. For example, medium 70 may include a culture medium (e.g., tryptic soy broth) configured to culture a microorganism, a spore, a virus, a mite, a biological cell, a biological antigen, a protein, a protein antigen, and/or a carbohydrate antigen. Alternatively or additionally, medium 70 may include a releasing medium (e.g., A and B solution) configured to release an antigen from a microorganism. Alternatively or additionally, medium 70 may include a heating medium (e.g., plaster and/or calcium chloride) configured to undergo an exothermic reaction, the heat from the exothermic reaction helping to preserve and/or culture the particulate. Alternatively or additionally, medium 70 may include a salt, and/or another preserving medium (e.g., formalin and/or ethanol alcohol) configured to preserve a microorganism, a spore, a virus, a mite, a biological cell, a biological antigen, a protein, a protein antigen, and/or a carbohydrate antigen in a viable or non-viable state. (One advantage of having a salt contained in the tube is that the subject need not gargle saline solution in order to preserve the bacteria; rather, the subject may gargle a more pleasant-tasting fluid, and subsequently spit the gargled fluid into the salt-containing tube.)

Filter 26 is disposed within a distal portion of the tube, the medium being disposed distally and/or proximally to the filter. Following the collection of the fluid in the tube, the plunger is used to push the fluid through the filter and out of the tube. (Alternatively, apparatus 68 may be used in combination with apparatus and techniques described with reference to FIG. 6; in such applications, filter 26 is disposed on the distal end of the plunger.)

In some applications, apparatus 68 further comprises a heating element 72 that is configured to heat the tube. For example, apparatus 68 may be contained in a kit in which heating element 72 and the tube are disposed. The heating element may comprise a chemical heating element (e.g., plaster and/or calcium chloride), and/or an electric heating element. The heating of the tube generally facilitates the culturing and/or preserving function of medium 70.

One manner in which apparatus 68 may be used will now be described. A subject at home experiences a sore throat, and decides that he would like to have a rapid strep test done. The subject therefore opens up his "home strep test kit" and pulls out the tube and plunger. The subject collects gargled fluid in the tube, uses the plunger as described hereinabove, and subsequently, brings the tube to the doctor's office. From the time of collection until the subject arrives at the doctor's office, culture medium 70 (optionally, in combination with heat from heating element 72 and/or a heating medium) allows for the bacteria to multiply. At the doctor's office, the doctor conducts a rapid strep test. (Alternatively, the collection of fluid in the tube may be done at the doctor's office; in such cases, the doctor may optionally heat the tube for some time before performing the strep test, in order to boost the sensitivity of the strep test.)

Reference is again made to FIG. 1. In some applications, apparatus 20 comprises two filters disposed within the distal portion of the tube. The first filter 74a, which may act as a "pre-filter", has a pore size of at least 0.5 microns and/or less than 100 microns, while the second filter 74b, which is typically disposed distally to first filter 74a, has a pore size of at least 0.1 microns and/or less than 20 microns. (Typically, the pore size of the first filter is larger than the pore size of the second filter. In some applications, however, the respective pore sizes may be equal.) It is hypothesized by the inventors that the second filter, in addition to capturing the particulate, may also facilitate the capturing of the particulate by the first filter, by providing additional resistance to the pushing of the fluid out of the filter.

Filters 74a and 74b may also be disposed on the distal end of the plunger, e.g., in place of the single filter shown in FIG. 6. In such applications, the first filter (which, typically, has a larger pore size) is typically distal to the second filter.

The pore sizes of filters 74a and 74b vary, depending on the type of particulate being tested for. For example:

(a) For streptococcus bacteria, typical pore sizes are between 0.5 and 20 microns for the first filter, and between 0.1 microns and 1 micron for the second filter.

(b) For pollen spores, typical pore sizes are between 10 and 100 microns for the first filter, and between 1 micron and 10 microns for the second filter.

(c) For monocytes, typical pore sizes are between 5 and 25 microns for the first filter, and between 1 micron and 20 microns for the second filter.

Figure 9A:
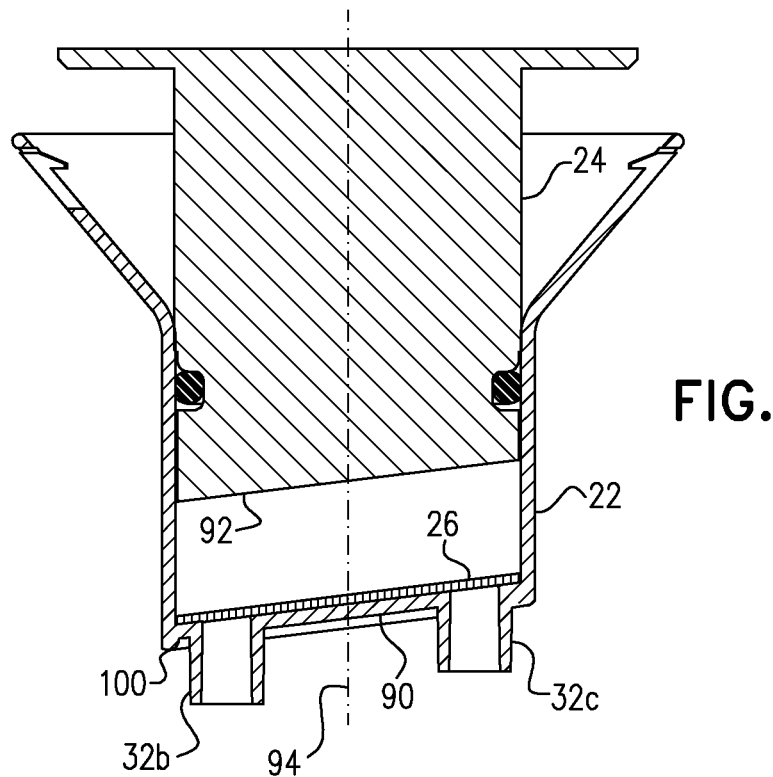
FIGS. 9A-B are schematic illustrations of a configuration of the apparatus for testing for presence of a particulate in a fluid, in accordance with some applications of the present invention.
Figure 9B:
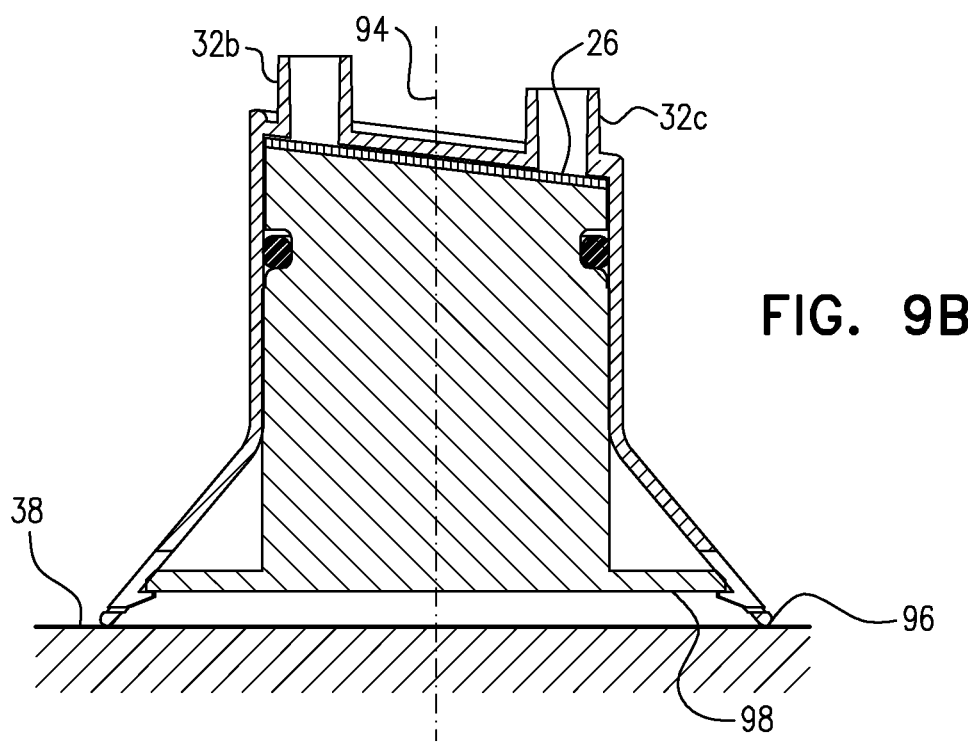

Reference is now made to FIGS. 9A-B, which are schematic illustrations of apparatus 20, in accordance with some applications of the present invention. In some applications, a distal surface 90 of tube 22 is oriented at a slant with respect to a lateral wall of tube 22, and a distal surface 92 of plunger 24 is oriented at a slant with respect to a longitudinal axis 94 of plunger 24. Typically, tube 22 and plunger 24 are configured such that the slant of distal surface 90 of tube 22 aligns with the slant of distal surface 92 of plunger 24 at at least one rotational orientation of tube 22 with respect to plunger 24. Filter 26 is disposed on the inside of slanted distal surface 90 of tube 22. Distal end 100 of tube 22 is shaped to define at least two conduits 32b and 32c, disposed such that conduit 32b is disposed at the higher end of the slant and conduit 32c is disposed at the lower end of the slant, when a proximal end 96 of tube 22 or a proximal end 98 of plunger 24 is resting on horizontal surface 38, as shown in FIG. 9B. Typically, the particulate-presence-testing-facilitation solution is passed through conduit 32b, disposed at the higher end of the slant, such that the particulate-presence-testing-facilitation solution flows down the slant along filter 26. Filter 26 may then be tested for presence of the particulate by inserting a dipstick through conduit 32c, disposed over the lower end of the slant.

In some applications, distal surface 90 of tube 22 is shaped to define a cone as is common in syringe plungers (configuration not shown).

Figure 20:
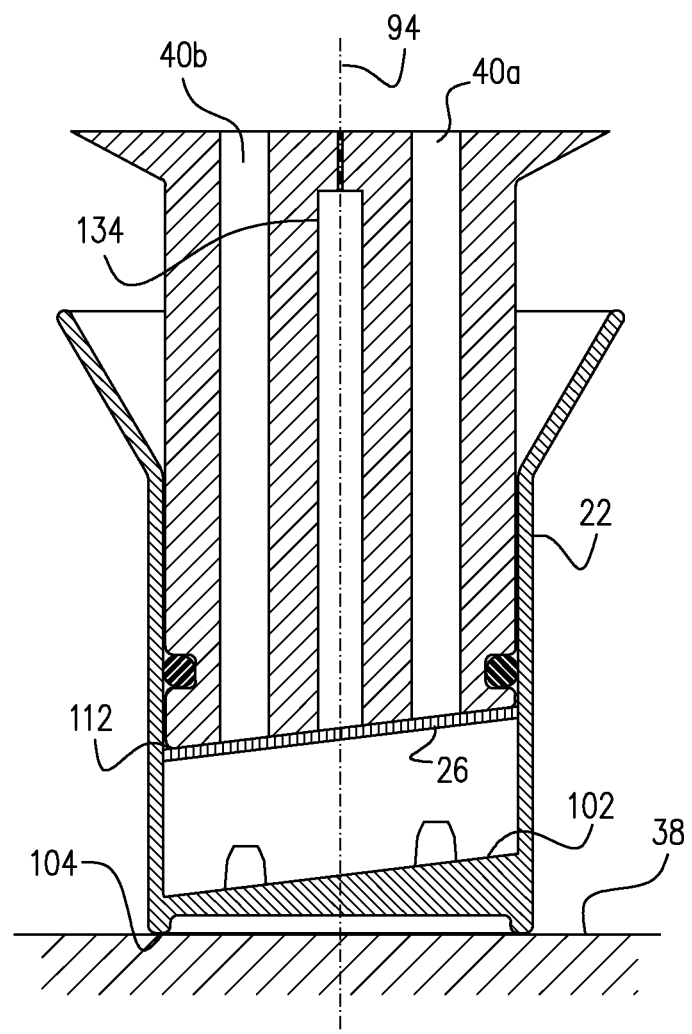
FIG. 20 is a schematic illustration of a configuration of the apparatus for testing for presence of a particulate in a fluid, in accordance with some applications of the present invention.

Reference is now made to FIG. 20, which is a schematic illustration of apparatus 20, in accordance with some applications of the present invention. In some applications, filter 26 is disposed on distal end 112 of plunger 24, such that the fluid is pushed through filter 26 into a compartment 134 in plunger 24. A proximally-facing distal surface 102 of tube 22 is oriented at a slant with respect to a lateral wall of tube 22, and distal end 112 of plunger 24 is oriented at a slant with respect to longitudinal axis 94 of plunger 24. Typically, tube 22 and plunger 24 are configured such that the slant of proximally-facing distal surface 102 of tube 22 aligns with the slant of distal end 112 of plunger 24 at at least one rotational orientation of tube 22 with respect to plunger 24. Plunger 24 is shaped to define at least two plunger lumens 40a and 40b, disposed such that plunger lumen 40a is disposed over the higher end of the slant and plunger lumen 40b is disposed over the lower end of the slant, when a distally-facing distal surface 104 of tube 22 is resting on horizontal surface 38. Typically, the particulate-presence-testing-facilitation solution is passed through plunger lumen 40a disposed over the higher end of the slant, such that the particulate-presence-testing-facilitation solution flows down the slant along filter 26. Filter 26 may then be tested for presence of the particulate by inserting a dipstick through plunger lumen 40b disposed over the lower end of the slant.

Figure 10B:
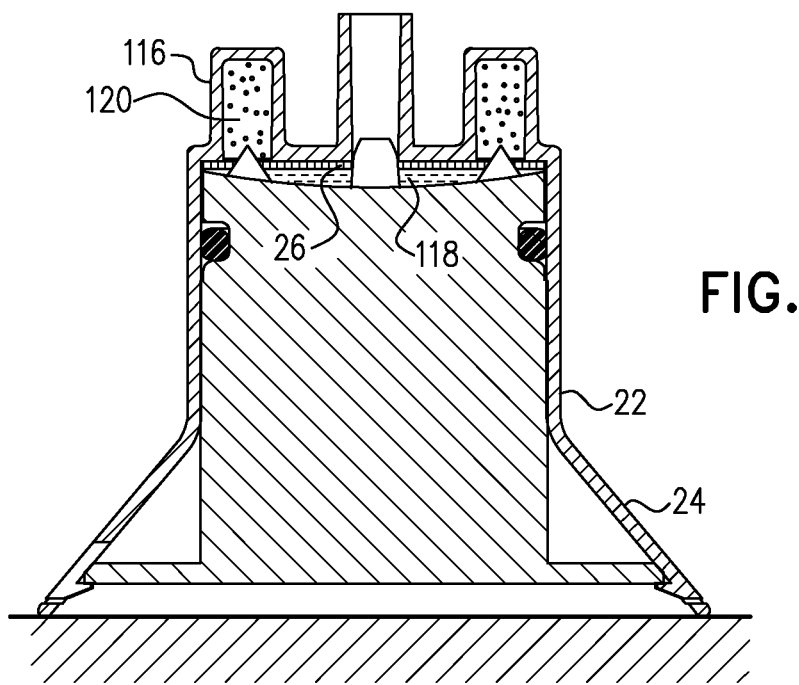

Reference is now made to FIGS. 10A-B, which are schematic illustrations of apparatus 20, in accordance with some applications of the present invention. In some applications, a wall of tube 22 is shaped to define at least one enclosed cavity 116 containing a particulate-presence-testing-facilitation solution 118 and a gas 120 above atmospheric pressure. As shown in FIG. 10A, cavity 116 may be in a distal wall of tube 22 and filter 26 disposed in distal end 100 of tube 22, proximal to cavity 116. Enclosed cavity 116 is closed with a seal 106 and configured to open following initiation of distal movement of plunger 24 in tube 22, such that particulate-presence-testing-facilitation solution 118 is forced out of enclosed cavity 116 and applied to filter 26. In some applications, at least one puncturing element 30d is disposed on distal end 112 of plunger 24, and configured to open enclosed cavity 116 by puncturing filter 26 and seal 106. In some applications, puncturing element 30a may be disposed on distal end 112 of plunger 24, and configured to puncture filter 26 upon plunger 24 being maximally advanced in tube 22.

Figure 21A:
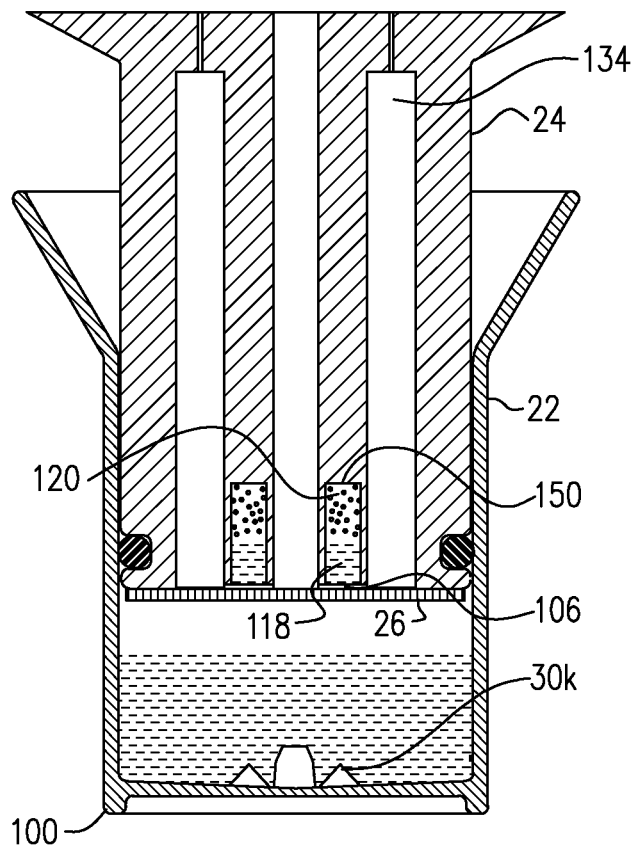
FIGS. 21A-B are schematic illustrations of a configuration of the apparatus for testing for presence of a particulate in a fluid, in accordance with some applications of the present invention.
Figure 21B:
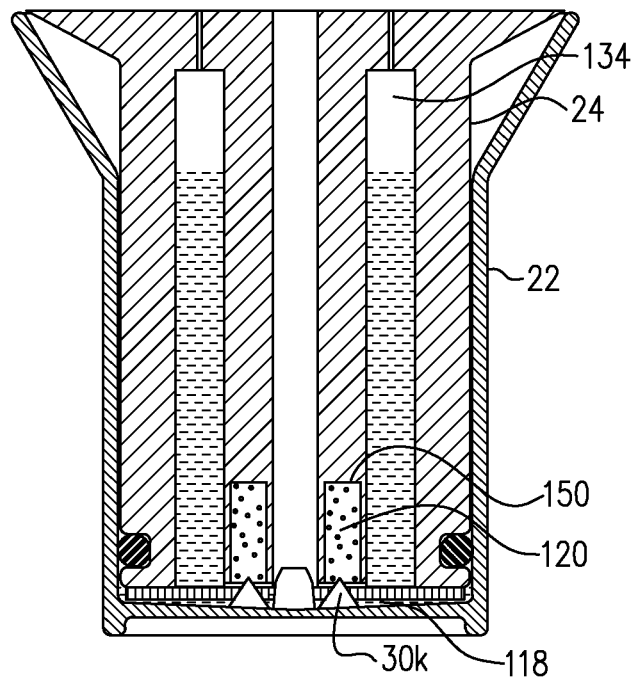

Reference is now made to FIGS. 21A-B, which are schematic illustrations of apparatus 20 in accordance with some applications of the present invention. In some applications, filter 26 is disposed on distal end 112 of plunger 24 and a wall of plunger 24 is shaped to define at least one enclosed cavity 150 containing particulate-presence-testing-facilitation solution 118 and gas 120 above atmospheric pressure (FIGS. 21A-B). Enclosed cavity 150 is closed with seal 106 disposed proximal to filter 26. At least one puncturing element 30k protrudes in a proximal direction from distal end 100 of tube 22 to puncture filter 26 and seal 106 (FIG. 21B).

Figure 11B:
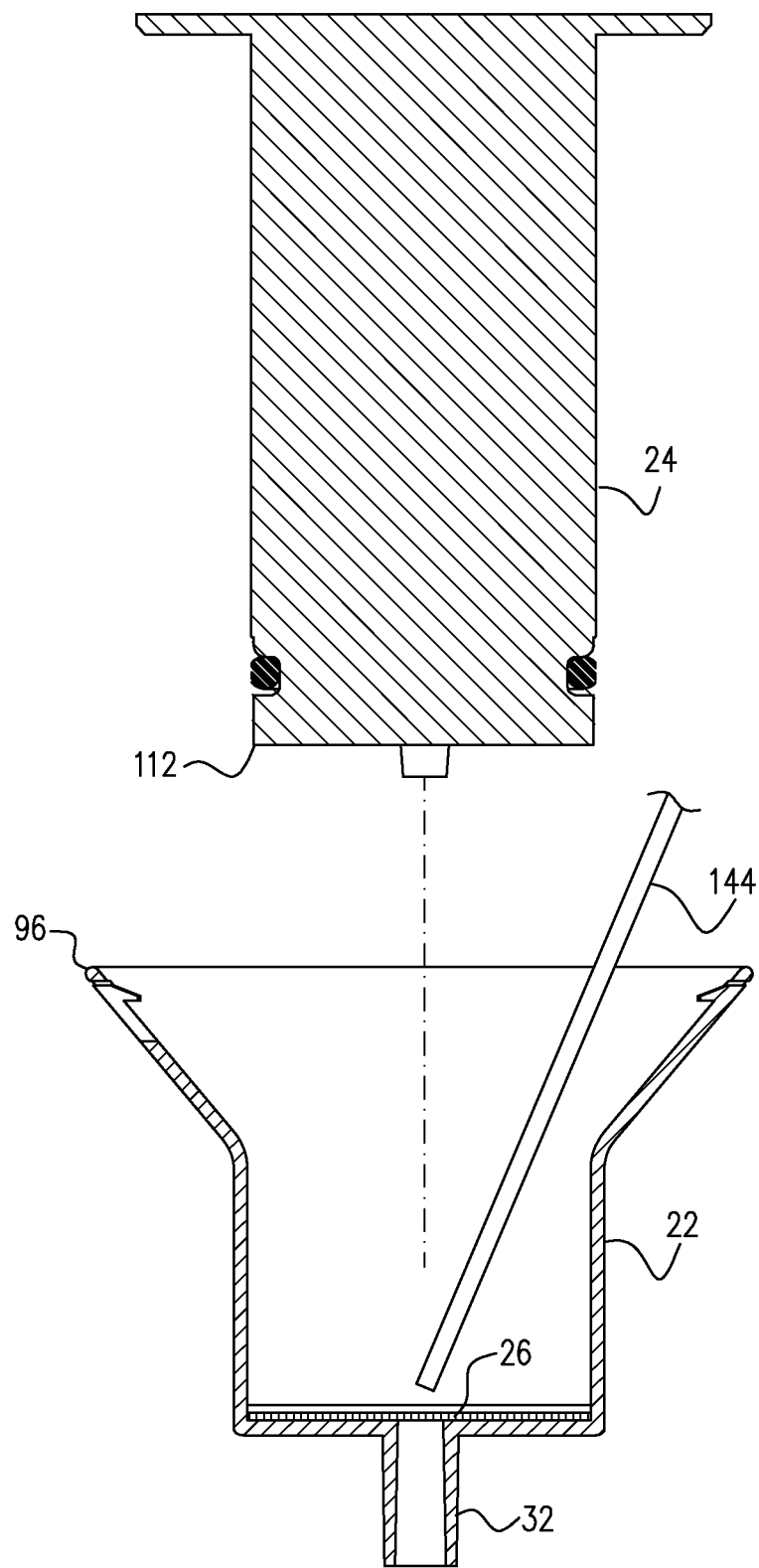

Reference is now made to FIGS. 11A-B, which are schematic illustrations of apparatus 20, in accordance with some applications of the present invention. In some applications, it would be advantageous to be able to test filter 26 for presence of the particulate in more than one way, for example by culturing (e.g., for 2-48 hours) the particulate collected on filter 26 as well as applying the particulate-presence-testing-facilitation solution for a rapid result. Therefore, in some applications, following the pushing of the fluid through filter 26, disposed in distal end 100 of tube 22, filter 26 is tested for presence of the particulate by (a) ascertaining if any of the particulate was trapped by the filter using a first protocol, and (b) if no particulate is found to be present, ascertaining using a second protocol. Typically, ascertaining using the first protocol comprises applying a particulate-presence-testing-facilitation solution to filter 26.

However, once the particulate-presence-testing-facilitation solution is applied to filter 26, the particulate present on filter 26 can no longer be cultured. Therefore, in some applications, a sample is taken prior to applying the particulate-presence-testing-facilitation solution to filter 26. In some applications, plunger 24 is removed from tube 22 (FIG. 11B), and subsequently the sample is transferred from distal end 112 of plunger 24 to a culture media surface. Filter 26, while inside tube 22, is then tested, using the first protocol, for presence of the particulate and if no particulate is found then the sample taken from distal end 112 of plunger 24 can be tested using the second protocol by ascertaining whether the particulate is on the culture media surface after the sample has been cultured.

In some applications, the sample is taken by swabbing filter 26 with swab 144. Filter 26 may be swabbed through conduit 32 in distal end 100 of tube 22 (FIG. 11A), or from a proximal end 96 of tube 22 after removing plunger 24 from tube 22 (FIG. 11B).

In some applications, the sample taken from filter 26 is plated on a culture media surface and cultured (e.g., for 2-48 hours), and if no particulate is found when filter 26 is tested using the first protocol, then the sample taken from filter 26 is tested using the second protocol, by ascertaining if any of the particulate is present on the culture media surface after the sample has been cultured (e.g., for 2-48 hours). Typically, ascertaining if any of the particulate was present on the culture media surface comprises observing the culture media surface or applying a particulate-presence-testing-facilitation solution to the culture media surface.

Reference is now made to FIGS. 12A-D, which are schematic illustrations of apparatus 20, in accordance with respective applications of the present invention. In some applications, a barrier 108 extends in a proximal direction from distal end 100 of tube 22, and plunger 24 is sized and shaped to define a recess 110 into which barrier 108 fits upon plunger 24 being advanced to barrier 108. This configuration allows for two filters, 26a and 26b, to be disposed in distal end 100 of tube 22 and separated by barrier 108. Having more than one filter provides the opportunity to simultaneously test for presence of the particulate using the first and second protocols, as well as the opportunity to test for the presence of more than one particulate without having to repeat the entire procedure.

Typically, plunger 24, once maximally advanced to barrier 108, is configured to prevent a particulate-presence-testing-facilitation solution that is applied to either one of filters 26a or 26b from contacting the other one of the filters.

Apparatus 20 may further comprise at least two puncturing elements 30e protruding from distal end 112 of plunger 24 and configured to puncture filters 26a and 26b, respectively, upon plunger 24 being advanced to filters 26a and 26b.

In some applications, distal end 100 of tube 22 is shaped to define at least two conduits 32d, configured to align with filters 26a and 26b, respectively. Following pushing the fluid through filters 26a and 26b, apparatus 20 may be turned upside-down and either one of filters 26a or 26b can be tested for presence of the particulate by passing the particulate-presence-testing-facilitation solution through a respective conduit 32d and subsequently inserting a dipstick through the respective conduit 32d. The second one of filters 26a or 26b can be left to culture inside tube 22 (e.g., 2-48 hours), or a sample may be taken from the second one filters 26a or 26b and cultured (e.g., for 2-48 hours).

In some applications, a distal portion of tube 22 is shaped to define at least one enclosed cavity 114 (FIG. 12C) containing the particulate-presence-testing-facilitation solution, and configured such that the particulate-presence-testing-facilitation solution in cavity 114 is applied to only filter 26a and not to filter 26b. A wall of cavity 114 is configured to open and release the particulate-presence-testing-facilitation solution. In some applications, at least one puncturing element 30h is disposed on distal end 112 of plunger 24, and configured to open enclosed cavity 114 by puncturing filter 26 the wall of cavity 114. Enclosed cavity 114 may contain both the particulate-presence-testing-facilitation solution and a gas above atmospheric pressure (for example, as shown in FIG. 10A), such that the particulate-presence-testing-facilitation solution is forced out upon opening of cavity 114. Filter 26a is then tested by inserting a dipstick through respective conduit 32d. Filter 26b may be left to culture (e.g., for 2-48 hours) inside tube 22, or a sample may be taken from filter 26b and cultured (e.g., for 2-48 hours).

In some applications, plunger 24 is shaped to define plunger lumen 40c (FIG. 12D), an opening of plunger lumen 40c being arranged to align with filter 26a and not to simultaneously align with filter 26b. A distal end of plunger lumen 40c is configured to open, upon plunger 24 being maximally advanced within tube 22, by a puncturing element 30i, protruding from distal end 100 of tube 22.

In some applications, plunger lumen 40c is closed at proximal end 98 of plunger 24 and contains the particulate-presence-testing-facilitation solution, and, upon opening of plunger lumen 40c, the particulate-presence-testing-facilitation solution is applied to only one filter 26a. In some applications, plunger lumen 40c further contains a gas above atmospheric pressure, such that the particulate-presence-testing-facilitation solution is forced out upon opening of plunger lumen 40c. Filter 26a is then tested by inserting a dipstick through respective conduit 32d. A sample may be taken from filter 26b and cultured (e.g., for 2-48 hours).

In other applications, plunger lumen 40c is initially empty and, following pushing the fluid through filters 26a and 26b, a sample can be taken from filter 26a by swabbing filter 26a with swab 144 from proximal end 98 of plunger 24 through plunger lumen 40c. The sample is cultured (e.g., for 2-48 hours) and after the sample has been taken, both filters 26a and 26b can then be tested by passing the particulate-presence-testing facilitation solution through respective conduits 32d and inserting dipsticks through respective conduits 32d. Filters 26a and 26b could be tested for presence of two different particulates respectively by passing different particulate-presence-testing-facilitation solutions through each respective conduit 32d.

In some applications, a length L3 (or corresponding area) of filter 26a (FIG. 12A) and a length L4 (or corresponding area) of filter 26b are equal to each other. In other applications, length L3 of filter 26a is at least 25% larger than length L4 of filter 26b. Having filters 26a and 26b differ in size allows the particulate-presence-testing-facilitation solution to be applied to the larger of filters 26a or 26b, thereby increasing the chance of detecting the particulate with the initial rapid test. The smaller of filters 26a or 26b is typically cultured (e.g., for 2-48 hours) to increase the presence of the particulate.

In some applications, a culture medium is disposed on at least one of filters 26a or 26b, eliminating the need to swab the respective filter. Following the pushing of the fluid through filters 26a and 26b, one of filters 26a or 26b is simply left to culture and the particulate-presence-testing-facilitation solution is applied to the other one of filters 26a or 26b, on which no culture medium is disposed.

Figure 13A:
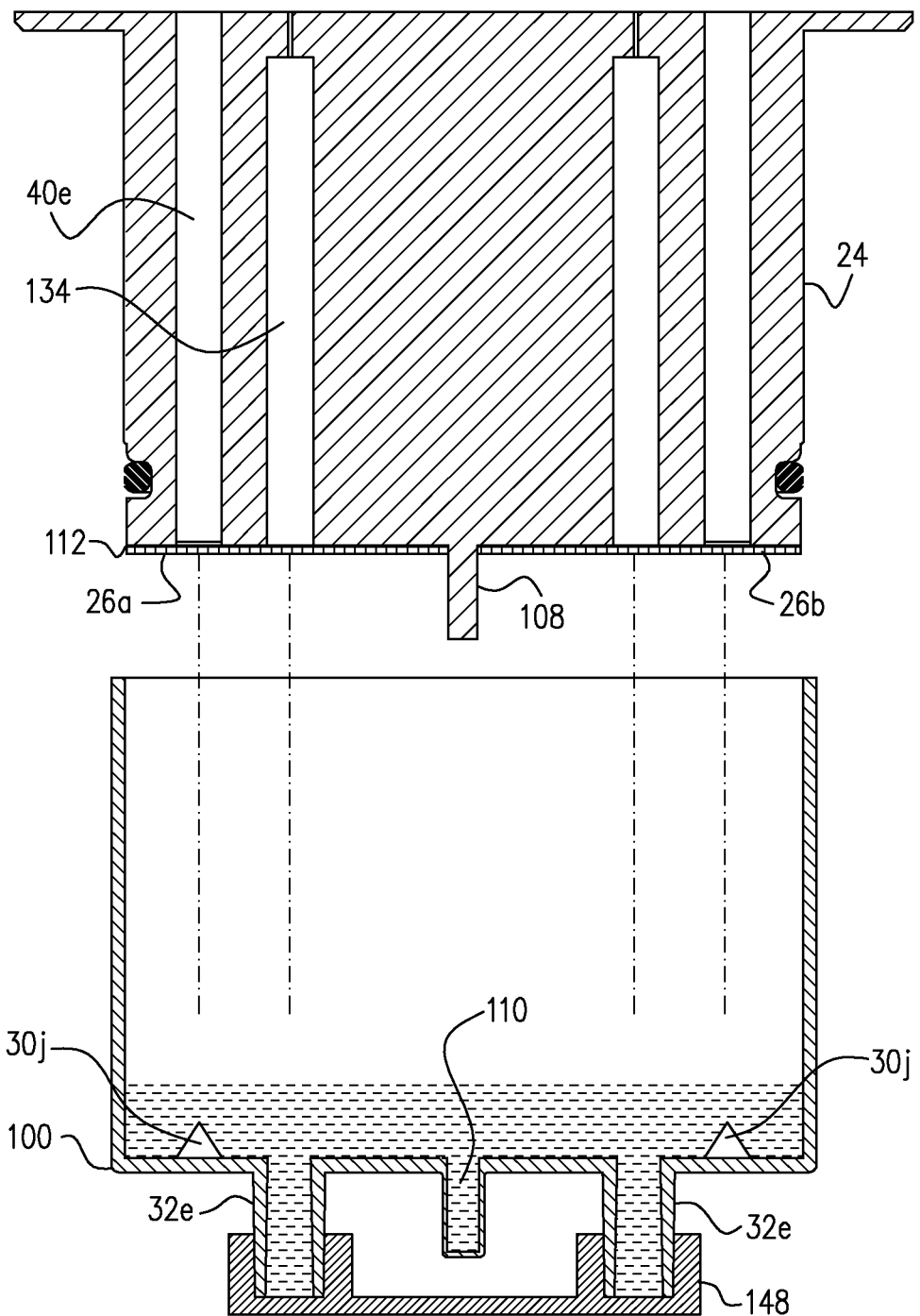
FIGS. 13A-D are schematic illustrations of various configurations of the apparatus for testing for presence of a particulate in a fluid, in accordance with some applications of the present invention.
Figure 13B:
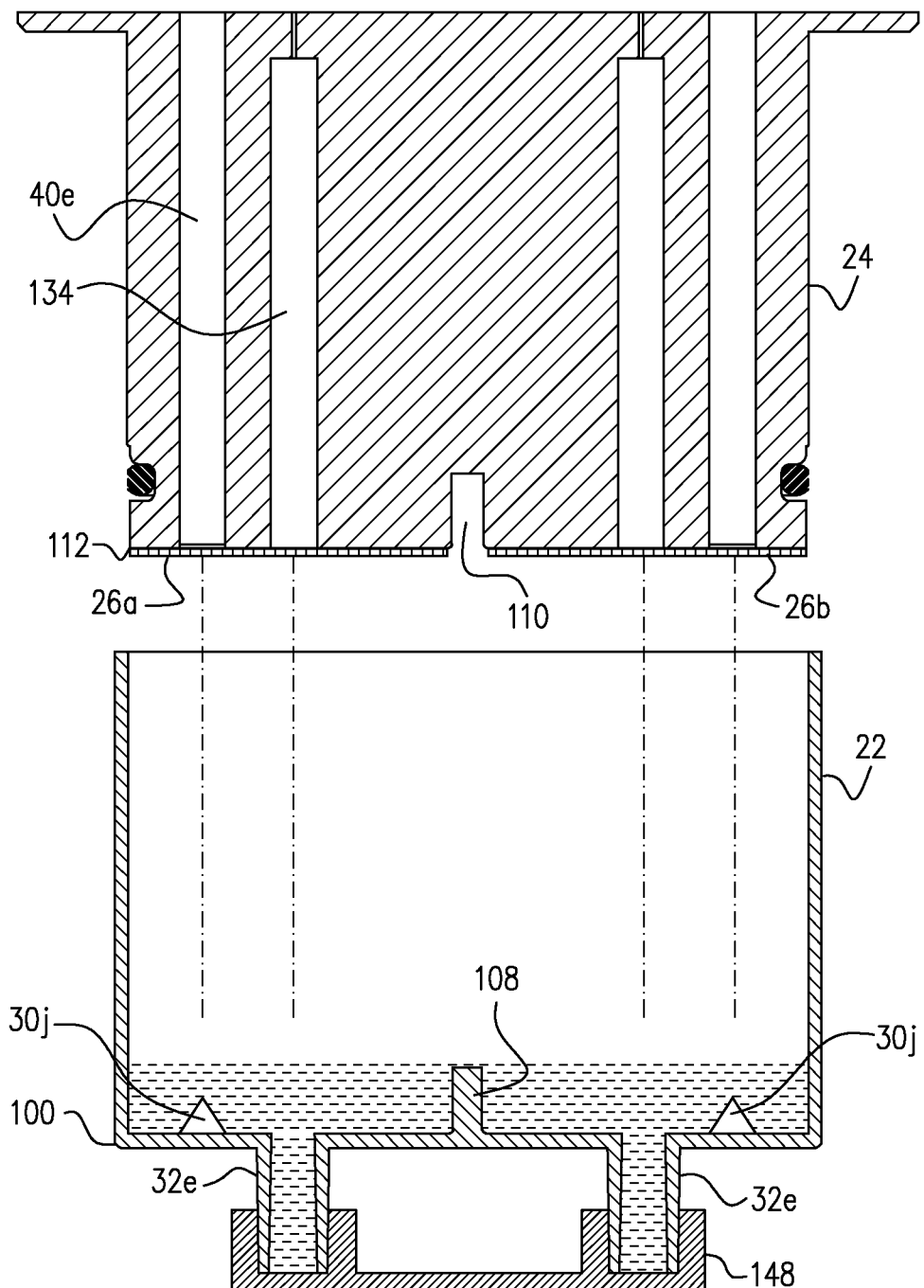

Height H3 of barrier 108 (FIG. 12A), extending from a distal to proximal direction, is typically low enough such that fluid collected in tube 22 is higher than the barrier (for example, as shown in FIG. 13B) and therefore evenly distributed over both filters 26a and 26b, yet high enough to prevent a particulate-presence-testing-facilitation solution that is applied to one of filters 26a or 26b after advancing of plunger 24 from contacting the other one of filters 26a or 26b. Typically, height H3 is less than 90% of a height H4 of tube 22. For example, height H3 of barrier 108 is less than a height of tube 22 that corresponds to a volume of 10 cc in tube 22, e.g. a height of tube 22 that corresponds to a volume of 5 cc, e.g. a height of tube 22 that corresponds to a volume of 1 cc, measured from distal end 100 of tube 22.

In some applications (configuration not shown), filters 26a and 26b are a first filter 26a and a second filter 26b, barrier 108 is a first barrier 108, and recess 110 is a first recess 110. First filter 26a is separated from second filter 26b by either first barrier 108 or first recess 110. Apparatus 20 further comprises a second barrier extending in a proximal direction, disposed within tube 22, and distal end 112 of plunger 24 may further be shaped to define a second recess into which the second barrier fits upon plunger 24 being advanced to the barriers. A third filter is disposed at either distal end 100 of tube 22 or distal end 112 of plunger 24, the third filter being separated from second filter 26b by either the second barrier or by the second recess. When apparatus 20 includes three or more filters, as described hereinabove, apparatus 20 includes various combinations of the features described hereinabove with reference to FIGS. 12A-D. In general, the scope of the present invention includes using any number of filters, e.g., three or more.

Figure 12A:
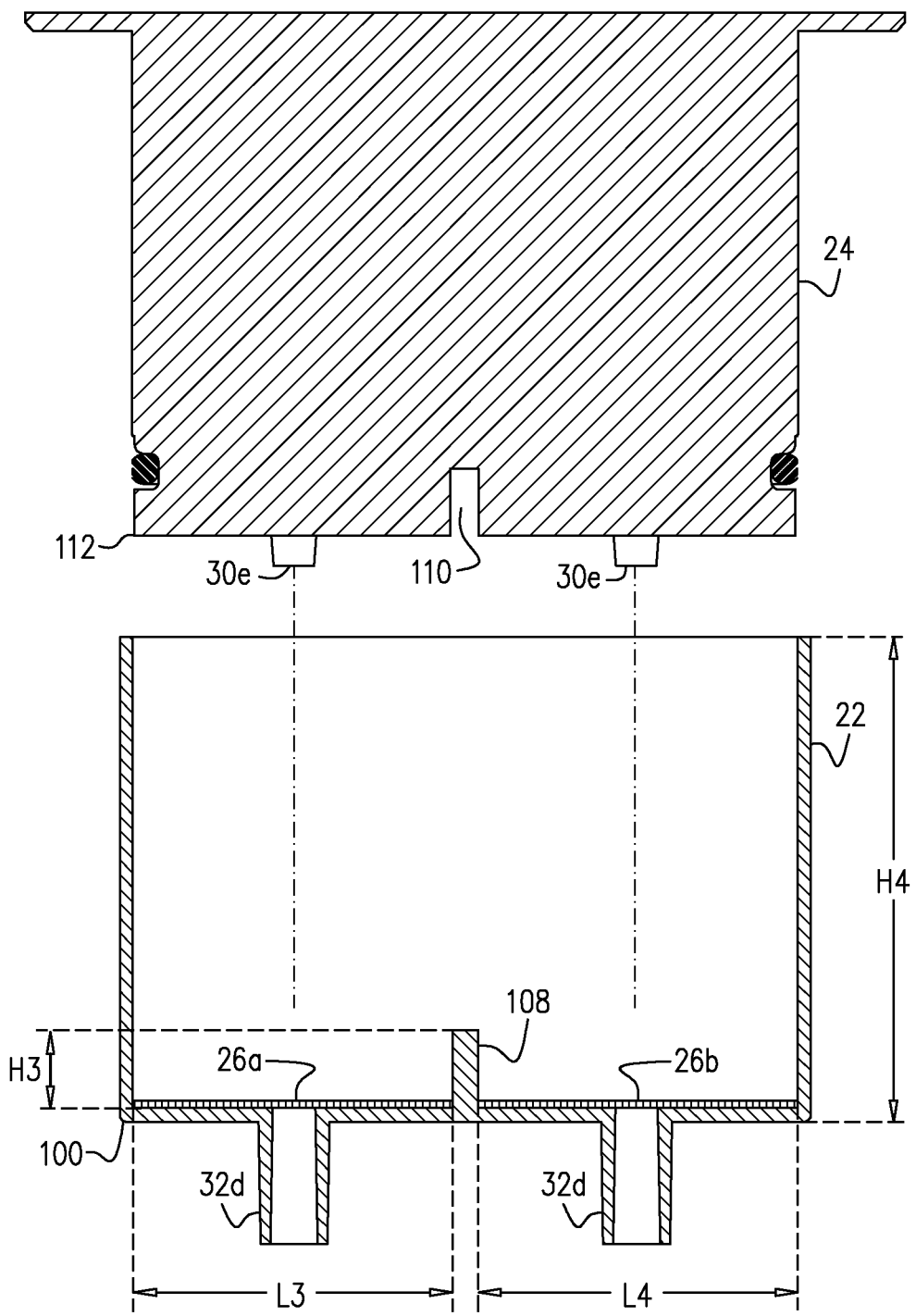
FIGS. 12A-E are schematic illustrations of various configurations of the apparatus for testing for presence of a particulate in a fluid, in accordance with some applications of the present invention.
Figure 12B:
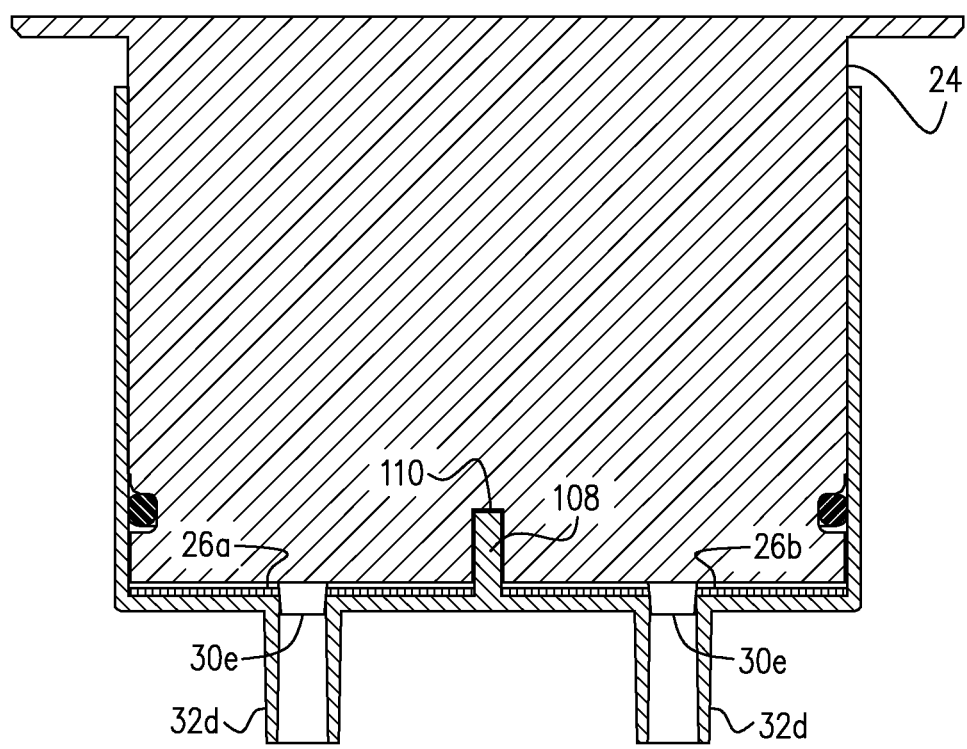
Figure 12C:
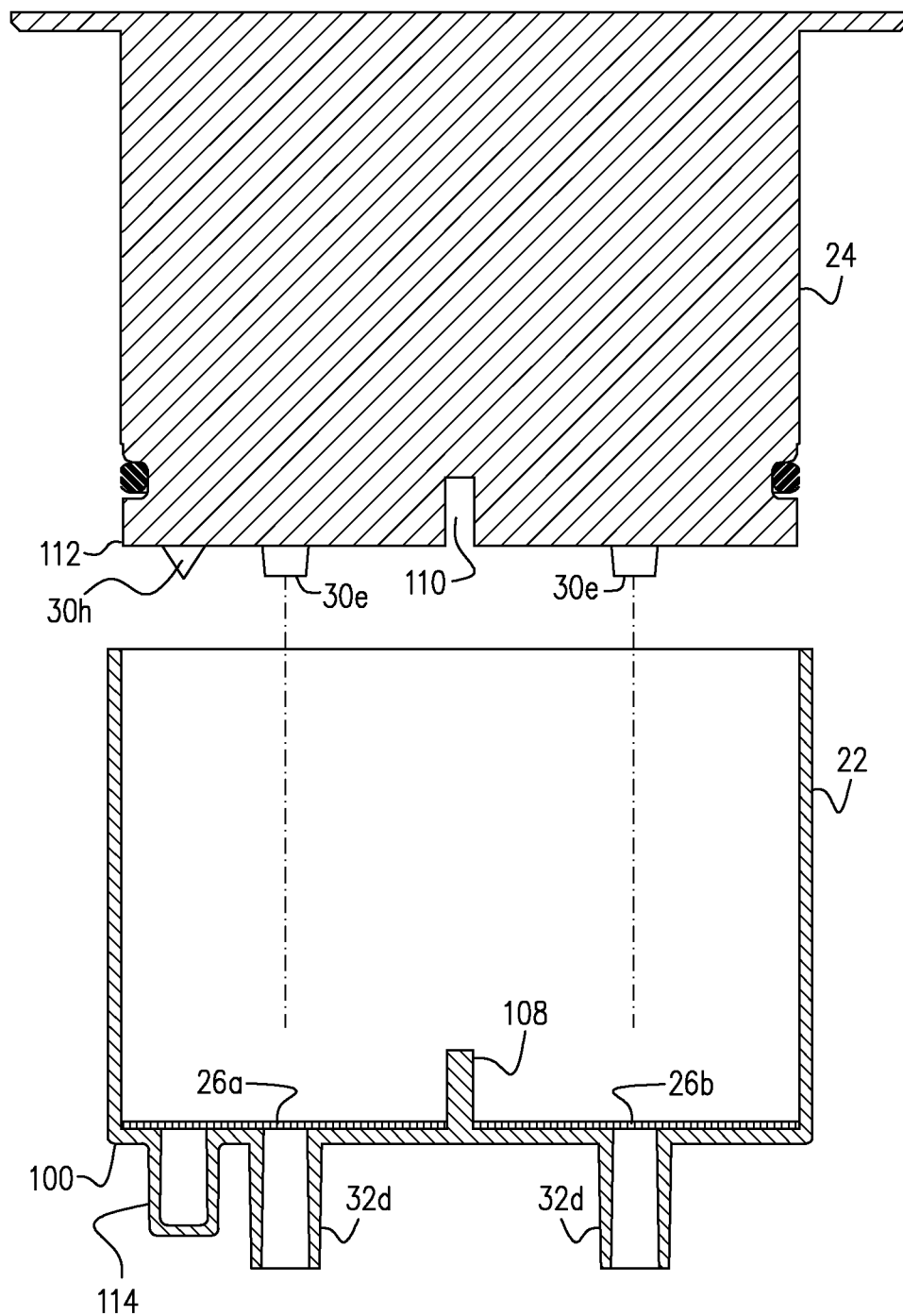
Figure 12D:
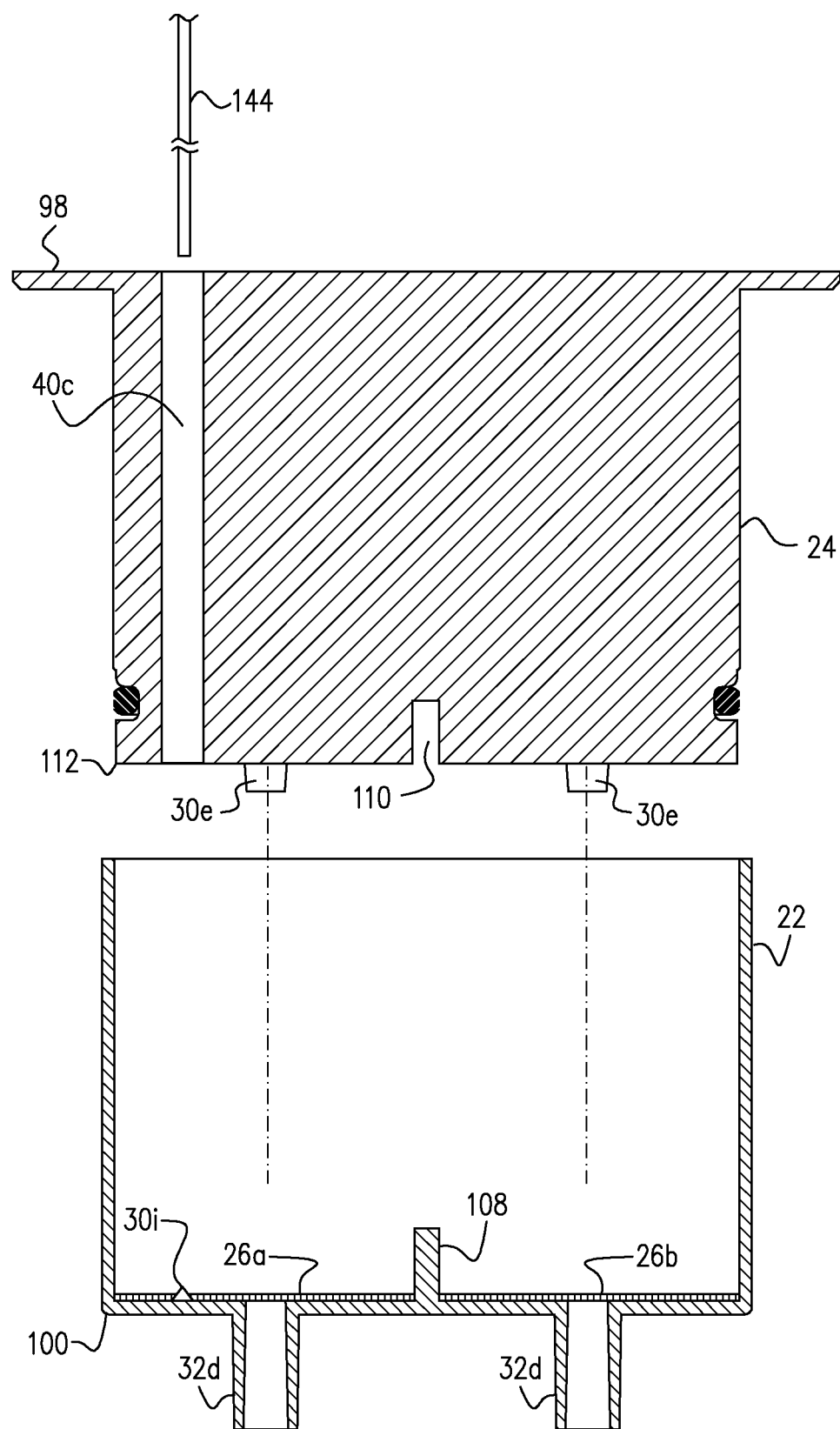
Figure 12E:
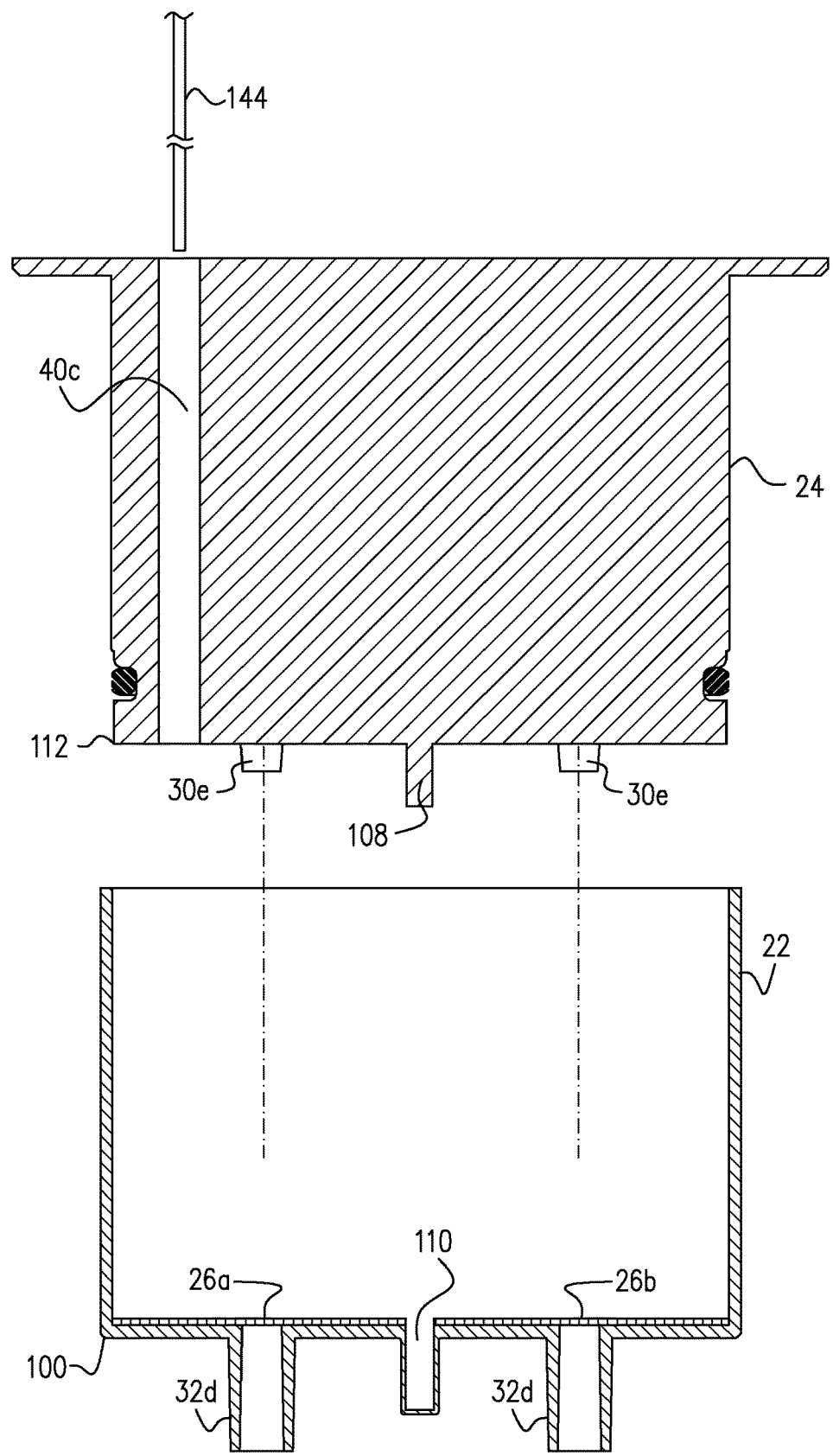

Reference is now made to FIG. 12E, which is a schematic illustration of apparatus 20 in accordance with some applications of the present invention. In some applications, barrier 108 may protrude in a distal direction from distal end 112 of plunger 24, and distal end 100 of tube 22 may be shaped to define recess 110 into which barrier 108 fits upon plunger 24 being advanced to recess 110. When barrier 108 and recess 110 are configured as shown in FIG. 12E, apparatus 20 includes various combinations of the features described hereinabove with reference to FIGS. 12A-D.

Figure 13C:
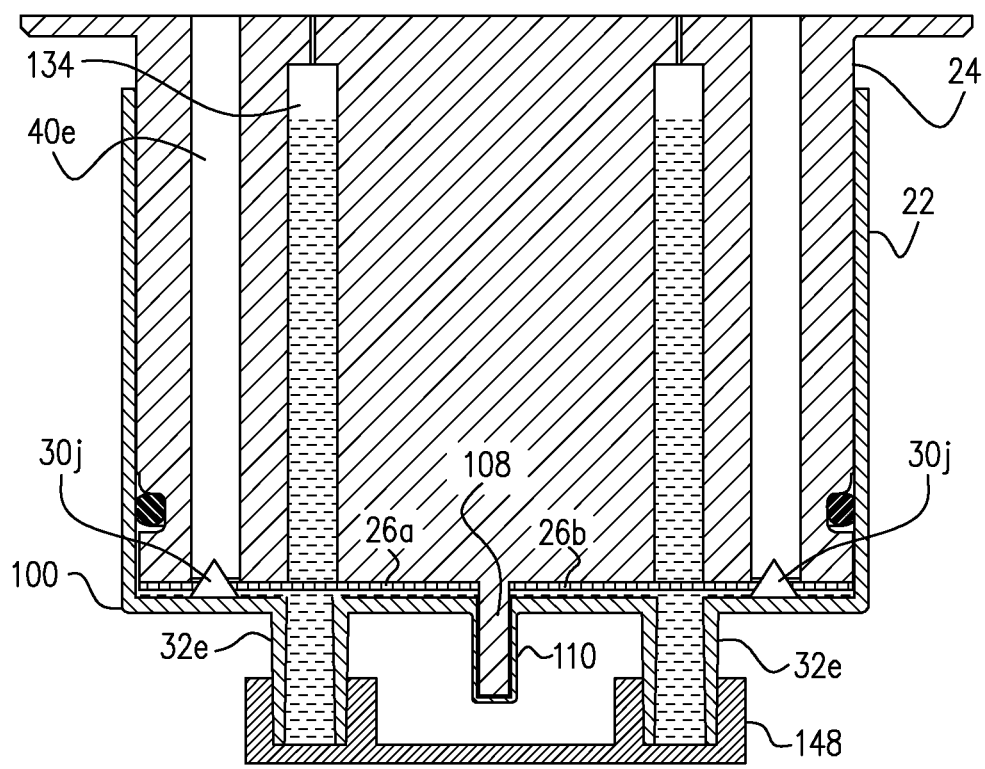
Figure 13D:
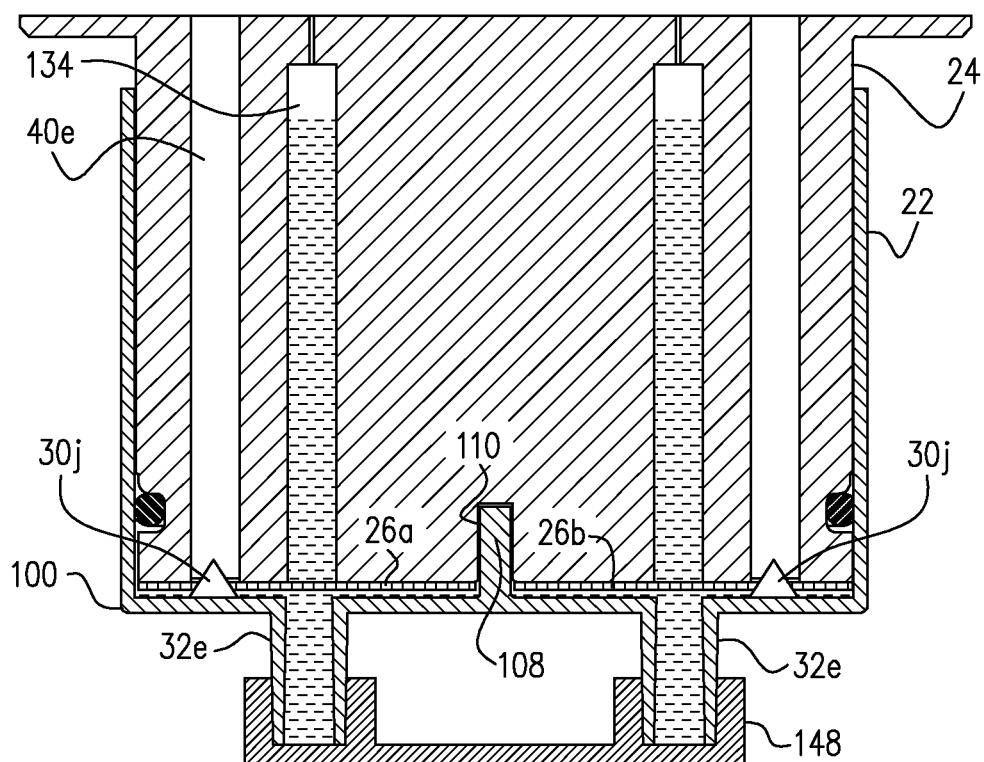

Reference is now made to FIGS. 13A-D, which are schematic illustrations of apparatus 20 in accordance with some applications of the present invention. In some applications, filters 26a and 26b are disposed on distal end 112 of plunger 24 and filters 26a and 26b are separated by (a) recess 110 defined in distal end 112 of plunger 24 (FIGS. 13B and 13D) or (b) barrier 108 protruding in a distal direction from distal end 112 of plunger 24 (FIGS. 13A and 13C). Plunger 24 is shaped to define at least one compartment 134, and pushing the fluid through filters 26a and 26b pushes the fluid into compartment 134 (FIGS. 13C-D). In some applications, tube 22 comprises at least two puncturing elements 30j protruding in a proximal direction from distal end 100 of tube 22 and configured to puncture filters 26a and 26b, respectively, upon plunger 24 being advanced to barrier 108. In some applications, tube 22 does not comprise puncturing elements 30j. In some applications, plunger 24 is shaped to define at least one plunger lumen 40e, an opening of plunger lumen 40e being arranged to align with one of filters 26a or 26b, and not to simultaneously align with the other one of filters 26a or 26b. A distal end of plunger lumen 40e is configured to open upon plunger 24 being maximally advanced within tube 22 by puncturing element 30j, protruding from distal end 100 of tube 22.

In some applications, distal end 100 of tube 22 is shaped to define at least two conduits 32e, configured to align with filters 26a and 26b, respectively. A stopper 148 is initially disposed over the distal openings of conduits 32e. Following pushing the fluid through filters 26a and 26b, apparatus 20 may be turned upside-down such that the proximal end of tube 22 or plunger 24 can be rested on a horizontal surface, stopper 148 removed, and either one of filters 26a or 26b can be tested for presence of the particulate by passing the particulate-presence-testing-facilitation solution through a respective conduit 32e and subsequently inserting a dipstick through the respective conduit 32e.

Reference is now made to FIGS. 14A-B, which are schematic illustrations of apparatus 20, in accordance with some applications of the present invention. In some applications, tube 22 and plunger 24 are shaped to have rotational asymmetry, such that during at least a portion of the advancement of plunger 24 within tube 22, plunger 24 is advanceable within tube 22 in only a single orientation of plunger 24 with respect to tube 22. The rotational asymmetry of plunger 24 and tube 22 facilitates, for example, in respective applications, the ability to easily align the slant of distal end 112 of plunger 24 (FIG. 20) with the slant of distal end 100 of tube 22, as well as the ability to easily align barrier 108 (FIG. 12A) with recess 110 as plunger 24 is advanced in tube 22.

Figure 14C:
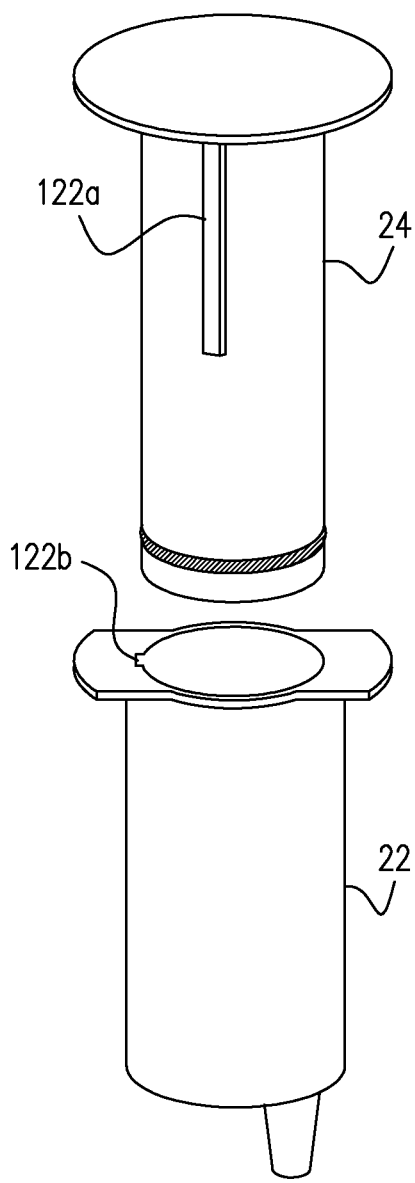
Figure 14D:
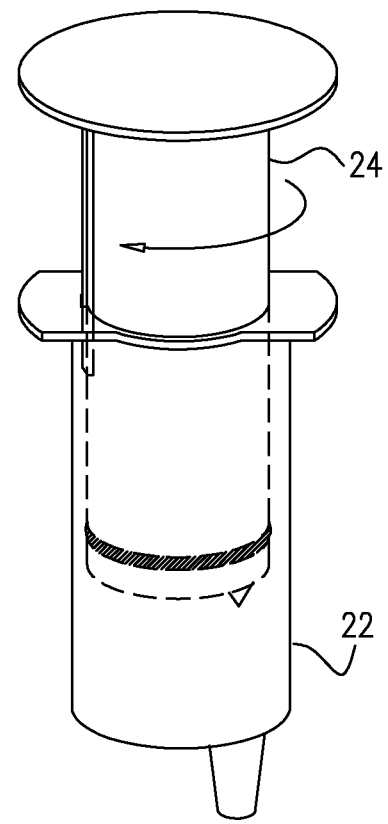

Reference is now made to FIGS. 14C-D, which are schematic illustrations of apparatus 20, in accordance with some applications of the present invention. In some applications, the rotational asymmetry of tube 22 and plunger 24 is achieved by plunger 24 and tube 22 having corresponding interlockable pieces 122a and 122b, such that plunger 24 is advanceable within tube 22 in only a single orientation of plunger 24 with respect to tube 22. Interlockable piece 122a may be disposed on plunger 24 and interlockable piece 122b may be disposed in tube 22 (as shown in FIG. 14C), or they may be disposed in an opposite configuration wherein interlockable piece 122a is in tube 22 and interlockable piece 122b is on plunger 24.

Figure 15A:
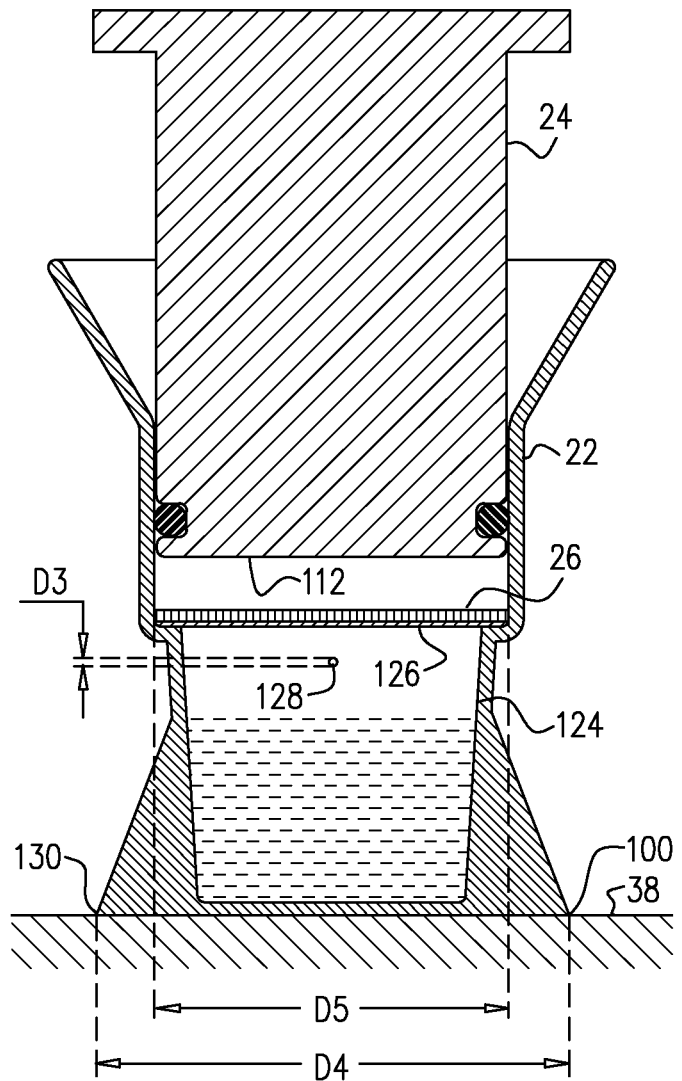
FIGS. 15A-B are schematic illustrations of a configuration of the apparatus for testing for presence of a particulate in a fluid, in accordance with some applications of the present invention.

Reference is now made to FIGS. 15A, which is a schematic illustration of apparatus 20 in accordance with some applications of the present invention. In some applications, tube 22 is closed at a distal end thereof, filter 26 is disposed within tube 22, and tube 22 is shaped to define a fluid-collection compartment 124 distal to filter 26. Plunger 24 is arranged to push fluid through filter 26 and into fluid-collection compartment 124. In some applications, apparatus 20 further comprises a support 126, which is: (a) shaped to define one or more openings, (b) disposed distal to filter 26 within tube 22, (c) in contact with filter 26, and (d) configured to support filter 26 during the pushing of the fluid through filter 26. Typically, support 126 is positioned to inhibit distal movement of plunger 24 past filter 26. A wall of fluid-collection compartment 124 is shaped to define a pressure-release hole 128, such that air pressure in compartment 124, generated by advancing plunger 24, is released through pressure-release hole 128. Typically, a diameter D3 of pressure-release hole 128 is at least 50 microns and/or less than 1500 microns, such that it is small enough for air to easily pass through it but not for a liquid (such as the gargle fluid). Typically, pressure-release hole 128 is disposed above a volume of 2 cc of compartment 124 when distal end 100 of tube 22 is resting on horizontal surface 38. In some applications tube 22 is shaped to define a flat external, surface-contact portion 130 which is shaped to contact horizontal surface 38. Typically surface-contact portion 130 has a diameter D4 which is at least equal to a diameter D5 of filter 26, allowing apparatus 20 to stably balance on distal end 100 of tube 22.

In some applications, plunger 24 is configured to rotate with respect to tube 22 such that friction caused by the rotation of distal end 112 against filter 26 tears filter 26 upon plunger 24 being maximally advanced in tube 22 and subsequently rotated with respect to tube 22.

Figure 15B:
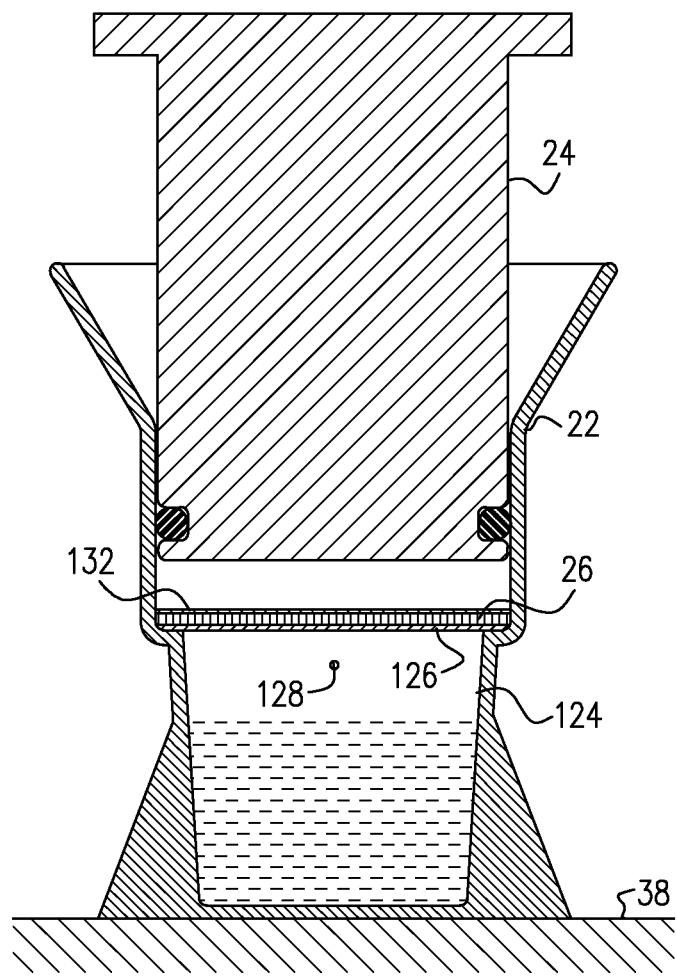

Reference is now made to FIG. 15B, which is a schematic illustration of apparatus 20 in accordance with some applications of the present invention. As plunger 24 is withdrawn from tube 22, a reverse-suction is created in tube 22 that may pull filter 26 in a proximal direction. To prevent this, in some applications, apparatus 20 further comprises a support 132, which is: (a) shaped to define one or more openings, (b) disposed proximal to filter 26 within tube 22, (c) in contact with filter 26, and (d) configured to support filter 26 during withdrawal of plunger 24 in a proximal direction.

Figure 16A:
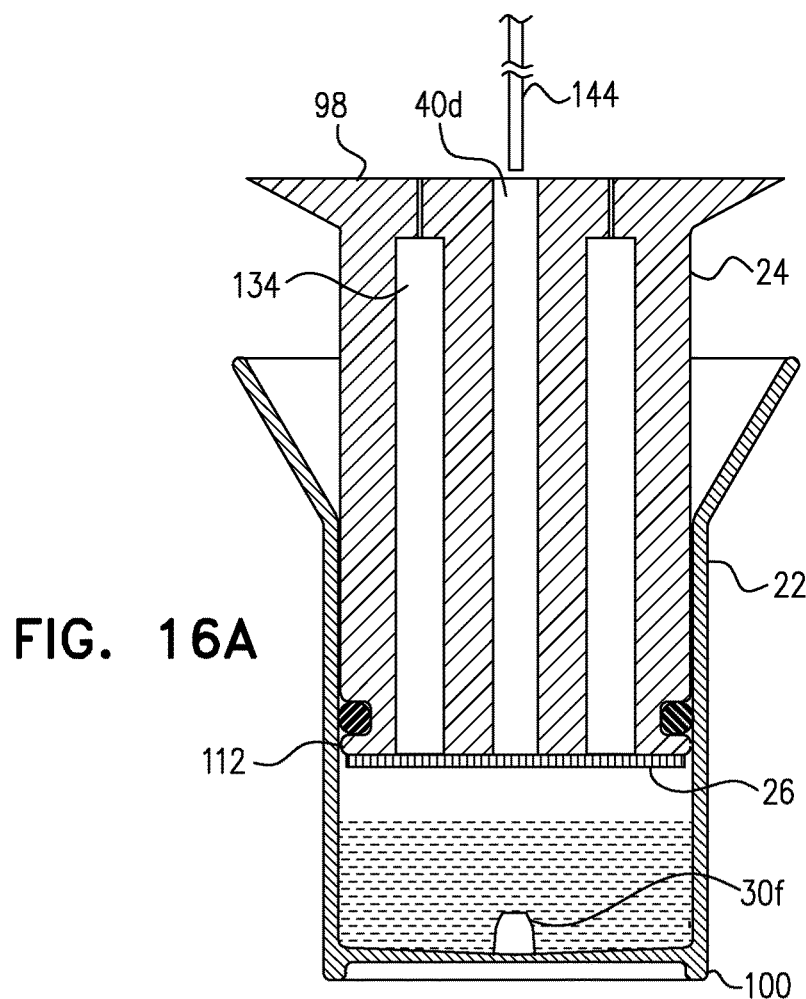
FIGS. 16A-B are schematic illustrations of a configuration of the apparatus for testing for presence of a particulate in a fluid, in accordance with some applications of the present invention.
Figure 16B:
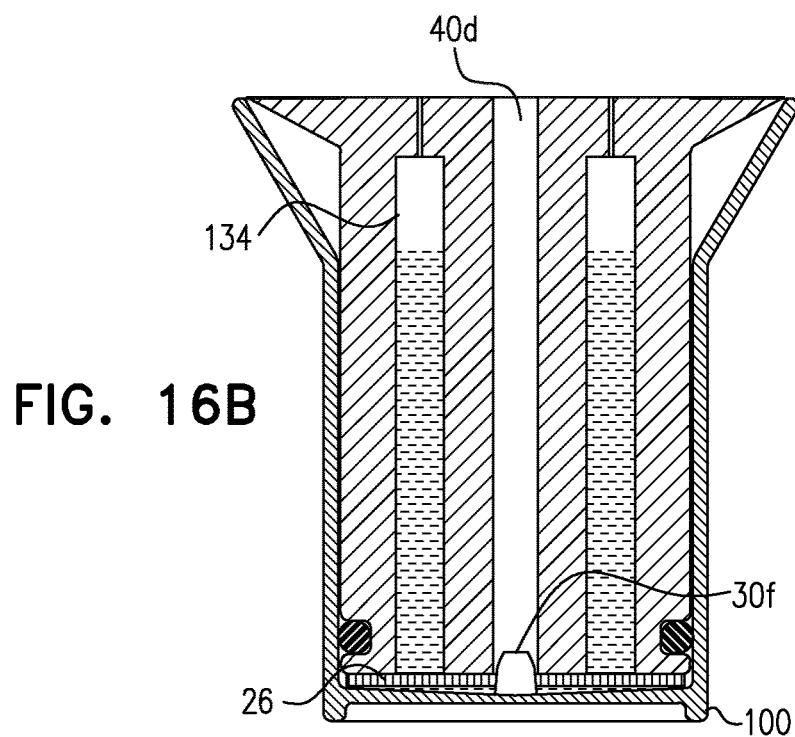

Reference is now made to FIGS. 16A-B, which are schematic illustration of apparatus 20, in accordance with some applications of the present invention. In some applications, filter 26 is disposed on distal end 112 of plunger 24, and a puncturing element 30f protrudes in a proximal direction from distal end 100 of tube 22 and is configured to puncture filter 26 upon plunger 24 being maximally advanced in tube 22. In some applications, plunger 24 is configured to rotate with respect to tube 22 such that puncturing element 30f tears filter 26 upon plunger 24 being maximally advanced in tube 22 and subsequently rotated with respect to tube 22. Plunger 24 is shaped to define at least one compartment 134 and pushing the fluid through filter 26 pushes the fluid into compartment 134 (FIG. 16B). Plunger 24 is further shaped to define plunger lumen 40d, through which the particulate-presence-testing-facilitation solution may be passed and a dipstick inserted. A sample may be taken from filter 26 prior to filter 26 being tested for presence of the particulate by swabbing filter 26 with swab 144 from proximal end 98 of plunger 24 through plunger lumen 40d.

Figure 17A:
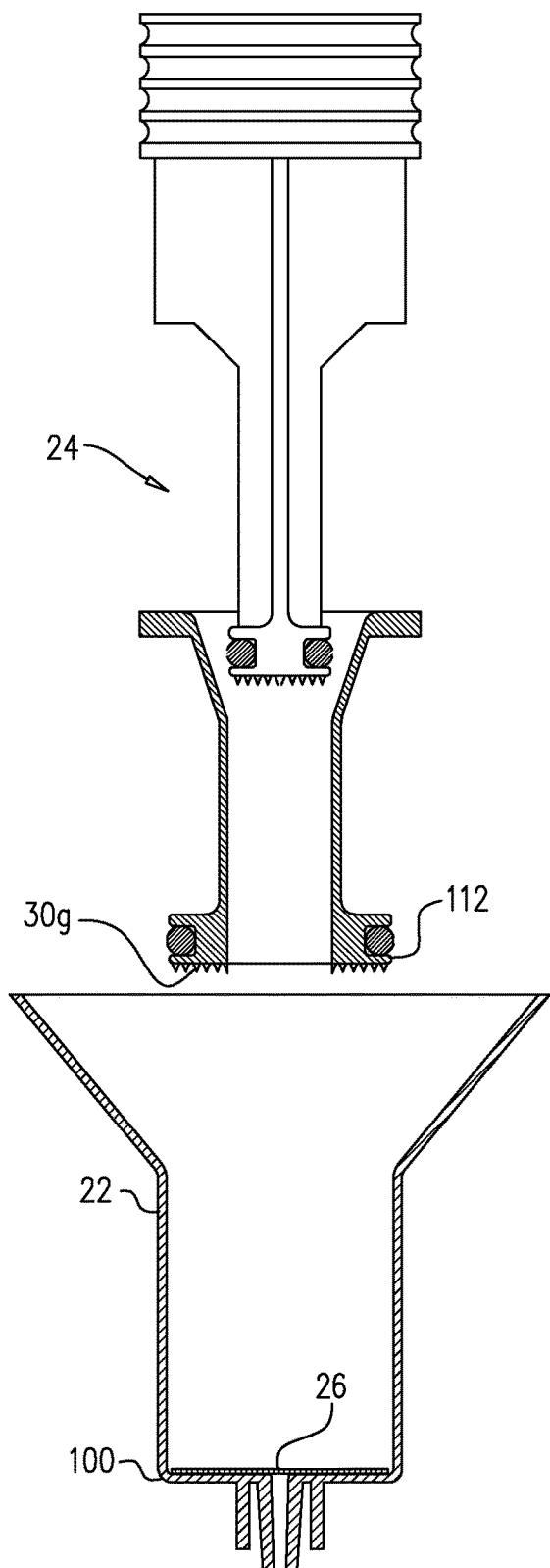
FIGS. 17A-B are schematic illustrations of a configuration of the apparatus for testing for presence of a particulate in a fluid, in accordance with some applications of the present invention.
Figure 17B:
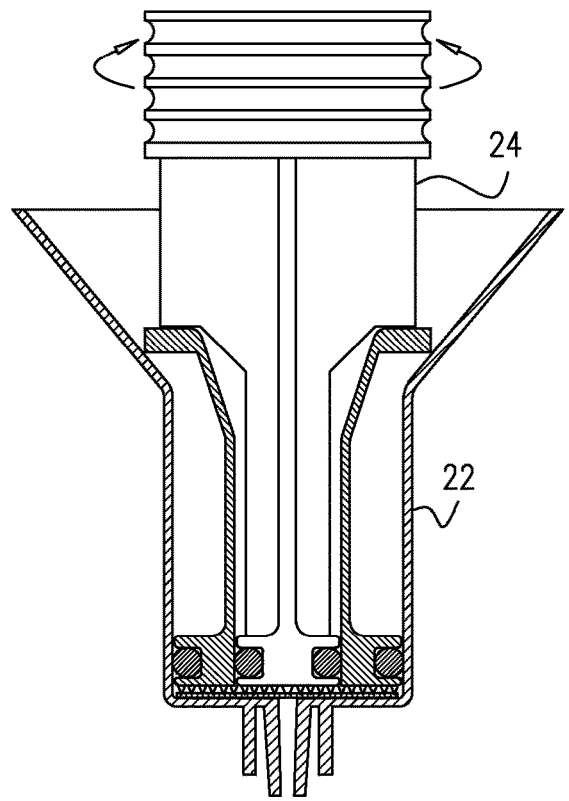

Reference is now made to FIGS. 17A-B, which are schematic illustrations of apparatus 20 in accordance with some applications of the present invention. In some applications, filter 26 is disposed in distal portion of tube 22, and at least one puncturing element 30g protrudes in a distal direction from distal end 112 of plunger 24. Puncturing element 30g is configured to puncture filter 26 upon plunger 24 being maximally advanced within tube 22. In some applications, plunger 24 is configured to rotate with respect to tube 22, when inside tube 22, such that puncturing element 30g tears filter 26 upon plunger 24 being maximally advanced to filter 26 and subsequently rotated with respect to tube 22. Tearing filter 26 further facilitates testing for presence of the particulate, as a larger surface area of filter 26 is exposed to the particulate-presence-testing-facilitation solution.

Figure 18A:
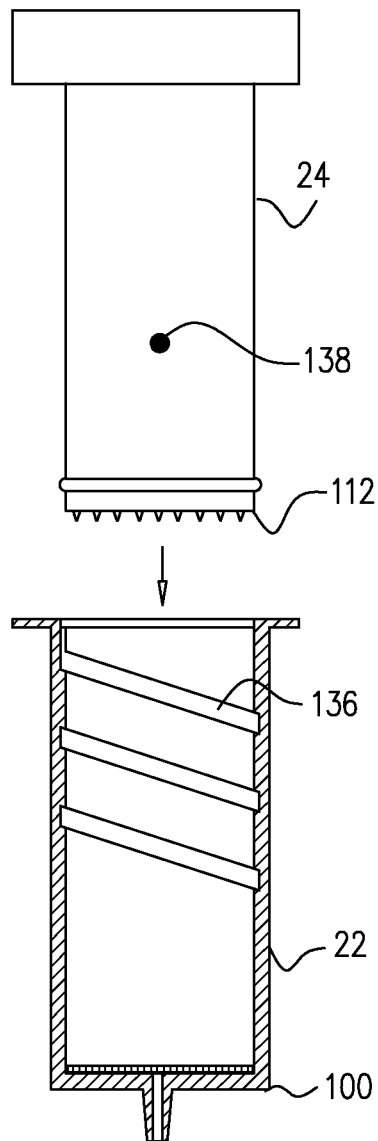
FIGS. 18A-B are schematic illustrations of a threaded tube and a plunger configured to engage the threads, in accordance with some applications of the present invention.
Figure 18B:
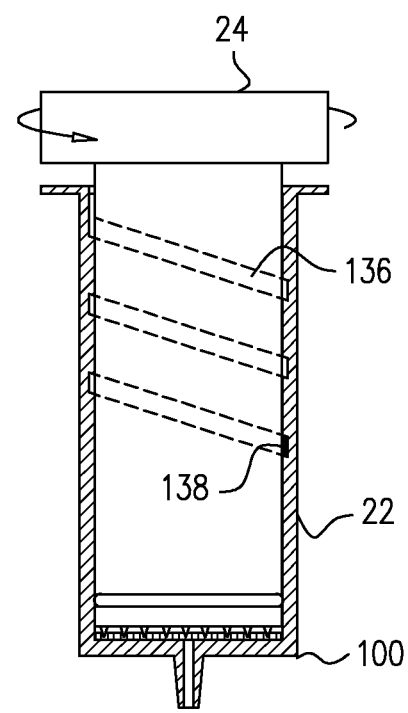

Reference is now made to FIGS. 18A-B, which are schematic illustrations of apparatus 20 in accordance with some applications of the present invention. In some applications, apparatus 20 comprises threading 136 and a protrusion 138 configured to slidably engage threading 136 such that plunger 24 is advanceable within tube 22 by rotation of plunger 24 with respect to tube 22. Advancing plunger 24 by rotation, guided by threading 136, helps control the speed of the advancement and helps maintain steady advancement against pressure in tube 22. In some applications, protrusion 138 and threading 136 are disposed such that threading 136 is on the inside of at least a portion of tube 22 and protrusion 138 protrudes outwards from a wall of plunger 24 (FIG. 18A). In some applications, protrusion 138 and threading 136 are disposed such that threading 136 is on the outside of at least a portion of plunger 24 and protrusion 138 protrudes inwards from a wall of tube 22 (configuration not shown).

Figure 19A:
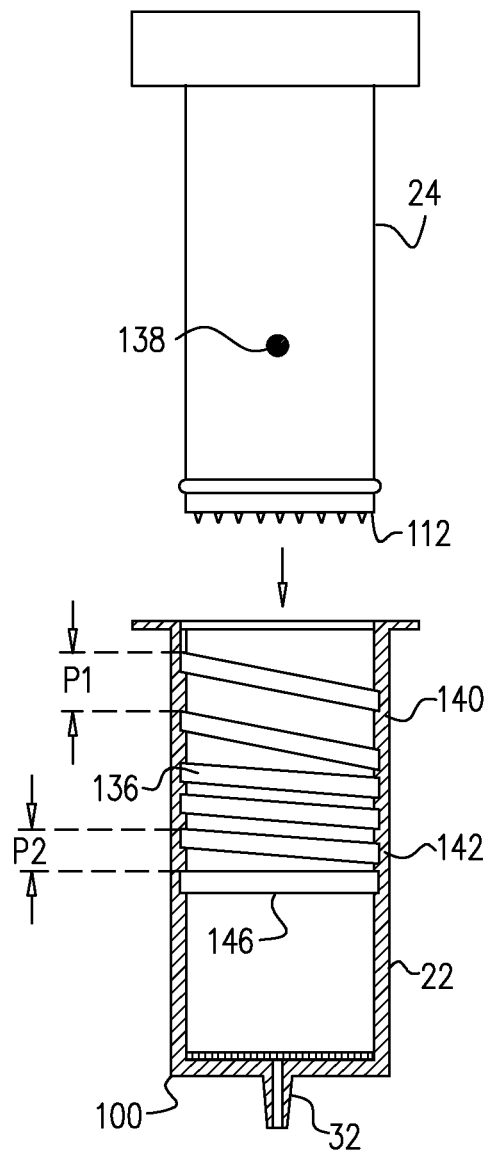
FIGS. 19A-B are schematic illustrations of a threaded tube and a plunger configured to engage the threads, in accordance with some applications of the present invention.
Figure 19B:
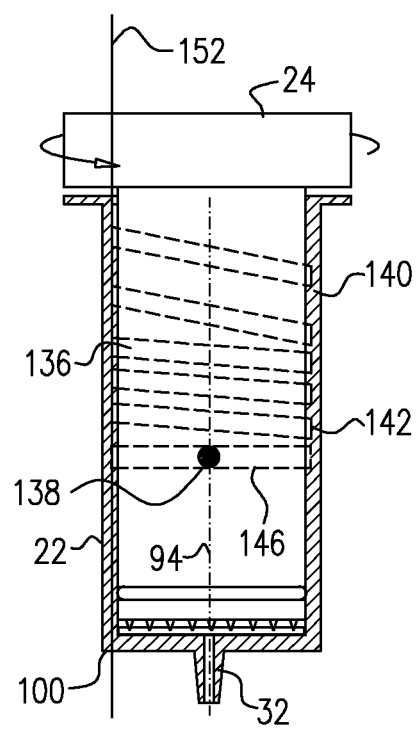

Reference is now made to FIGS. 19A-B, which are schematic illustrations of apparatus 20 in accordance with some applications of the present invention. In some applications, a first pitch P1 of threading 136 at a first location 140 is different from a second pitch P2 of threading 136 at a second location 142. In some applications, second pitch P2 of threading 136 is less than first pitch P1 (FIG. 19A). A decreasing pitch, in a proximal to distal direction, is advantageous for example when filter 26 is disposed on distal end 112 of plunger 24 such that the fluid is being pushed proximally into a compartment in plunger 24, e.g., compartment 134 in FIG. 16A. Advancing plunger 24 through first location 140, corresponding to higher first pitch P1, requires a greater downward force on the proximal end of plunger 24, whereas advancing plunger 24 through second location 142, corresponding to lower second pitch P2, requires less downward force on the proximal end of plunger 24. Initially air (rather than the fluid) is pushed into the compartment, allowing plunger 24 to be pushed through first location 140 with relative ease, and subsequently the fluid is pushed into the compartment, at which point the pitch is decreased to lower pitch P2 to facilitate easier advancement of plunger 24 against the fluid. In addition, as the fluid is pushed through filter 26 the particulate collects on filter 26 such that further advancement of plunger 24 may become more difficult; the transition from higher first pitch P1 to lower second pitch P2 as plunger 24 is advanced helps decrease the force required to push the remaining fluid through filter 26.

In some applications, first pitch P1 of threading 136 at first location 140 is less than second pitch P2 of threading 136 at second location 142 (configuration not shown). An increasing pitch, in a proximal to distal direction, is advantageous for example when filter 26 is disposed in distal end 100 of tube 22, such that the fluid is being pushed distally out of a conduit in distal end 100 of tube 22, e.g., conduit 32. First pitch P1 is lower to facilitate easier advancement of plunger 24 while the fluid is initially pushed out of conduit 32, and subsequently, once the fluid has been pushed out, second pitch P2 is higher for the remaining advancement of plunger 24.

In some applications, a portion 146 of threading 136 that is closest to distal end 100 of tube 22 is perpendicular to a line 152 that is parallel to longitudinal axis 94 of tube 22. Protrusion 138 engages portion 146 of threading 136 when plunger 24 is maximally advanced within tube 22, such that plunger 24 can rotate with respect to tube 22 without further inhibition by threading 136. This uninhibited rotation of plunger 24 with respect to tube 22 facilitates, for example, tearing of filter 26 by rotation of plunger 24 once plunger 24 is maximally advanced within tube 22 and thereby testing for the particulate using the particulate-presence-testing-facilitation solution.

It is noted that apparatus 20 may include various combinations of features shown in FIGS. 1-21.

In general, the scope of the present invention includes using any number of filters, e.g., three or more. Furthermore, the scope of the present invention includes using adhesive properties of a filter to facilitate the trapping of the particulate. For example, mucus from the throat that contains the bacteria, and/or the cell walls of the bacteria, may adhere to the filter.

The scope of the present invention includes testing for various types of particulate matter, in addition to that which is delineated above. For example, apparatus and methods described herein may be used to test for parts of microscopic or macroscopic organisms, or for discharged matter (e.g., eggs) emanating from such organisms.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for testing a biological fluid for presence of a biological particulate, the apparatus comprising:
    a tube having a proximal opening;
    a plunger sized and shaped to be inserted into the tube via the proximal opening and advanceable within the tube while sealably contacting the tube; and
    a filter,
    wherein the apparatus is configured such that as the plunger is advanced within the tube while the biological fluid is within the tube, the biological fluid in the tube is pushed through the filter, thereby trapping, by the filter, the biological particulate present in the biological fluid, wherein the apparatus is shaped so as to define at least one enclosed cavity containing a biological particulate-presence-testing-facilitation solution configured to facilitate testing for the presence of the biological particulate trapped by the filter, and wherein the enclosed cavity is configured to open while the plunger is inside the tube, so as to release the biological particulate-presence-testing-facilitation solution within the tube.

2. The apparatus according to claim 1, wherein the enclosed cavity is configured to open while the plunger is inside the tube, so as to apply the biological particulate-presence-testing-facilitation solution to the filter.

3. The apparatus according to claim 1, wherein the enclosed cavity is configured to open after the biological fluid in the tube is pushed through the filter.

4. The apparatus according to claim 1, wherein the enclosed cavity is configured to open upon the plunger being moved within the tube.

5. The apparatus according to claim 4, wherein the enclosed cavity comprises a seal.

6. The apparatus according to claim 5, wherein the plunger is configured to puncture the seal as the plunger is advanced, thereby opening the enclosed cavity.

7. The apparatus according to claim 1, wherein the plunger is shaped so as to define the at least one enclosed cavity.

8. The apparatus according to claim 7, wherein the filter is disposed on a distal end of the plunger.

9. The apparatus according to claim 7, wherein a distal end of the plunger is shaped so as to define the at least one enclosed cavity.

10. The apparatus according to claim 7, wherein a wall of the plunger is shaped so as to define the at least one enclosed cavity.

11. The apparatus according to claim 7, wherein the at least one enclosed cavity is shaped as a lumen defined by the plunger.

12. The apparatus according to claim 1, wherein a wall of the tube is shaped so as to define the at least one enclosed cavity.

13. The apparatus according to claim 12, wherein a distal wall of the tube is shaped so as to define the enclosed cavity.

14. The apparatus according to claim 12, wherein a distal portion of a lateral wall of the tube is shaped so as to define the enclosed cavity.

15. The apparatus according to claim 1, wherein the biological particulate contains an antigen, and wherein the biological particulate-presence-testing-facilitation solution comprises a releasing agent configured to release the antigen from the biological particulate.

16. The apparatus according to claim 15, wherein the biological particulate is a microorganism containing the antigen.

17. The apparatus according to claim 16, wherein the microorganism is streptococcus bacteria.

18. The apparatus according to claim 1, further comprising a one-way-valve that separates the enclosed cavity from a lumen of the tube.

19. The apparatus according to claim 1, wherein the apparatus is configured to force the biological particulate-presence-testing-facilitation solution out of the enclosed cavity using a gas above atmospheric pressure.

20. The apparatus according to claim 1, wherein the apparatus is configured such that opening of the cavity occurs independently of the plunger.

21. The apparatus according to claim 1, wherein the filter is arranged to allow, while the plunger remains advanced in the tube, the testing for the presence of the biological particulate trapped by the filter.

22. The apparatus according to claim 1, wherein the biological particulate is selected from the group consisting of: a microorganism, a spore, a virus, a mite, a biological cell, a biological antigen, a protein, a protein antigen, and a carbohydrate antigen.

23. The apparatus according to claim 1, wherein the apparatus is configured such that the biological particulate-presence-testing-facilitation solution, upon release from the at least one enclosed cavity, bathes the filter when the plunger is maximally advanced within the tube.

24. The apparatus according to claim 23,
wherein the apparatus is shaped so as to provide an empty volume of 0.03-5 mL in fluid continuity with the filter, and
wherein the apparatus is configured such that the biological particulate-presence-testing- facilitation solution, upon release from the at least one enclosed cavity, collects in the empty volume in fluid continuity with the filter.

25. The apparatus according to claim 24, wherein the empty volume is 0.03-1 mL.

26. The apparatus according to claim 1,
wherein the apparatus is configured such that, when the tube is oriented with the proximal opening facing upward, the biological fluid, upon being deposited in the tube via the proximal opening of the tube, pools at a bottom of the tube prior to advancement of the plunger within the tube, and
wherein the apparatus is configured such that the filter is adjacent and facing the bottom of the tube when the plunger is maximally advanced within the tube.

27. The apparatus according to claim 1,
wherein the apparatus is configured such that, when the tube is oriented with the proximal opening facing upward, the biological fluid, upon being deposited in the tube via the proximal opening of the tube, pools at a bottom of the tube prior to advancement of the plunger within the tube, and
wherein the enclosed cavity is configured to open while the plunger is inside the tube, so as to release the biological particulate-presence-testing-facilitation solution into the bottom of the tube.

28. The apparatus according to claim 5, wherein the apparatus further comprises at least one puncturing element, which is configured to puncture the seal upon the plunger being maximally advanced within the tube, thereby opening the enclosed cavity.

29. The apparatus according to claim 5, wherein the apparatus further comprises at least one puncturing element, which is configured to puncture the seal, thereby opening the enclosed cavity, and to remain in the enclosed cavity upon maximal advancement of the plunger within the tube.

30. A kit comprising the apparatus according to claim 15, the kit further comprising a rapid test dipstick containing an antibody specific to the antigen.

31. The kit according to claim 30, wherein the biological particulate is streptococcus bacteria, wherein the antibody is specific to streptococcus carbohydrate antigen, and wherein the rapid test dipstick comprises a rapid strep test dipstick containing the antibody specific to the streptococcus carbohydrate antigen.

32. A method for testing a biological fluid for presence of a biological particulate, the method comprising:
provided the apparatus for testing the biological fluid for presence of the biological particulate according to claim 1;
collecting, in the tube of the apparatus, the biological fluid that potentially contains the biological particulate;
inserting the plunger into the tube via the proximal opening of the tube, and advancing the plunger within the tube while sealably contacting the tube, so as to push the biological fluid through the filter of the apparatus so as to trap, by the filter, the biological particulate present in the biological filter;
while the filter and the plunger are inside the tube, releasing the biological particulate- presence-testing-facilitation solution inside the tube from the enclosed cavity defined by the apparatus by opening the enclosed cavity; and
testing for the presence of the biological particulate trapped by the filter using the biological particulate-presence-testing-facilitation solution.

33. The method according to claim 32, wherein releasing the biological particulate-presence-testing-facilitation solution inside the tube comprises applying the biological particulate-presence-testing-facilitation solution to the filter.

34. The method according to claim 32, wherein releasing the biological particulate-presence-testing-facilitation solution comprises releasing the biological particulate-presence-testing-facilitation solution inside the tube after advancing the plunger within the tube so as to push the biological fluid through the filter.

35. The method according to claim 32, wherein releasing the biological particulate-presence-testing-facilitation solution inside the tube from the enclosed cavity comprises opening the enclosed cavity by moving the plunger within the tube.

36. The method according to claim 32, wherein the plunger is shaped so as to define the at least one enclosed cavity.

37. The method according to claim 36, wherein the filter is disposed on a distal end of the plunger.

38. The method according to claim 36, wherein a distal end of the plunger is shaped so as to define the at least one enclosed cavity.

39. The method according to claim 36, wherein a wall of the plunger is shaped so as to define the at least one enclosed cavity.

40. The method according to claim 36, wherein the at least one enclosed cavity is shaped as a lumen defined by the plunger.

41. The method according to claim 32, wherein a wall of the tube is shaped so as to define the at least one enclosed cavity.

42. The method according to claim 41, wherein a distal wall of the tube is shaped so as to define the enclosed cavity.

43. The method according to claim 41, wherein a distal portion of a lateral wall of the tube is shaped so as to define the enclosed cavity.

44. The method according to claim 32, wherein the biological particulate contains an antigen, and wherein the biological particulate-presence-testing- facilitation solution includes a releasing agent configured to release the antigen from the biological particulate.

45. The method according to claim 44, wherein the biological particulate is a microorganism containing the antigen.

46. The method according to claim 45, wherein the microorganism is streptococcus bacteria.

47. The method according to claim 44, wherein testing for the presence of the biological particulate trapped by the filter comprises contacting the biological particulate-presence-testing-facilitation solution with a rapid test dipstick containing an antibody specific to the antigen.

48. The method according to claim 47, wherein the biological particulate is streptococcus bacteria, wherein the antibody is specific to streptococcus carbohydrate antigen, and wherein the rapid test dipstick includes a rapid strep test dipstick containing the antibody specific to the streptococcus carbohydrate antigen.

49. The method according to claim 32, wherein releasing the biological particulate-presence-testing-facilitation solution inside the tube comprises forcing the biological particulate-presence-testing-facilitation solution out of the enclosed cavity using a gas above atmospheric pressure.

50. The method according to claim 32, wherein releasing the biological particulate-presence-testing-facilitation solution inside the tube from the enclosed cavity comprises opening the cavity occurs independently of the plunger.

51. The method according to claim 32, wherein testing for the presence of the biological particulate trapped by the filter comprises testing for the presence of the biological particulate while the plunger remains advanced in the tube.

52. The method according to claim 32,
wherein the biological particulate is selected from the group consisting of: a microorganism, a spore, a virus, a mite, a biological cell, a biological antigen, a protein, a protein antigen, and a carbohydrate antigen, and
wherein testing for the presence of the biological particulate comprises testing for the presence of the selected biological particulate.

53. The method according to claim 32, wherein collecting the biological fluid in the tube comprises collecting gargled fluid in the tube.

54. The method according to claim 32, wherein collecting the biological fluid in the tube comprises collecting in the tube a sample selected from the group consisting of: saliva, blood, urine, stool, gastrointestinal fluid, and bronchoalveolar lavage fluid.

55. The method according to claim 32, wherein releasing the biological particulate-presence-testing-facilitation solution inside the tube from the at least one enclosed cavity bathes the filter when the plunger is maximally advanced within the tube.

56. The method according to claim 55,
wherein the apparatus is shaped so as to provide an empty volume of 0.03-5 mL in fluid continuity with the filter, and
wherein releasing the biological particulate-presence-testing-facilitation solution causes the biological particulate-presence-testing-facilitation solution to collect in the empty volume in fluid continuity with the filter.

57. The method according to claim 56, wherein the empty volume is 0.03-1 mL.

58. The method according to claim 32,
wherein collecting the biological fluid in the tube comprises collecting the biological fluid in the tube, via the proximal opening of the tube, while the tube is oriented with the proximal opening facing upward, such that the biological fluid pools at a bottom of the tube prior to advancement of the plunger within the tube, and wherein advancing the plunger within the tube disposes the filter adjacent and facing the bottom of the tube when the plunger is maximally advanced within the tube.

59. The method according to claim 32, wherein collecting the biological fluid in the tube comprises depositing the biological fluid in the tube, via the proximal opening of the tube, while the tube is oriented with the proximal opening facing upward, such that the biological fluid pools at a bottom of the tube prior to advancement of the plunger within the tube, and
wherein releasing the biological particulate-presence-testing-facilitation solution inside the tube comprises releasing the biological particulate-presence-testing-facilitation solution from the enclosed cavity into the bottom of the tube.

60. The method according to claim 32, wherein releasing the biological particulate-presence-testing-facilitation solution inside the tube comprises causing at least one puncturing element of the apparatus to puncture a seal of the enclosed cavity upon the plunger being maximally advanced within the tube, thereby opening the enclosed cavity.

61. The method according to claim 32, wherein releasing the biological particulate-presence-testing-facilitation solution inside the tube comprises causing at least one puncturing element of the apparatus to (a) puncture a seal of the enclosed cavity, thereby opening the enclosed cavity, and (b) remain in the enclosed cavity upon maximal advancement of the plunger within the tube.

\* \* \* \* \*